United States Patent
Nickolaus et al.

(10) Patent No.: US 9,161,927 B2
(45) Date of Patent: Oct. 20, 2015

(54) DRUG COMBINATIONS CONTAINING PDE4 INHIBITORS AND NSAIDS

(75) Inventors: Peter Nickolaus, Warthausen (DE); Rolf Goeggel, Ulm (DE); Daniel Peter, Ummendorf (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 207 days.

(21) Appl. No.: 13/201,270

(22) PCT Filed: Feb. 18, 2010

(86) PCT No.: PCT/EP2010/052079
§ 371 (c)(1),
(2), (4) Date: Sep. 29, 2011

(87) PCT Pub. No.: WO2010/097334
PCT Pub. Date: Sep. 2, 2010

(65) Prior Publication Data
US 2012/0035143 A1    Feb. 9, 2012

(30) Foreign Application Priority Data

Feb. 27, 2009  (EP) .................................. 09153855
Jul. 22, 2009   (EP) .................................. 09166131

(51) Int. Cl.
| A61K 31/196 | (2006.01) |
| A61K 31/44  | (2006.01) |
| A61K 31/519 | (2006.01) |
| A61K 45/06  | (2006.01) |

(52) U.S. Cl.
CPC .............. *A61K 31/196* (2013.01); *A61K 31/44* (2013.01); *A61K 31/519* (2013.01); *A61K 45/06* (2013.01)

(58) Field of Classification Search
CPC ... A61K 31/196; A61K 31/519; A61K 45/06; A61K 31/44
See application file for complete search history.

(56) References Cited

U.S. PATENT DOCUMENTS

| 7,511,045 B2 | 3/2009 | Hoenke et al. |
| 7,723,341 B2 | 5/2010 | Hoenke et al. |
| 2007/0259846 A1 | 11/2007 | Hoenke et al. |
| 2009/0186875 A1 | 7/2009 | Hoenke et al. |
| 2010/0197656 A1 | 8/2010 | Hoenke et al. |
| 2011/0021501 A1 | 1/2011 | Pouzet et al. |

FOREIGN PATENT DOCUMENTS

| CA | 2 605 161 A1 | 10/2006 |
| CA | 2 705 414 A1 | 4/2009 |
| JP | 2008533090 A | 8/2008 |
| WO | 03/024489 A2 | 3/2003 |
| WO | 2006097459 A1 | 9/2006 |
| WO | 2006/111549 A1 | 10/2006 |
| WO | 2009/050248 A1 | 4/2009 |

OTHER PUBLICATIONS

Fleischmann et al. "Meloxicam". Expert Opin. Pharmacother. (2002) 3(10): 1501-1512.*
International Search Report for PCT/EP2010/050925 mailed Mar. 29, 2010.

* cited by examiner

*Primary Examiner* — Sreeni Padmanabhan
*Assistant Examiner* — Jody Karol
(74) *Attorney, Agent, or Firm* — Michael P. Morris; Timothy X. Witkowski

(57) ABSTRACT

The present invention relates to new drug combinations which contain in addition to one or more PDE4-inhibitors at least one NSAID (=non-steroidal anti-inflammatory drug) (2), processes for preparing them and their use in treating in particular respiratory complaints such as for example COPD, chronic sinusitis and asthma.
The invention particularly relates to those drug combinations which contain, in addition to one or more, preferably one PDE4 inhibitor of general formula 1

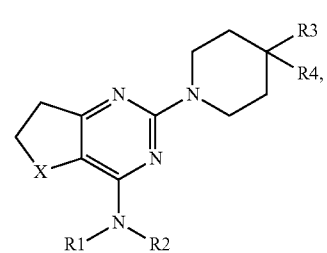

wherein X is SO or $SO_2$, but preferably SO, and wherein $R^1$, $R^2$, $R^3$ and $R^4$ have the meanings given in claim 1, at least one NSAID (2), the preparation thereof and the use thereof for the treatment of respiratory complaints.

28 Claims, 3 Drawing Sheets

Korpergewicht = body weight
zu Tag 1 = on day 1
Uhr = o'clock or hours, i.e. 8 Uhr = 8 o'clock or 0800 hours
Tag = Day
Kontrolle = control Figure 1B: Roflumilast group compared with the control group and the roflumilast + diclofenac group; and diclofenac group compared with the control group (statistics: One-way analysis of variance; ns= not significant; *** = p < 0.001).

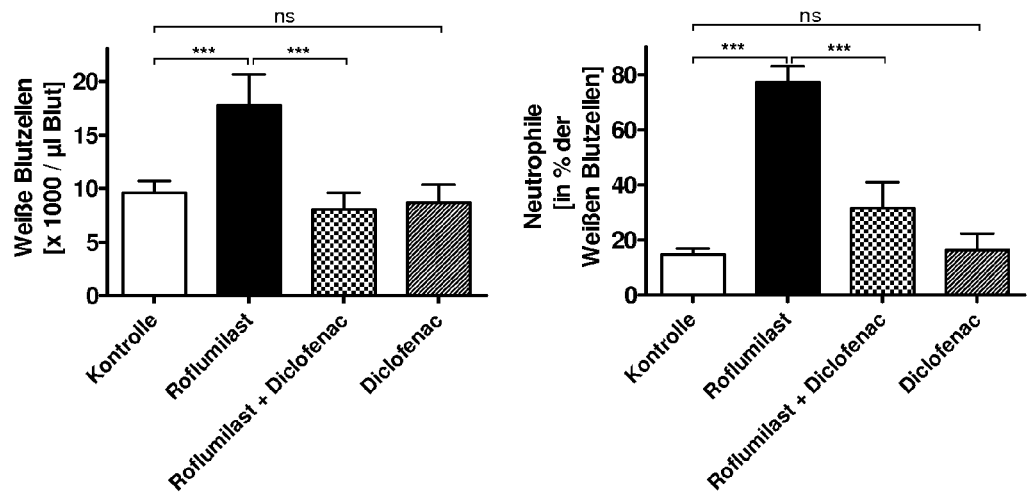

Weiße Blutzellen = white blood cells
Blut = blood
Kontrolle = control
Neutrophilie = neutrophils
in % der Weißen Blutzellen = as a percentage of the white blood cells

Figure 2A:

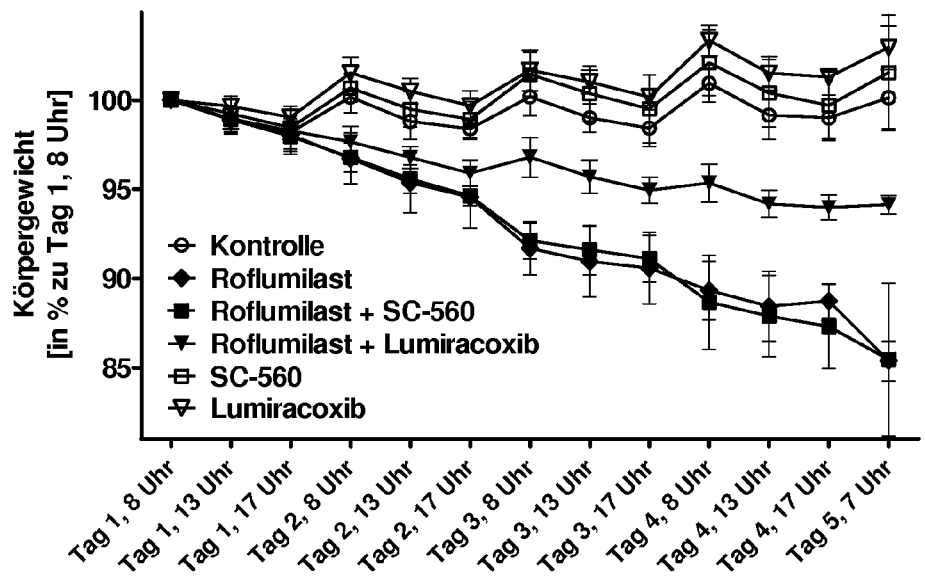

Korpergewicht = body weight
zu Tag 1 = on day 1
Uhr = o'clock or hours, i.e. 8 Uhr = 8 o'clock or 0800 hours
Tag = Day Figure 2B: Roflumilast group compared with the control group, the roflumilast + SC-560 group and the roflumilast + lumiracoxib group; also SC-560 group and lumiracoxib group compared with the control group (statistics: One-way analysis of variance; ns = not significant; * = $p < 0.05$; *** = $p < 0.001$).

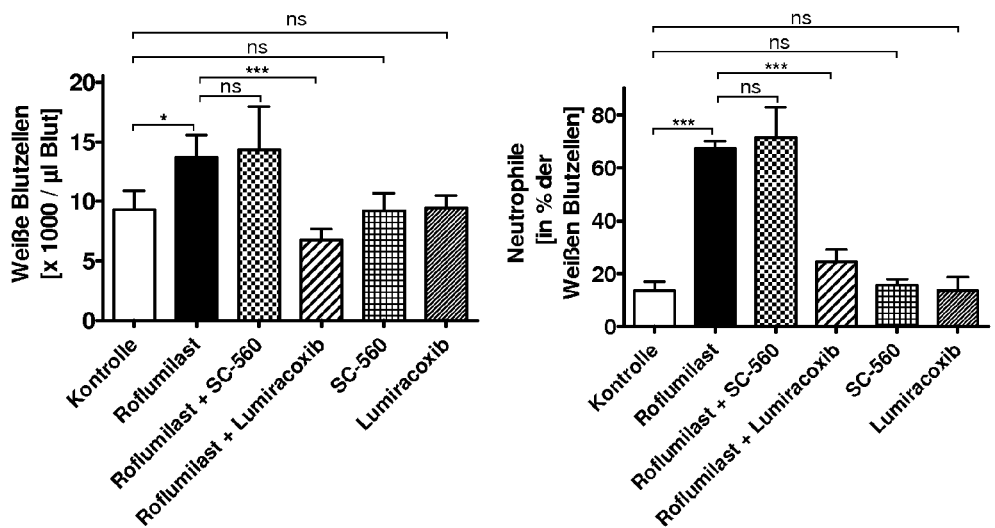

Weiße Blutzellen = white blood cells
Blut = blood
Kontrolle = control
Neutrophilie = neutrophils
in % der Weißen Blutzellen = as a percentage of the white blood cells

DRUG COMBINATIONS CONTAINING PDE4 INHIBITORS AND NSAIDS

This application is the national phase entry under 35 U.S.C. §371 of International Application No. PCT/EP2010/052079, filed Feb. 18, 2010, which claims priority to European Patent Application Nos. 09153855.3, filed Feb. 27, 2009 and 09166131.4, filed Jul. 22, 2009, the contents of which are hereby incorporated by reference in their entireties.

The present invention relates to new drug combinations which contain, in addition to one or more PDE4-inhibitors, at least one NSAID (=non-steroidal anti-inflammatory drug) (2), processes for preparing them and their use for treating in particular respiratory complaints such as for example COPD, chronic sinusitis and asthma.

The invention relates particularly to those drug combinations which comprise, in addition to one or more, preferably one PDE4 inhibitor of general formula 1

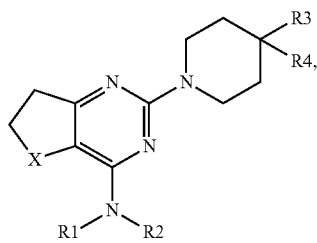

wherein X is SO or $SO_2$, but preferably SO, and wherein $R^1$, $R^2$, $R^3$ and $R^4$ have the meanings given in claim 1, at least one NSAID (2), the preparation thereof and use for the treatment of respiratory complaints.

PRIOR ART

EP 07118901.3 discloses substituted piperidino-dihydrothienopyrimidines of formula 1 as PDE4-inhibitors, the preparation thereof and the use thereof for the treatment of respiratory complaints.

It is also known that many "1st generation" PDE4-inhibitors such as rolipram, for example, lead to undesirable side effects. Consequently, it was an object of the present invention to provide a drug or drug combination containing a PDE4 inhibitor which has a low side-effect profile.

DESCRIPTION OF THE INVENTION

Surprisingly it has now been found that drug combinations that also contain—in addition to a PDE4 inhibitor and in particular in addition to the piperidino-dihydrothienopyrimidinesulphoxides of formula 1 known as PDE4-inhibitors wherein $R^1$, $R^2$, $R^3$ and $R^4$ have the meanings given in claim 1 (1)—at least one NSAID (2), have a significantly lower PDE4-mediated side effect profile compared with a drug that contains the corresponding PDE4 inhibitor or the corresponding piperidino-dihydrothienopyrimidinesulphoxide of formula 1 on its own. Consequently, the dosage of the corresponding dihydrothienopyrimidinesulphoxide of formula 1 (as PDE4 inhibitor) may turn out to be significantly higher, thus increasing its effectiveness in the treatment of for example respiratory complaints such as particularly COPD, chronic sinusitis and asthma while simultaneously retaining a low side effect profile. This therefore gives a larger therapeutic window for the PDE4 inhibitor used.

The present invention therefore relates to a novel drug combination which contains, in addition to one or more PDE4-inhibitors, at least one NSAID (=non-steroidal anti-inflammatory drug) (2).

The present invention preferably relates to drug combinations which in addition to one or more, preferably one compound of general formula 1 as PDE4 inhibitor

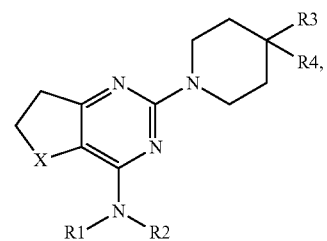

wherein
X denotes SO or $SO_2$,
$R^1$ denotes H, $C_{1-6}$-alkyl,
$R^2$ is H or a group selected from among $C_{1-10}$-alkyl and $C_{2-6}$-alkenyl which may optionally be substituted by one or more groups selected from halogen and $C_{1-3}$-fluoroalkyl or which may optionally be substituted by one or more groups selected from among $OR^{2.1}$, $COOR^{2.1}$, $CONR^{2.2}R^{2.3}$, $SR^{2.1}$, $SO-R^{2.1}$, $SO_2-R^{2.1}$, $C_{6-10}$-aryl, -het, hetaryl, a mono- or bicyclic —$C_{3-10}$-cycloalkyl, $CH_2-NR^{2.2}R^{2.3}$ and $NR^{2.2}R^{2.3}$,
which in turn may optionally be substituted by one or more groups selected from among OH, halogen, $OR^{2.1}$, oxo, $CF_3$, $CHF_2$, $CH_2F$, $C_{1-6}$-alkyl, $C_{1-6}$-alkanol, $C_{6-10}$-aryl, $COOR^{2.1}$, $CH_2-NR^{2.2}R^{2.3}$, and $NR^{2.2}R^{2.3}$,
wherein
het is a three- to eleven-membered, mono- or bicyclic, saturated or partly saturated, optionally anellated or optionally bridged heterocyclic group which contains 1, 2, 3 or 4 heteroatoms selected independently of one another from among N, S or O, and wherein
hetaryl is a five- to ten-membered, mono- or bicyclic, optionally annelated heteroaryl, which contains 1, 2, 3 or 4 heteroatoms selected independently from among N, S or O, and wherein
cycloalkyl may be saturated or partly saturated,
wherein $R^{2.1}$ is H or a group selected from among $C_{1-6}$-alkyl, $C_{1-6}$-alkanol, $C_{1-3}$-haloalkyl, mono- or bicyclic, —$C_{3-10}$-cycloalkyl, $C_{6-10}$-aryl-$C_{1-6}$-alkylene, hetaryl-$C_{1-6}$-alkylene, het-$C_{1-6}$-alkylene, $C_{3-10}$-cycloalkyl-$C_{1-6}$-alkylene, a mono- or bicyclic $C_{6-10}$-aryl, heteroaryl
and a -het,
which may optionally be substituted by one or more groups selected from among OH, O—($C_{1-3}$-alkyl), halogen, $C_{1-6}$-alkyl and $C_{6-10}$-aryl,
wherein $R^{2.2}$ and $R^{2.3}$ independently of one another denote H or denote a group selected from among $C_{1-6}$-alkyl, mono- or bicyclic $C_{3-10}$ cycloalkyl, $C_{6-10}$-aryl-$C_{1-6}$-alkylene, hetaryl-$C_{1-6}$-alkylene, mono- or bicyclic $C_{6-10}$-aryl, het, hetaryl, CO—$NH_2$, CO—$NHCH_3$, —CO—$N(CH_3)_2$, $SO_2$—($C_1$-$C_2$-alkyl), CO—$R^{2.1}$ and $COOR^{2.1}$,
which may optionally be substituted by one or more groups selected from among OH, halogen, $C_{1-6}$-alkyl, $C_{6-10}$-aryl and $COOR^{2.1}$,
or
$R^2$ denotes a mono- or polycyclic $C_{3-10}$ cycloalkyl, which may optionally be singly or multiply bridged by $C_{1-3}$-alkyl groups and which may optionally be substituted by a group selected from among branched or unbranched $C_{1-6}$-alkanol, $C_{1-3}$-fluoroalkyl, $C_{1-3}$-alkylene-$OR^{2.1}$, $OR^{2.1}$, $COOR^{2.1}$, —$SO_2$—$NR^{2.2}R^{2.3}$, het, —NH—CO—O—($C_{1-6}$-alkyl), —NH—CO—($C_{1-6}$-alkyl), —NH—CO—

O—($C_{6-10}$-aryl), —NH—CO—($C_{6-10}$-aryl), —NH—CO—O-hetaryl, —NH—CO-hetaryl, —NH—CO—O—($C_{1-3}$-alkylene)-($C_{6-10}$-aryl), —NH—CO—($C_{1-3}$-alkylene)-($C_{6-10}$-aryl), —N($C_{1-3}$-alkyl)-CO—($C_{1-6}$alkyl), —N($C_{1-3}$-alkyl)-CO—O—($C_{6-10}$-aryl), —N($C_{1-3}$-alkyl)-CO—($C_{6-10}$-aryl), —N($C_{1-3}$-alkyl)-CO—O-hetaryl, —N($C_{1-3}$-alkyl)-CO-hetaryl, —N($C_{1-3}$-alkyl)-CO—O—($C_{1-3}$-alkylene)-($C_{6-10}$-aryl), —N($C_{1-3}$-alkyl)-CO—($C_{1-3}$-alkylene)-($C_{6-10}$-aryl), $C_{6-10}$-aryl, $C_{1-6}$-alkyl, $C_{6-10}$-aryl-$C_{1-6}$-alkylene, hetaryl-$C_{1-6}$-alkylene, mono- or bicyclic $C_{3-10}$ cycloalkyl and $NR^{2.2}R^{2.3}$, which may optionally be substituted by one or more groups selected from among OH, $OR^{2.1}$, oxo, halogen, $CF_3$, $CHF_2$, $CH_2F$, $C_{1-6}$-alkyl, $C_{6-10}$-aryl and $NR^{2.2}R^{2.3}$, or $R^2$ denotes a mono- or polycyclic $C_{6-10}$-aryl, which may optionally be substituted by OH, SH or halogen or by one or more groups selected from among $OR^{2.1}$, $COOR^{2.1}$, $NR^{2.2}R^{2.3}$, $CH_2$—$NR^{2.2}R^{2.3}$, $C_{3-10}$-cycloalkyl, het, $C_{1-6}$-alkyl, $C_{1-3}$-fluoroalkyl, $CF_3$, $CHF_2$, $CH_2F$, $C_{6-10}$-aryl-$C_{1-6}$-alkylene, het-$C_{1-6}$-alkylene, hetaryl-$C_{1-6}$-alkylene, $C_{6-10}$-aryl, $SO_2$—$CH_3$, $SO_2$—$CH_2CH_3$ and $SO_2$—$NR^{2.2}R^{2.3}$, which may in turn optionally be substituted by one or more groups selected from among OH, $OR^{2.1}$, $CF_3$, $CHF_2$, $CH_2F$, oxo, halogen, $CF_3$, $CHF_2$, $CH_2F$, $C_{1-6}$-alkyl, $C_{6-10}$-aryl and $NR^{2.2}R^{2.3}$, or $R^2$ denotes a group selected from among het and hetaryl, which may optionally be substituted by one or more groups selected from among halogen, OH, oxo, $CF_3$, $CHF_2$ and $CH_2F$ or by one or more groups selected from among $OR^{2.1}$, $C_{1-3}$-alkylene-$OR^{2.1}$, $SR^{2.1}$, SO—$R^{2.1}$, $SO_2$—$R^{2.1}$, $COOR^{2.1}$, $COR^{2.1}$, $C_{1-6}$-alkanol, mono- or bicyclic $C_{3-10}$-cycloalkyl, $C_{6-10}$-aryl, $C_{1-6}$-alkyl, $C_{6-10}$-aryl-$C_{1-6}$-alkylene, hetaryl-$C_{1-6}$-alkylene, het, hetaryl, $C_{1-3}$-alkylene-$OR^{2.1}$ and $NR^{2.2}R^{2.3}$, which in turn may optionally be substituted by one or more groups selected from among OH, $OR^{2.1}$, oxo, halogen, $CF_3$, $CHF_2$, $CH_2F$, $C_{1-6}$-alkyl, $C_{6-10}$-aryl and $NR^{2.2}R^{2.3}$, or wherein $NR^1R^2$ together denotes a heterocyclic $C_{4-7}$ ring which may optionally be bridged, which contains 1, 2 or 3 heteroatoms selected from among N, O and S and which may optionally be substituted by one or more groups selected from among OH, $OR^{2.1}$, $C_{1-3}$-alkylene-$O^{R.1}$, oxo, halogen, $C_{1-6}$-alkyl, $C_{6-10}$-aryl, $COOR^{2.1}$, $CH_2$—$NR^{2.2}$—COO—$R^{2.1}$, $CH_2$—$NR^{2.2}$—CO—$R^{2.1}$, $CH_2$—$NR^{2.2}$—CO—$CH_2$—$NR^{2.2}R^{2.3}$, $CH_2$—$NR^{2.2}$—$SO_2$—$C_{1-3}$-alkyl, $CH_2$—$NR^{2.2}$—$SO_2$—$NR^{2.2}R^{2.3}$, $CH_2$—$NR^{2.2}$—CO—$NR^{2.2}R^{2.3}$, CO—$NR^{2.2}R^{2.3}$, $CH_2$—$NR^{2.2}R^{2.3}$ and $NR^{2.2}R^{2.3}$, and wherein $R^3$ is a $C_{6-10}$-aryl, which is optionally substituted in the ortho, para or meta position by one, two or three groups selected independently from among fluorine, chlorine, bromine, hydroxy, CN, $C_{1-6}$-alkyl, $C_{1-3}$-fluoroalkyl, —$C_{1-3}$-alkylene-$OR^{2.1}$, —$C_{1-3}$-alkylene-$NR^{2.2}R^{2.3}$, —$NR^{2.2}R^{2.3}$, O—$R^{2.1}$; SO—$R^{2.1}$, $SO_2$—$R^{2.1}$, $COOR^{2.1}$, —CO—NH—($C_{1-6}$-alkylene)-hetaryl, —CO—NH-hetaryl, —CO—N($CH_3$)-het, —CO—N($CH_3$)—($C_{1-3}$-alkylene)-het, —CO—N($CH_3$)—($C_{1-3}$-alkylene)-hetaryl, —CO—N($C_{3-7}$-cycloalkyl)-het, —CO—$NR^{2.2}R^{2.3}$, —CO—NH—($C_{1-6}$-alkylene)-het, $NR^{2.2}$—CO—$R^{2.1}$, $C_{6-10}$-aryl, $C_{6-10}$-aryl-$C_{1-2}$-alkylene, het-$C_{1-2}$-alkylene, -het, —CO-het, CO—N($CH_3$)—$C_{3-7}$-cycloalkyl, $C_{3-7}$-cycloalkyl, $C_{3-7}$-cycloalkyl-$C_{1-2}$-alkylene, hetaryl-$C_{1-2}$-alkylene and hetaryl, while this group may optionally be substituted by one or more groups selected from among OH, halogen, —$C_{1-3}$-fluoroalkyl, oxo, methyl and phenyl, or wherein $R^3$ is a group selected from among het and hetaryl, which may optionally be substituted by one or more groups selected from among halogen, $C_{1-3}$-fluoroalkyl, CN, OH, oxo, —$C_{1-6}$-alkyl, —$C_{1-3}$-alkylene-$NR^{2.2}R^{2.3}$, —$NR^{2.2}R^{2.3}$, SO—$R^{2.1}$, $SO_2$—$R^{2.1}$, —O—$R^{2.1}$, —$COOR^{2.1}$, $SO_2$—($CH_3$), $SO_2$—($CH_2$—$CH_3$), $C_{6-10}$-aryl, het, $C_{3-7}$-cycloalkyl and hetaryl, which in turn may optionally be substituted by one or more groups selected from among OH, halogen, —$C_{1-3}$-fluoroalkyl, $C_{1-6}$-alkyl, $C_{6-10}$-aryl, —COO($C_{1-3}$-alkyl) and O—($C_{1-3}$-alkyl), or wherein $R^3$ denotes —O—$R^{3.1}$, wherein $R^{3.1}$ is a group selected from among —$C_{1-6}$-alkyl, —$C_{6-10}$-aryl, —$C_{1-3}$-alkylene-$C_{6-10}$-aryl, hetaryl and het, which is optionally substituted in the ortho, para or meta position by one, two or three groups selected independently of one another from among fluorine, chlorine, bromine, hydroxy, CN, $C_{1-6}$-alkyl, $C_{1-3}$-fluoroalkyl, CO—($C_{1-5}$-alkyl), —CO—($C_{1-3}$-fluoroalkyl), —CO—NH—($C_{1-6}$-alkylene)-hetaryl,
—CO—N($C_{1-3}$-alkyl)-($C_{1-6}$-alkylene)-hetaryl,
—CO—N($C_{1-3}$-alkyl)-het, —CO—N($C_{3-7}$-cycloalkyl)-het, —$C_{1-3}$-alkylene-$OR^{2.1}$,
—$C_{1-3}$-alkylene-$NR^{2.2}R^{2.3}$, —$NR^{2.2}R^{2.3}$, O—$R^{2.1}$;
SO—$R^{2.1}$, $SO_2$—$R^{2.1}$, COOH, COO—($C_{1-4}$-alkyl), —O—$C_{1-3}$-alkylene-N($C_{1-3}$-alkyl)$_2$, CO—$NR^{2.2}R^{2.3}$, $NR^{2.2}$—CO—$R^{2.1}$, $C_{6-10}$-aryl, $C_{6-10}$-aryl-$C_{1-2}$-alkylene, het-$C_{1-2}$-alkylene, —CO-het, het,
—CO—$C_{3-7}$-cycloalkyl, —CO—N($C_{1-3}$-alkyl)-$C_{3-7}$-cycloalkyl
$C_{3-7}$-cycloalkyl, $C_{3-7}$-cycloalkyl-$C_{1-2}$-alkylene, hetaryl-$C_{1-2}$-alkylene and hetaryl, which in turn may optionally be substituted by 1, 2, 3 or 4 groups selected independently of one another from among F, Cl, Br, methyl, O-methyl, ethyl, O-ethyl, OH, oxo and $CF_3$.

and wherein $R^4$ denotes H, CN, OH, $CF_3$, $CHF_2$, $CH_2F$, F, methyl, ethyl, —O—($C_{1-3}$-alkyl), —$C_{1-3}$-alkylene-OH, —COO($C_{1-3}$-alkyl), —CO-het, —($C_{1-2}$-alkylene)-NH—$SO_2$—($C_{1-2}$-alkyl), —($C_{1-2}$-alkylene)-N($C_{1-3}$-alkyl)-$SO_2$—($C_{1-2}$-alkyl), —($C_{1-2}$-alkylene)-O—($C_{1-2}$-alkylene)-$C_{6-10}$-aryl, —$C_{1-3}$-alkylene-O—$C_{1-3}$-alkyl, —($C_{1-2}$-alkylene)-N($C_{1-3}$-alkyl)-CO—($C_{1-2}$-alkyl), —NH—CO—($C_{1-3}$-alkylene)-O—($C_{1-3}$-alkyl), —$C_{1-3}$-alkylene-NH—CO—($C_{1-3}$-alkyl), —$C_{1-3}$-alkylene-NH—CO—($C_{1-3}$-alkylene)-N($C_{1-3}$-alkyl)$_2$, —O—($C_{1-2}$-alkylene)-($C_{6-10}$-aryl), —$C_{1-3}$-alkylene-NH—CO—($C_{1-3}$-alkylene)-O—($C_{1-3}$-alkyl), —CO—($C_{6-10}$-aryl), —($C_{1-2}$-alkylene)-N($C_{1-3}$-alkyl)-CO—($C_{1-2}$-alkylene)-O—($C_{1-3}$-alkyl), while the aryl in the above groups may in turn optionally be substituted by one or more additional groups selected from among F, Cl, Br, methyl, ethyl, propyl, isopropyl, cyclopropyl, —O-methyl, —O-ethyl, —O-propyl, —O-isopropyl, —O-cyclopropyl, —OH and $CF_3$ or wherein $R^3$ and $R^4$ together form a mono- or bicyclic, unsaturated, saturated or partly saturated heterocyclic group which contains 1, 2 or 3 heteroatoms selected from among N, O and S and which may optionally be substituted by one or more groups selected from among halogen, OH, oxo, $C_{1-3}$-fluoroalkyl, CN, $C_{1-6}$-alkyl, —O—$R^{2.1}$, —COO$R^{2.1}$, SO—$R^{2.1}$, $SO_2$—$R^{2.1}$, —$C_{1-3}$-alkylene-$NR^{2.2}R^{2.3}$, —$NR^{2.2}R^{2.3}$, $C_{6-10}$-aryl, $C_{3-7}$-cycloalkyl, het and hetaryl, contain at least one NSAID (=non-steroidal anti-inflammatory drug) (2).

Preferred drug combinations are those which, in addition to one or more, preferably one compound of formula 1 as PDE4 inhibitor, wherein X denotes SO, $R^1$ denotes H $R^2$ is H or $C_{1-6}$-alkyl, which may optionally be substituted by one or more groups selected from F, Cl, $CF_3$, $CHF_2$ or $CH_2F$ or which may optionally be substituted by one or more groups selected from among $OR^{2.1}$, $COOR^{2.1}$, $CONR^{2.2}R^{2.3}$, $SR^{2.1}$, SO—$R^{2.1}$, $SO_2$—$R^{2.1}$, phenyl, het, hetaryl, a monocyclic $C_{3-7}$-cycloalkyl, $CH_2$—$NR^{2.2}R^{2.3}$ and $NR^{2.2}R^{2.3}$, which in turn may optionally be substituted by one or more groups selected from among OH, F, Cl, Br, $CF_3$, $CHF_2$, $CH_2F$, $OR^{2.1}$, oxo, methyl, ethyl, propyl, isopropyl, methanol, ethanol, phenyl, $COOR^{2.1}$, $CH_2$—$NR^{2.2}R^{2.3}$ and $NR^{2.2}R^{2.3}$, wherein het is a three- to seven-membered, monocyclic, saturated or partly saturated heterocyclic group which contains 1, 2 or 3 heteroatoms selected independently of one another from among N, S or O, and wherein hetaryl is a five- to six-membered, monocyclic, aromatic heteroaryl which contains 1, 2 or 3 heteroatoms selected independently of one another from among N, S or O, and wherein cycloalkyl may be saturated or partly saturated, wherein $R^{2.1}$ is H or a group selected from among methyl, ethyl, propyl, isopropyl, methanol, ethanol, monocyclic $C_{3-7}$ cycloalkyl, phenyl-$C_{1-2}$-alkylene, -hetaryl-$C_{1-2}$-alkylene, -het-$C_{1-2}$-alkylene, $C_{3-7}$-cycloalkyl-$C_{1-2}$-alkylene, phenyl, hetaryl and a het, which may optionally be substituted by one or more groups selected from among OH, F, Cl, methyl, ethyl, propyl, isopropyl, O-methyl, O-ethyl, O-propyl, O-isopropyl and phenyl, wherein $R^{2.2}$ and $R^{2.3}$ independently of one another denote H or a group selected from among methyl, ethyl, propyl, isopropyl, monocyclic $C_{3-7}$-cycloalkyl, phenyl-$C_{1-3}$-alkylene, hetaryl-$C_{1-3}$-alkylene, phenyl, -het, -hetaryl, CO—$NH_2$, CO—$NHCH_3$, $CON(CH_3)_2$, $SO_2$—($C_{1-2}$-alkyl), CO—$R^{2.1}$ and $COOR^{2.1}$, which may optionally be substituted by one or more groups selected from among OH, F, Cl, methyl, ethyl, propyl, isopropyl, phenyl and $COOR^{2.1}$, or $R^2$ denotes a monocyclic $C_{3-7}$ cycloalkyl, which may optionally be substituted by a group selected from among $C_{1-2}$-alkanol, $C_{1-3}$-fluoroalkyl, $C_{1-3}$-alkylene-$OR^{2.1}$, $OR^{2.1}$, $COOR^{2.1}$, $SO_2$—$NR^{2.2}R^{2.3}$, -het, —NH—CO—O-(phenyl), methyl, ethyl, propyl, isopropyl, phenyl, phenyl-$C_{1-2}$-alkylene, -hetaryl-$C_{1-2}$-alkylene, monocyclic $C_{3-7}$ cycloalkyl and $NR^{2.2}R^{2.3}$, which may optionally be substituted by one or more groups selected from among OH, $OR^{2.1}$, oxo, F, Cl, $CF_3$, $CHF_2$, $CH_2F$, methyl, ethyl, propyl, isopropyl, phenyl and $NR^{2.2}R^{2.3}$, or $R^2$ denotes a phenyl which may optionally be substituted by OH, SH, F, Cl or Br or by one or more groups selected from among $OR^{2.1}$, $COOR^{2.1}$, $NR^{2.2}R^{2.3}$, $CH_2$—$NR^{2.2}R^{2.3}$, monocyclic $C_{3-7}$-cycloalkyl, -het, methyl, ethyl, propyl, isopropyl, $CF_3$, $CHF_2$, $CH_2F$, phenyl-$C_{1-2}$-alkylene, het-$C_{1-2}$-alkylene, hetaryl-$C_{1-2}$-alkylene, phenyl, $SO_2$—$CH_3$, $SO_2$—$CH_2CH_3$ and $SO_2$—$NR^{2.2}R^{2.3}$, which in turn may optionally be substituted by one or more groups selected from among OH, $OR^{2.1}$, oxo, F, Cl, $CF_3$, $CHF_2$, $CH_2F$, methyl, ethyl, propyl, isopropyl, phenyl and $NR^{2.2}R^{2.3}$, or $R^2$ denotes a group selected from among het and hetaryl, which may optionally be substituted by one or more groups selected from among F, Cl, OH, oxo, $CF_3$, $CHF_2$ and $CH_2F$ or by one or more groups selected from among $OR^{2.1}$, $C_{1-3}$-alkylene-$OR^{2.1}$, $SR^{2.1}$, SO—$R^{2.1}$, $SO_2$—$R^{2.1}$, $COOR^{2.1}$, $COR^{2.1}$, methanol, ethanol, monocyclic $C_{3-7}$-cycloalkyl, phenyl, methyl, ethyl, propyl, isopropyl, phenyl-$C_{1-2}$-alkylene, hetaryl-$C_{1-2}$-alkylene, -het, -hetaryl and $NR^{2.2}R^{2.3}$, which in turn may optionally be substituted by one or more groups selected from among OH, $OR^{2.1}$, oxo, F, Cl, $CF_3$, $CHF_2$, $CH_2F$, methyl, ethyl, propyl, isopropyl, butyl, isobutyl, phenyl and $NR^{2.2}R^{2.3}$, and wherein $R^3$ is a naphthalene or phenyl, which may optionally be substituted in the ortho, para or meta position by one or two groups selected independently from among fluorine, chlorine, bromine, hydroxy, CN, methyl, ethyl, propyl, isopropyl, cyclopropyl, $CF_3$, $CHF_2$, $CH_2F$, —$OCH_3$, $OCH_2CH_3$; $SO_2$—$CH_3$, SO—$CH_3$, $COOCH_3$, $COOCH_2CH_3$, —CO—NH-(methylene)-hetaryl, —CO—NH-(ethylene)-hetaryl, —CO—NH-hetaryl, —CO—N($CH_3$)-het, —CO—N($CH_3$)— (methylene)-het, —CO—N($CH_3$)-(ethylene)-het, —CO—N($CH_3$)-(methylene)-hetaryl, —CO—N($CH_3$)-(ethylene)-hetaryl, —CO—N(cyclopropyl)-het, CO—$NH_2$, $CONH(CH_3)$, $CON(CH_3)_2$, —CO—NH-(methylene)-het, —CO—NH-(ethylene)-het, —NH—CO-methyl, $NCH_3$—CO-methyl, —NH—CO-ethyl, $NCH_3$—CO-ethyl, —NH—CO-propyl, $NCH_3$—CO-propyl, —NH—CO-isopropyl, $NCH_3$—CO-isopropyl, phenyl, phenyl-methylene, phenyl-ethylene, het-methylene, het-ethylene, -het, —CO-het, —CO—N($CH_3$)-het, CO—N($CH_3$)-cyclopropyl, $C_{3-7}$-cycloalkyl, $C_{3-7}$-cycloalkyl-methylene, $C_{3-7}$-cycloalkyl-ethylene, hetaryl-methylene, hetaryl-ethylene, -hetaryl, $CH_2$—$NH_2$, $CH_2$—$NH(CH_3)$, $CH_2$—$N(CH_3)_2$, —$NH_2$, —$NH(CH_3)$ and —$N(CH_3)_2$, wherein this group may optionally be substituted by one or more groups selected from among OH, F, Cl, —$CF_3$, $CHF_2$, $CH_2F$, oxo, methyl and phenyl or wherein $R^3$ denotes a group selected from among a het and hetaryl, which may optionally be substituted by one or more groups selected from among F, Cl, Br, $CF_3$, $CHF_2$, $CH_2F$, CN, OH, oxo, methyl, ethyl, propyl, isopropyl, butyl, isobutyl, cyclopropyl, —O-methyl, —O-ethyl, —O-propyl, —O-isopropyl, —COO-methyl, —COO-ethyl, —COO-propyl, —COO-isopropyl, SO—($CH_3$), SO—($CH_2$—$CH_3$), $SO_2$—($CH_3$), $SO_2$—($CH_2$—$CH_3$), phenyl, $CH_2$—$NH_2$, CH$_2$—NH(CH$_3$), CH$_2$—N(CH$_3$)$_2$, —NH$_2$, —NH(CH$_3$), —N(CH$_3$)$_2$, het and hetaryl, which in turn may optionally be substituted by one or more groups selected from among OH, F, Cl, CF$_3$, CHF$_2$, CH$_2$F, methyl, ethyl, propyl, isopropyl, phenyl, —COO-methyl, —COO-ethyl and O-methyl, O-ethyl, or wherein R$^3$ denotes —O—R$^{3.1}$, wherein R$^{3.1}$ is a group selected from among —C$_{1-3}$-alkyl, -phenyl, —C$_{1-3}$-alkylene-phenyl, hetaryl and het, which is optionally substituted in the ortho, para or meta position by one, two or three groups selected independently of one another from among fluorine, chlorine, bromine, hydroxy, CN, methyl, ethyl, propyl, isopropyl, butyl, isobutyl, CF$_3$, CHF$_2$, CH$_2$F, CO-(methyl), CO-(ethyl), CO-(propyl), CO-(isopropyl), —CO—(CF$_3$), —CO—NH-(methylene)-hetaryl, —CO—NH-(ethylene)-hetaryl, —CO—N(CH$_3$)-(methylene)-hetaryl, —CO—N(CH$_3$)-(ethylene)-hetaryl, —CO—N(CH$_3$)-(propylen)-hetaryl, —CO—N(CH$_3$)-(isopropylen)-hetaryl —CO—N(CH$_3$)-het, —CO—N(cyclopropyl)-het, —CO—N(C$_{5-7}$-cycloalkyl)-het, -methylene-O-methyl, -ethylene-O-methyl, -propylen-O-methyl, -methylene-O-ethyl, -ethylene-O-ethyl, -propylen-O-ethyl, -methylene-NH$_2$, -methylene-NHCH$_3$, -methylene-N(CH$_3$)$_2$, -ethylene-NH$_2$, -ethylene-NHCH$_3$, -ethylene-N(CH$_3$)$_2$, NH$_2$, N(CH$_3$)$_2$, NHCH$_3$, —O-methyl, O-ethyl, O-propyl, O-isopropyl, O-butyl, O-isobutyl, —SO—CH$_3$, SO-ethyl, —SO-propyl, —SO-isopropyl, SO$_2$-methyl, —SO$_2$-ethyl, SO$_2$-propyl, SO$_2$-isopropyl, COOH, COO-(methyl), COO-(ethyl), COO-(propyl), COO-(isopropyl), —O-methylene-N(methyl)$_2$, —O-ethylene-N(methyl)$_2$, —O-methylene-N(ethyl)$_2$, —O-ethylene-N(ethyl)$_2$, CO—NH$_2$, CO—NH(CH$_3$), CO—N(CH$_3$)$_2$, —NH—CO-methyl, —NCH$_3$—CO-methyl, —NH—CO-ethyl, NCH$_3$—CO-ethyl, phenyl, phenyl-methylene, phenyl-ethylene, het-methylene, het-ethylene, —CO-het, het, —CO—C$_{5-7}$-cycloalkyl, —CO-cyclopropyl, —CO—N(CH$_3$)—C$_{5-7}$-cycloalkyl, —CO—N(CH$_3$)-cyclopropyl, C$_{5-7}$-cycloalkyl, cyclopropyl, C$_{5-7}$-cycloalkyl-methylene, C$_{5-7}$-cycloalkyl-ethylene, cyclopropyl-methylene, cyclopropyl-ethylene, hetaryl-methylene, hetaryl-ethylene and hetaryl, which in turn may optionally be substituted by 1, 2, 3 or 4 groups selected independently of one another from among F, Cl, Br, methyl, O— methyl, ethyl, O-ethyl, OH, oxo and CF$_3$, and wherein R$^4$ denotes H, CN, OH, CF$_3$, CHF$_2$, CH$_2$F, F, methyl, ethyl, O-methyl or O-ethyl, -methylene-OH, -ethylene-OH, -propylene-OH, isopropylene-OH, —COO(methyl), —COO(ethyl), —COO(propyl), —COO(isopropyl), —CO-het, -(methylene)-NH—SO$_2$-(methyl), -(methylene)-NH—SO$_2$-(ethyl), -(ethylene)-NH—SO$_2$-(methyl), -(ethylene)-NH—SO$_2$-(ethyl), -(methylene)-N(CH$_3$)-SO$_2$-(methyl), -(methylene)-N(CH$_3$)-SO$_2$-(ethyl), -(ethylene)-N(CH$_3$)-SO$_2$-(methyl), -(ethylene)-N(CH$_3$)-SO$_2$-(ethyl), -(methylene)-O-(methylene)-phenyl, -(methylene)-O-(ethylene)-phenyl, -(ethylene)-O-(methylene)-phenyl, -(ethylene)-O-(ethylene)-phenyl, -methylene-O-methyl, -methylene-O-ethyl, -ethylene-O-methyl-ethylene-O-ethyl, -(methylene)-N(CH$_3$)—CO-(methyl), -(methylene)-N(CH$_3$)—CO-(ethyl) -(ethylene)-N(CH$_3$)—CO-(methyl), -(ethylene)-N(CH$_3$)—CO-(ethyl), —NH—CO-(methylene)-O-(methyl), —NH—CO-(methylene)-O-(ethyl), —NH—CO-(ethylene)-O-(methyl), —NH—CO-(ethylene)-O-(ethyl), -methylene-NH—CO-(methyl), -methylene-NH—CO-(ethyl), -ethylene-NH—CO-(methyl), -ethylene-NH—CO-(ethyl), -methylene-NH—CO-(methylene)-N(methyl)$_2$, -methylene-NH—CO-(ethylene)-N(methyl)$_2$, -ethylene-NH—CO-(methylene)-N(methyl)$_2$, -ethylene-NH—CO-(ethylene)-N(methyl)$_2$, -methylene-NH—CO-(methylene)-O-(methyl), -methylene-NH—CO-(ethylene)-O-(methyl), -ethylene-NH—CO-(methylene)-O-(methyl), -methylene-NH—CO-(methylene)-O-(ethyl), -methylene-NH—CO-(ethylene)-O-(ethyl), -ethylene-NH—CO-(methylene)-O-(ethyl), -(methylene)-N(CH$_3$)—CO-(methylene)-O-(methyl), -(methylene)-N(CH$_3$)—CO-(ethylene)-O-(methyl), -(ethylene)-N(CH$_3$)—CO-(ethylene)-O-(methyl), -(methylene)-N(CH$_3$)—CO-(methylene)-O-(ethyl), -(methylene)-N(CH$_3$)—CO-(ethylene)-O-(ethyl), -(ethylene)-N(CH$_3$)—CO-(methylene)-O-(ethyl), —O-(methylene)-phenyl, —O-(ethylene)-phenyl, —CO-phenyl, wherein the phenyl in the above groups may optionally be substituted by one or more other groups selected from among F, Cl, Br, methyl, ethyl, propyl, —O-methyl, —O-ethyl, —O-propyl, —OH and CF$_3$ or wherein R$^3$ and R$^4$ together form a mono- or bicyclic, unsaturated, saturated or partly saturated heterocyclic group which contains 1, 2 or 3 heteroatoms selected from among N, O and S and which may optionally be substituted by one or more groups selected from among F, Cl, Br, OH, oxo, CF$_3$, CHF$_2$, CH$_2$F, CN, methyl, ethyl, propyl, isopropyl, cyclopropyl, COO-methyl, —COO-ethyl, O-methyl, O-ethyl, SO$_2$—(CH$_3$), SO$_2$—(CH$_2$CH$_3$), SO—(CH$_3$), SO—(CH$_2$CH$_3$), CH$_2$—NH$_2$, CH$_2$—NH(CH$_3$), CH$_2$—N(CH$_3$)$_2$, —NH$_2$, —NH(CH$_3$), —N(CH$_3$)$_2$, phenyl, C$_{3-7}$-cycloalkyl, het and hetaryl, contain at least one NSAID (2).

Also particularly preferred are the above drug combinations which, in addition to one or more, preferably one compound of formula 1 as PDE4 inhibitor, wherein R$^2$ is a group according to formula 3

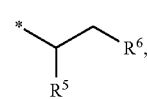

3 wherein R$^6$ is OH or NH$_2$ and wherein R$^5$ denotes a group selected from among C$_{1-4}$-alkyl, a five- to six-membered heteroaryl with 1, 2 or 3 heteroatoms from the group S, O and N and phenyl, which may optionally be substituted by one or more groups selected from among OH, F, Br, OR$^{2.1}$, oxo, methyl, ethyl, methanol, ethanol, phenyl, COOR$^{2.1}$, CH$_2$—NR$^{2.2}$R$^{2.3}$ and NR$^{2.2}$R$^{2.3}$ and wherein the other groups are as hereinbefore defined, contain at least one NSAID (2).

Also particularly preferred are the above mentioned drug combinations which, in addition to one or more, preferably one compound of formula 1 as PDE4 inhibitor, wherein $R^2$ is a group according to formula 3

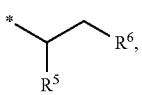

wherein $R^6$ is OH or $NH_2$ and
wherein $R^5$ denotes methyl, ethyl, propyl, isopropyl,
contain at least one NSAID (2).

In another particularly preferred aspect the invention relates to the above drug combinations which, in addition to one or more, preferably one compound of formula 1 as PDE4 inhibitor, wherein
$R^2$ is a monocyclic three-, four-, five-, six- or seven-membered cycloalkyl ring which may optionally be substituted in the spiro position by a group selected from among —$CH_2$—$OR^{2.1}$, branched or unbranched $C_{2-6}$-alkylene-$OR^{2.1}$, methyl, ethyl, propyl, isopropyl, butyl, isobutyl, cyclopropyl, —$CF_3$, $CHF_2$, $CH_2F$ and $C_{2-4}$-fluoroalkyl, wherein
$R^{2.1}$ is selected from among methyl, ethyl, propyl, isopropyl, butyl, isobutyl, and wherein the other groups are as hereinbefore defined,
contain at least one NSAID (2).

Also particularly preferred are those of the above drug combinations which, in addition to one or more, preferably one compound of formula 1 as PDE4 inhibitor, wherein
$R^2$ is a cyclopropyl which may optionally be substituted by another group selected from among —$NH_2$, $CH2$-$NH_2$, —$NH(CH_3)$, —$N(CH_3)_2$, methyl, ethyl, propyl, isopropyl, —NH—CO-(tert-butyl), —NH—CO—O-(tert-butyl), —N($CH_3$)—CO-(tert-butyl), —N($CH_3$)—CO—O-(tert-butyl), —$CF_3$, —$CHF_2$, $CH_2F$, F, Cl and Br,
and wherein the other groups are as hereinbefore defined,
contain at least one NSAID (2).

Other particularly preferred ones of the above drug combinations are those which, in addition to one or more, preferably one compound of formula 1 as PDE4 inhibitor, wherein
$R^2$ denotes a cyclopropyl
$R^2$ is a phenyl which may optionally be substituted in one or both meta positions by one or more groups selected from among methyl, ethyl, propyl, isopropyl, cyclopropyl, F, Cl, Br, OH, $OR^{2.1}$, $COOR^{2.1}$, $CF_3$, $CHF_2$, $CH_2F$, $NH_2$, $NH(CH_3)$ and $N(CH_3)_2$,
wherein $R^{2.1}$ may be H, methyl or ethyl,
and wherein the other groups are as hereinbefore defined,
contain at least one NSAID (2).

In another particularly preferred aspect the invention relates to those of the above drug combinations which, in addition to one or more, preferably one compound of formula 1 as PDE4 inhibitor, wherein
$R^2$ denotes a group selected from among monocyclic, saturated three-, four-, five-, six- or seven-membered heterocyclic groups with 1, 2 or 3 heteroatoms selected in each case from among N, O and S, which may optionally be substituted by one or more groups selected from among fluorine, chlorine, bromine, $CF_3$, $CHF_2$, $CH_2F$, OH and oxo or by one or more groups selected from among $OR^{2.1}$, $C_{1-3}$-alkylene-$OR^{2.1}$, $SR^{2.1}$, SO—$R^{2.1}$, $SO_2$—$R^{2.1}$, $COOR^{2.1}$, $COR^{2.1}$, $C_{1-6}$-alkanol, $C_{3-10}$-cycloalkyl, phenyl, $C_{1-6}$-alkyl, phenyl-$C_{1-6}$-alkylene, hetaryl-$C_{1-6}$-alkylene, het, hetaryl and $NR^{2.2}R^{2.3}$, which in turn may optionally be substituted by one or more groups selected from among OH, $OR^{2.1}$, oxo, F, Cl, $CF_3$, $CHF_2$, $CH_2F$, $C_{1-6}$-alkyl, phenyl and $NR^{2.2}R^{2.3}$,
and
wherein $R^{2.1}$, $R^{2.2}$ and $R^{2.3}$ are as hereinbefore defined, contain at least one NSAID (2).

Also particularly preferred are those drug combinations which, in addition to one or more, preferably one compound of formula 1 as PDE4 inhibitor,
wherein
$R^2$ denotes a group selected from among a monocyclic, saturated six-membered heterocyclic group with a heteroatom selected from among N, O and S, which may optionally be substituted by one or more groups selected from among F, Cl, Br, $CF_3$, $CHF_2$, $CH_2F$, OH, oxo, $NH_2$, $NHCH_3$ and $N(CH_3)_2$, methyl, ethyl, propyl, isopropyl, cyclopropyl, methoxy and ethoxy,
and wherein the other groups are as hereinbefore defined, contain at least one NSAID (2).

In another particularly preferred aspect the present invention relates to the above-mentioned drug combination which, in addition to one or more, preferably one compound of formula 1 as PDE4 inhibitor,
wherein
$R^2$ is a group selected from among piperidine or tetrahydropyran, which may optionally be substituted by one or more groups selected from among F, Cl, Br, OH, $CF_3$, $CHF_2$, $CH_2F$, $NH_2$, $NHCH_3$, $N(CH_3)_2$, oxo, methyl and methoxy,
and wherein the other groups are as hereinbefore defined, contains at least one NSAID (2).

Also particularly preferred are the above drug combinations which, in addition to one or more, preferably one compound of formula 1 as PDE4 inhibitor,
wherein
$R^3$ denotes a naphthalene or phenyl,
which may optionally be substituted in any desired position by one, two or three groups selected independently from among fluorine, chlorine, bromine, hydroxy, CN, methyl, ethyl, propyl, isopropyl, cyclopropyl, $CF_3$, $CHF_2$, $CH_2F$, —$OCH_3$, $OCH_2CH_3$; $SO_2$—$CH_3$, $SO_2$—$CH_2CH_3$, $COOCH_3$ and CO—O—$CH_2CH_3$,
and wherein the above groups are as hereinbefore defined, contain at least one NSAID (2).

Also particularly preferred within the scope of the invention are the above drug combinations which, in addition to one or more, preferably one compound of formula 1 as PDE4 inhibitor, wherein
$R^3$ denotes a group selected from among het and hetaryl, which may optionally be substituted by one or more groups selected from among F, Cl, Br, $CF_3$, $CHF_2$, $CH_2F$, CN, OH, oxo, methyl, ethyl, propyl, isopropyl, butyl, isobutyl, cyclopropyl, $C_{5-7}$-cycloalkyl, —O-methyl, —O-ethyl, —O-propyl, —O-isopropyl, —COO-methyl, —COO-ethyl, —COO-propyl, —COO-isopropyl, $SO_2$—($CH_3$), $SO_2$—($CH_2$—$CH_3$), SO—($CH_3$), SO—($CH_2$—$CH_3$), phenyl, —$CH_2$—$NH_2$, —$CH_2$—$NHCH_3$, —$CH_2$—N($CH_3$)$_2$, $NH_2$, $NHCH_3$, $N(CH_3)_2$, het and hetaryl, which in turn may be substituted with one or more groups selected from among OH, F, Cl, Br, $CF_3$, $CHF_2$, $CH_2F$, methyl, ethyl, propyl, isopropyl, phenyl, —COO-methyl, —COO-ethyl, —COO-propyl, —COO-isopropyl and O-methyl, O-ethyl, O-propyl and O-isopropyl,
and wherein
$R^4$ denotes H, CN, OH, $CF_3$, $CHF_2$, $CH_2F$, F, methyl, ethyl, O-methyl or O-ethyl,
and wherein
het denotes a three- to seven-membered, monocyclic, saturated or partly saturated heterocyclic group or a seven- to eleven-membered, bicyclic, anellated, saturated or partly saturated heterocyclic group which contains 1, 2 or 3 heteroatoms selected
independently of one another from among N, S or O,
and wherein
hetaryl is a five- to six-membered, monocyclic, aromatic heteroaryl or a seven- to eleven-membered, bicyclic, anellated, aromatic heteroaryl which contains in each case 1, 2 or 3 heteroatoms selected independently from among N, S or O,
and wherein
cycloalkyl may be saturated or partly saturated,
contain at least one NSAID (2).

Also particularly preferred are the above drug combinations, characterised in that, in addition to one or more, preferably one compound of formula 1 as PDE4 inhibitor, wherein
$R^3$ is a group selected from a bicyclic, seven- to eleven-membered, saturated or partly saturated heterocyclic group or a bicyclic, seven- to eleven-membered heteroaryl, which is selected from among indole, dihydroindole, quinazoline, dihydroquinazoline, tetrahydroquinazoline, benzoisoxazole, dihydrobenzoisoxazole, benzoxazine, dihydrobenzoxazine, benzothiazole, dihydrobenzothiazole, triazolopyridine, dihydrotriazolopyridine, benzofuran, dihydrobenzofuran, isobenzofuran and dihydroisobenzofuran,
which may optionally be substituted by one or more groups selected from among F, Cl, Br, $CF_3$, $CHF_2$, $CH_2F$, CN, OH, oxo, methyl, ethyl, propyl, isopropyl, butyl, isobutyl, cyclopropyl, —O-methyl, —O-ethyl, —O-propyl, —O-isopropyl, —COO-methyl, —COO-ethyl, —COO-propyl, —COO-isopropyl, $SO_2$—$(CH_3)$, $SO_2$—$(CH_2$—$CH_3)$, SO—$(CH_3)$, SO—$(CH_2$—$CH_3)$, phenyl, —$CH_2$—$NH_2$, —$CH_2$—$NHCH_3$, —$CH_2$—N$(CH_3)_2$, $NH_2$, $NHCH_3$, $N(CH_3)_2$, furanyl and pyridinyl,
which in turn may be substituted by one or more groups selected from among OH, F, Cl, Br, $CF_3$, $CHF_2$, $CH_2F$, methyl, ethyl, propyl, isopropyl, phenyl, —COO-methyl, —COO-ethyl and O-methyl, O-ethyl,
and wherein the other groups are as hereinbefore defined,
they contain at least one NSAID (2).

Also particularly preferred are the above drug combinations which, in addition to one or more, preferably one compound of formula 1 as PDE4-inhibitors, wherein
$R^3$ is a group selected from a monocyclic, saturated or partly saturated, three- to seven-membered heterocyclic group or a monocyclic five- to six-membered heteroaryl,
which is selected from among imidazole, dihydroimidazole, oxadiazole, oxadiazolidine, pyrazole, pyridine and dihydropyrazole,
which may optionally be substituted by one or more groups selected from among F, Cl, Br, $CF_3$, $CHF_2$, $CH_2F$, CN, OH, oxo, methyl, ethyl, propyl, isopropyl, butyl, isobutyl, cyclopropyl, —O-methyl, —O-ethyl, —O-propyl, —O-isopropyl, —COO-methyl, —COO-ethyl, —COO-propyl, —COO-isopropyl, $SO_2$—$(CH_3)$, $SO_2$—$(CH_2$—$CH_3)$, SO—$(CH_3)$, SO—$(CH_2$—$CH_3)$, phenyl, —$CH_2$—$NH_2$, —$CH_2$—$NHCH_3$, —$CH_2$—N$(CH_3)_2$, $NH_2$, $NHCH_3$, $N(CH_3)_2$, furanyl and pyridinyl,
which in turn may be substituted by one or more groups selected from among OH, F, Cl, Br, $CF_3$, $CHF_2$, $CH_2F$, methyl, ethyl, propyl, isopropyl, phenyl, —COO-methyl, —COO-ethyl and O-methyl, O-ethyl,
and wherein the other groups are as hereinbefore defined,
contain at least one NSAID (2).

In a particularly preferred aspect the present invention relates to the above drug combinations which, in addition to one or more, preferably one compound of formula 1 as PDE4 inhibitor, wherein
$R^3$ and $R^4$ together form a mono- or bicyclic, unsaturated or partly saturated, three- to eleven-membered heterocyclic group which contains 1, 2 or 3 heteroatoms selected from among N, O and S and which may optionally be substituted by one or more groups selected from among F, Cl, Br, OH, oxo, $CF_3$, $CHF_2$, $CH_2F$, CN, methyl, ethyl, propyl, isopropyl, cyclopropyl, COO-methyl, —COO-ethyl, O-methyl, O-ethyl, $SO_2$—$(CH_3)$, $SO_2$—$(CH_2$—$CH_3)$, SO—$(CH_3)$, SO—$(CH_2$—$CH_3)$, phenyl, —$CH_2$—$NH_2$, —$CH_2NHCH_3$, —$CH_2$—N$(CH_3)_2$, $NH_2$, $NHCH_3$, $N(CH_3)_2$, a saturated or partly saturated, five- to six-membered heterocyclic group and a five- to six-membered heteroaryl,
and wherein the other groups are as hereinbefore defined,
contain at least one NSAID (2).

Also particularly preferred are the above drug combinations which, in addition to one or more, preferably one compound of formula 1 as PDE4-inhibitor, wherein
$R^3$ and $R^4$ together form a bicyclic heterocyclic group selected from among
tetrahydroquinazoline, tetrahydrobenzoxazine and dihydroindole, dihydroisobenzofuran which may optionally be substituted by one or more groups selected from among F, Cl, Br, OH, oxo, $CF_3$, $CHF_2$, $CH_2F$, CN, methyl, ethyl, propyl, isopropyl, cyclopropyl, COO-methyl, —COO-ethyl, O-methyl, O-ethyl, $SO_2$—$(CH_3)$, $SO_2$—$(CH_2$—$CH_3)$, phenyl, —$CH_2$—$NH_2$, —$CH_2NHCH_3$, —$CH_2$—N$(CH_3)_2$, $NH_2$, $NHCH_3$, $N(CH_3)_2$, a saturated or partly saturated, five or six-membered heterocyclic group and a five or six-membered heteroaryl, and wherein the other groups are as hereinbefore defined,
contain at least one NSAID (2).

Moreover, of the above mentioned drug combinations, particularly preferred ones within the scope of the invention are those which contain, in addition to one or more, preferably one compound of formula 1 as PDE4 inhibitor,
wherein
$R^3$ is —O—$R^{3.1}$,
$R^{3.1}$ is a group selected from among methyl, ethyl, propyl, isopropyl, butyl, isobutyl, pentyl, isopentyl, -phenyl, -methylene-phenyl, -ethylene-phenyl, -propylene-phenyl, -isopropylene-phenyl, hetaryl and het,
which may optionally be substituted in the ortho, para or meta position by one, two or three groups selected independently of one another from among fluorine, chlorine, bromine, hydroxy, CN, methyl, ethyl, propyl, isopropyl, butyl, isobutyl, —$CF_3$, $CHF_2$, $CH_2F$, CO-(methyl), CO-(ethyl),
CO-(propyl), CO-(isopropyl), CO-(butyl), CO-(isobutyl), —CO—$(CF_3)$, —CO—$(CH_2F)$, —CO—$(CHF_2)$, —CO—NH-(methylene)-hetaryl, —CO—NH-(ethylene)-hetaryl, —CO—NH-(propylene)-hetaryl, —CO—NH-(isopropylene)-hetaryl,
—CO—N$(CH_3)$-(methylene)-hetaryl, —CO—N$(CH_3)$-(ethylene)-hetaryl, —CO—N$(CH_3)$-(propylene)-hetaryl, —CO—N$(CH_3)$-(isopropylene)-hetaryl, —CO—N$(CH_3)$-het, —CO—N$(C_{3-7}$-cycloalkyl)-het, -methylene-O-methyl, -ethylene-O-methyl, -methylene-O-ethyl, -ethylene-O-ethyl, -methylene-$NH_2$, -ethylene-$NH_2$, -methylene-$NHCH_3$, -ethylene-$NHCH_3$, -methylene-N$(CH_3)_2$, -ethylene-N$(CH_3)_2$, —$NH_2$, —$NHCH_3$, —N$(CH_3)_2$, —O-methyl, —O-ethyl, —O- propyl, —O-isopropyl, —SO—CH$_3$, —SO—(CH$_2$CH$_3$), —SO$_2$—CH$_3$, —SO$_2$—(CH$_2$CH$_3$), COOH, COO-(methyl), COO-(ethyl), COO-(propyl), COO-(isopropyl), —O-methylene-N(methyl)$_2$, —O-ethylene-N(methyl)$_2$, —O-methylene-N(ethyl)$_2$, —O-ethylene-N(ethyl)$_2$, CO—NH$_2$, CO—NHCH$_3$, CO—N(CH$_3$)$_2$, NH—CO-methyl, NCH$_3$—CO-methyl, NH—CO-ethyl, N(CH$_3$)—CO-ethyl, phenyl, phenyl-methylene, phenyl-ethylene, het-methylene, het-ethylene, —CO-het, het, —CO—C$_{4-7}$-cycloalkyl, —CO-cyclopropyl, —CO—N(CH$_3$)-cyclopropyl, —CO—N(CH$_3$)—C$_{4-7}$-cycloalkyl, C$_{4-7}$-cycloalkyl, cyclopropyl, C$_{4-7}$-cycloalkyl-methylene, cyclopropyl-methylene, C$_{4-7}$-cycloalkyl-ethylene, cyclopropyl-ethylene, hetaryl-methylene, hetaryl-ethylene and hetaryl, which in turn may optionally be substituted by 1, 2, 3 or 4 groups selected independently of one another from among F, Cl, Br, methyl, O-methyl, ethyl, O-ethyl, OH, oxo and CF$_3$, and wherein the other groups are as hereinbefore defined, at least one NSAID (2).

In another particularly preferred aspect the invention relates to the above-mentioned drug combinations, characterised in that in addition to one or more, preferably one compound of formula 1 as PDE4 inhibitor, wherein R$^4$ denotes H, CN, OH, CF$_3$, CHF$_2$, CH$_2$F, F, methyl, ethyl, O-methyl or O-ethyl, -methylene-OH, -ethylene-OH, -propylene-OH, isopropylene-OH, —COO(methyl), —COO(ethyl), —COO(propyl), —COO(isopropyl), —CO-het, -(methylene)-NH—SO$_2$-(methyl), -(methylene)-NH—SO$_2$-(ethyl), -(ethylene)-NH—SO$_2$-(methyl), -(ethylene)-NH—SO$_2$-(ethyl), -(methylene)-N(CH$_3$)—SO$_2$-(methyl), -(methylene)-N(CH$_3$)—SO$_2$-(ethyl), -(ethylene)-N(CH$_3$)—SO$_2$-(methyl), -(ethylene)-N(CH$_3$)—SO$_2$-(ethyl), -(methylene)-O-(methylene)-phenyl, -(methylene)-O-(ethylene)-phenyl, -(ethylene)-O-(methylene)-phenyl, -(ethylene)-O-(ethylene)-phenyl, -methylene-O-methyl, -methylene-O-ethyl, -ethylene-O-methyl -ethylene-O-ethyl, -(methylene)-N(CH$_3$)—CO-(methyl), -(methylene)-N(CH$_3$)—CO-(ethyl) -(ethylene)-N(CH$_3$)—CO-(methyl), -(ethylene)-N(CH$_3$)—CO-(ethyl), —NH—CO-(methylene)-O-(methyl), —NH—CO-(methylene)-O-(ethyl), —NH—CO-(ethylene)-O-(methyl), —NH—CO-(ethylene)-O-(ethyl), -methylene-NH—CO-(methyl), -methylene-NH—CO-(ethyl), -ethylene-NH—CO-(methyl), -ethylene-NH—CO-(ethyl), -methylene-NH—CO-(methylene)-N(methyl)$_2$, -methylene-NH—CO-(ethylene)-N(methyl)$_2$, -ethylene-NH—CO-(methylene)-N(methyl)$_2$, -ethylene-NH—CO-(ethylene)-N(methyl)$_2$, -methylene-NH—CO-(methylene)-O-(methyl), -methylene-NH—CO-(ethylene)-O-(methyl), -ethylene-NH—CO-(methylene)-O-(methyl), -ethylene-NH—CO-(ethylene)-O-(ethyl), -ethylene-NH—CO-(methylene)-O-(ethyl), -(methylene)-N(CH$_3$)—CO-(methylene)-O-(methyl), -(methylene)-N(CH$_3$)—CO-(ethylene)-O-(methyl), -(ethylene)-N(CH$_3$)—CO-(methylene)-O-(methyl), -(methylene)-N(CH$_3$)—CO-(methylene)-O-(ethyl), -(methylene)-N(CH$_3$)—CO-(ethylene)-O-(ethyl), -(ethylene)-N(CH$_3$)—CO-(methylene)-O-(ethyl), —O-(methylene)-phenyl, —O-(ethylene)-phenyl, —CO-phenyl, wherein the phenyl in the above groups may optionally be substituted by one or more other groups selected from among F, Cl, Br, methyl, ethyl, propyl, —O-methyl, —O-ethyl, —O-propyl, —OH and CF$_3$, and wherein the other groups are as hereinbefore defined, they contain at least one NSAID (2).

Also particularly preferred are the above drug combinations which, in addition to one or more, preferably one compound of formula 1 as PDE4 inhibitor, wherein R$^3$ denotes a group selected from among oxazole, imidazole and thiazole, wherein this group may optionally be substituted by one, two or three further groups selected independently from among methyl, ethyl, propyl, isopropyl, O-methyl, O-ethyl, O-propyl, O-isopropyl, OH, F, Cl, Br, CF$_3$, phenyl, hetaryl and C$_{3-6}$-cycloalkyl, and wherein the other groups are as hereinbefore defined, contain at least one NSAID (2).

Within the scope of the present invention particularly preferred among the above mentioned drug combinations are those which, in addition to one or more, preferably one compound of formula 1 as PDE4 inhibitor, wherein X is SO$_2$, contain at least one NSAID (2).

Also particularly preferred are the above drug combinations which contain, in addition to one or more, preferably one compound of formula 1 as PDE4 inhibitor selected from among:

1.1 (R)-2-{2-[4-(4-chlorophenyl)-piperidin-1-yl]-5-oxo-6,7-dihydro-5H-5λ4-thieno[3,2-d]pyrimidin-4-ylamino}-3-methylbutan-1-ol 1.2 (1-{2-[4-(4-chlorophenyl)-piperidin-1-yl]-5-oxo-6,7-dihydro-5H-5λ4-thieno[3,2-d]pyrimidin-4-ylamino}-cyclopropyl)-methanol 1.3 (R)-2-{2-[4-(4-chlorophenyl)-piperidin-1-yl]-5-oxo-6,7-dihydro-5H-5λ4-thieno[3,2-d]pyrimidin-4-ylamino}-pentan-1-ol 1.4 (R)-1-{2-[4-(4-chlorophenyl)-piperidin-1-yl]-5-oxo-6,7-dihydro-5H-5λ4-thieno[3,2-d]pyrimidin-4-ylamino}-1-(4-fluorophenyl)-2-methylpropan-2-ol 1.5 (S)-5-{2-[4-(4-chlorophenyl)-piperidin-1-yl]-5-oxo-6,7-dihydro-5H-5λ4-thieno[3,2-d]pyrimidin-4-ylamino}-1-methylpiperidin-2-one 1.6 {2-[4-(4-chlorophenyl)-piperidin-1-yl]-5-oxo-6,7-dihydro-5H-5λ4-thieno[3,2-d]pyrimidin-4-yl}-(tetrahydropyran-4-yl)-amine 1.7 1-(4-(1-hydroxymethylcyclopropylamino)-5-oxo-6,7-dihydro-5H-5λ4-thieno[3,2-d]pyrimidin-2-yl)-3'-methyl-1'H-spiro[piperidin-4,4'-quinazolin]-2'(3'H)-one 1.8 {1-[2-(4-benzo[d]isoxazol-3-yl-piperidin-1-yl)-5-oxo-6,7-dihydro-5H-5λ4-thieno[3,2-d]pyrimidin-4-ylamino]-cyclopropyl}-methanol 1.9 (1-{2-[4-(2-ethyl-5-fluoro-1H-indol-3-yl)-piperidin-1-yl]-5-oxo-6,7-dihydro-5H-5λ4-thieno[3,2-d]pyrimidin-4-ylamino}-cyclopropyl)-methanol 1.10 1-[4-((S)-1-methyl-6-oxopiperidin-3-ylamino)-5-oxo-6,7-dihydro-5H-5λ4-thieno[3,2-d]pyrimidin-2-yl]-4-phenylpiperidin-4-carbonitrile 1.11 3'-methyl-1-(4-(tetrahydro-2H-pyran-4-ylamino)-5-oxo-6,7-dihydro-5H-5λ4-thieno[3,2-d]pyrimidin-2-yl)-1'H-spiro[piperidin-4,4'-quinazolin]-2'(3'H)-one 1.12 (3-fluorophenyl)-[5-oxo-2-(3,4,5,6-tetrahydro-2H-[4,4]bipyridinyl-1-yl)-6,7-dihydro-5H-5λ4-thieno[3,2-d]pyrimidin-4-yl]-amine 1.13 {2-[4-(2-ethyl-5-fluoro-1H-indol-3-yl)-piperidin-1-yl]-5-oxo-6,7-dihydro-5H-5λ4-thieno[3,2-d]pyrimidin-4-yl}-(3-fluorophenyl)-amine 1.14 (1-{2-[4-(2,4-difluorophenyl)-piperidin-1-yl]-5-oxo-6,7-dihydro-5H-5λ4-thieno[3,2-d]pyrimidin-4-ylamino}-cyclopropyl)-methanol 1.15 {2-[4-(2,4-difluorophenyl)-piperidin-1-yl]-5-oxo-6,7-dihydro-5H-5λ4-thieno[3,2-d]pyrimidin-4-yl}-(tetrahydropyran-4-yl)-amine 1.16 (S)-5-[2-(4-benzoxazol-2-yl-piperidin-1-yl)-5-oxo-6,7-dihydro-5H-5λ4-thieno[3,2-d]pyrimidin-4-ylamino]-1-methylpiperidin-2-one 1.17 (1-{2-[4-(6-fluorobenzo[d]isoxazol-3-yl)-piperidin-1-yl]-5-oxo-6,7-dihydro-5H-5λ4-thieno[3,2-d]pyrimidin-4-ylamino}-cyclopropyl)-methanol 1.18 (1-{2-[4-(5-fluorobenzo[d]isoxazol-3-yl)-piperidin-1-yl]-5-oxo-6,7-dihydro-5H-5λ4-thieno[3,2-d]pyrimidin-4-ylamino}-cyclopropyl)-methanol 1.19 {2-[4-(5-furan-2-yl-2H-pyrazol-3-yl)-piperidin-1-yl]-5-oxo-6,7-dihydro-5H-5λ4-thieno[3,2-d]pyrimidin-4-yl}-(tetrahydropyran-4-yl)-amine 1.20 (3-fluorophenyl)-{5-oxo-2-[4-(3-pyridin-4-yl-[1,2,4]oxadiazol-5-yl)-piperidin-1-yl]-6,7-dihydro-5H-5λ4-thieno[3,2-d]pyrimidin-4-yl}-amine 1.21 (R)-3-methyl-2-{5-oxo-2-[4-(3-pyridin-4-yl-[1,2,4]oxadiazol-5-yl)-piperidin-1-yl]-6,7-dihydro-5H-5λ4-thieno[3,2-d]pyrimidin-4-ylamino}-butan-1-ol 1.22 (S)-5-{2-[4-(4-fluorophenoxy)-piperidin-1-yl]-5-oxo-6,7-dihydro-5H-5λ4-thieno[3,2-d]pyrimidin-4-ylamino}-1-methylpiperidin-2-one 1.23 (2-{4-[4-(4,5-dihydrooxazol-2-yl)-phenoxy]-piperidin-1-yl}-5-oxo-6,7-dihydro-5H-5λ4-thieno[3,2-d]pyrimidin-4-yl)-(tetrahydropyran-4-yl)-amine 1.24 4-{1-[5-oxo-4-(tetrahydropyran-4-ylamino)-6,7-dihydro-5H-5λ4-thieno[3,2-d]pyrimidin-2-yl]-piperidin-4-yloxy}-benzoic acid 1.25 2-(1-{2-[4-(4-chlorophenyl)-piperidin-1-yl]-5-oxo-6,7-dihydro-5H-5λ4-thieno[3,2-d]pyrimidin-4-ylamino}-cyclopropyl)-propan-2-ol 1.26 {2-[4-(5-tert-butyl-1-methyl-1H-indol-3-yl)-piperidin-1-yl]-5-oxo-6,7-dihydro-5H-5λ4-thieno[3,2-d]pyrimidin-4-yl}-(tetrahydropyran-4-yl)-amine 1.27 2-[4-(5-furan-2-yl-1-methyl-1H-pyrazol-3-yl)-piperidin-1-yl]-5-oxo-6,7-dihydro-5H-5λ4-thieno[3,2-d]pyrimidin-4-yl)-(tetrahydropyran-4-yl)-amine 1.28 (S)-5-(2-{4-[4-(4,5-dihydrooxazol-2-yl)-phenoxy]-piperidin-1-yl}-5-oxo-6,7-dihydro-5H-5λ4-thieno[3,2-d]pyrimidin-4-ylamino)-1-methylpiperidin-2-one 1.29 {2-[4-(5-furan-2-yl-2-methyl-2H-pyrazol-3-yl)-piperidin-1-yl]-5-oxo-6,7-dihydro-5H-5λ4-thieno[3,2-d]pyrimidin-4-yl}-(tetrahydropyran-4-yl)-amine 1.30 {2-[4-(1-methyl-1H-imidazo[4,5-c]pyridin-2-yl)-piperidin-1-yl]-5-oxo-6,7-dihydro-5H-5λ4-thieno[3,2-d]pyrimidin-4-yl}-(tetrahydropyran-4-yl)-amine 1.31 2-methoxy-N-{1-[5-oxo-4-(tetrahydropyran-4-ylamino)-6,7-dihydro-5H-5λ4-thieno[3,2-d]pyrimidin-2-yl]-4-phenylpiperidin-4-ylmethyl}-acetamide 1.32 N-cyclopropyl-N-methyl-4-{1-[5-oxo-4-(tetrahydropyran-4-ylamino)-6,7-dihydro-5H-5λ4-thieno[3,2-d]pyrimidin-2-yl]-piperidin-4-yl}-benzamide 1.33 N-cyclopropyl-N-methyl-4-{1-[5-oxo-4-(tetrahydropyran-4-ylamino)-6,7-dihydro-5H-5λ4-thieno[3,2-d]pyrimidin-2-yl]-piperidin-4-yloxy}-benzamide 1.34 (5-oxo-2-[4-(pyridin-4-yloxy)-piperidin-1-yl]-6,7-dihydro-5H-5λ4-thieno[3,2-d]pyrimidin-4-yl)-(tetrahydropyran-4-yl)-amine 1.35 {2-[4-(4-chlorophenoxy)-piperidin-1-yl]-5-oxo-6,7-dihydro-5H-5λ4-thieno[3,2-d]pyrimidin-4-yl}-(tetrahydropyran-4-yl)-amine 1.36 (S)-1-methyl-5-{2-[4-(5-methyl-4-phenyloxazol-2-yl)-piperidin-1-yl]-5-oxo-6,7-dihydro-5H-5λ4-thieno[3,2-d]pyrimidin-4-ylamino}-piperidin-2-one 1.37 (1-{2-[4-(5-methyl-4-phenyloxazol-2-yl)-piperidin-1-yl]-5-oxo-6,7-dihydro-5H-5λ4-thieno[3,2-d]pyrimidin-4-ylamino}-cyclopropyl)-methanol 1.38 (S)-5-{2-[4-(4,5-diphenyloxazol-2-yl)-piperidin-1-yl]-5-oxo-6,7-dihydro-5H-5λ4-thieno[3,2-d]pyrimidin-4-ylamino}-1-methylpiperidin-2-one 1.39 {4-(4-chlorophenyl)-1-[5-oxo-4-(tetrahydropyran-4-ylamino)-6,7-dihydro-5H-5λ4-thieno[3,2-d]pyrimidin-2-yl]-piperidin-4-yl}-methanol 1.40 [1-(2-{4-[5-(4-chlorophenyl)-4-methyloxazol-2-yl]-piperidin-1-yl}-5-oxo-6,7-dihydro-5H-5λ4-thieno[3,2-d]pyrimidin-4-ylamino)-cyclopropyl]-methanol 1.41 4-(4-chlorophenyl)-1-[5-oxo-4-(tetrahydropyran-4-ylamino)-6,7-dihydro-5H-5λ4-thieno[3,2-d]pyrimidin-2-yl]-piperidin-4-ol 1.42 {2-[4-(4-chlorophenyl)-4-methoxypiperidin-1-yl]-5-oxo-6,7-dihydro-5H-5λ4-thieno[3,2-d]pyrimidin-4-yl}-(tetrahydropyran-4-yl)-amine 1.43 4-{1-[4-(1-hydroxymethylcyclopropylamino)-5-oxo-6,7-dihydro-5H-5λ4-thieno[3,2-d]pyrimidin-2-yl]-piperidin-4-yloxy}-benzonitrile 1.44 5-oxo-2-[4-(4,5,6,7-tetrahydrobenzoxazol-2-yl)-piperidin-1-yl]-6,7-dihydro-5H-5λ4-thieno[3,2-d]pyrimidin-4-yl)-(tetrahydropyran-4-yl)-amine 1.45 (S)-5-{2-[4-(4-chlorophenyl)-piperidin-1-yl]-5,5-dioxo-6,7-dihydro-5H-5λ6-thieno[3,2-d]pyrimidin-4-ylamino}-1-methylpiperidin-2-one contain at least one NSAID (2).

The above mentioned compounds of formula 1 are prepared as described in detail in the synthesis instructions.

Also particularly preferred are the above drug combinations which contain at least one NSAID (2) selected from COX 1-inhibitors or COX 2-inhibitors, in addition to the one or more, preferably one, compound of general formula 1 as PDE4 inhibitor.

In a particularly preferred aspect the invention relates to the above drug combinations which contain, in addition to one or more, preferably one compound of general formula 1 as PDE4 inhibitor, at least one NSAID (2) selected from among aceclofenac (2.1), acemetacin (2.2), acetylsalicylic acid (2.3), alclofenac (2.4), alminoprofen (2.5), amfenac (2.6), ampiroxicam (2.7), antolmetinguacil (2.8), anirolac (2.9), antrafenine (2.10), azapropazone (2.11), benorilate (2.12), bermoprofen (2.13), bindarit (2.14), bromfenac (2.15), bucloxinic acid (2.16), bucolom (2.17), bufexamac (2.18), bumadizone (2.19), butibufen (2.20), butixirate (2.21), carbasalate calcium (2.22), carprofen (2.23), choline magnesium trisalicylate (2.24), celecoxib (2.25), cinmetacin (2.26), cinnoxicam (2.27), clidanac (2.28), clobuzarit (2.29), deboxamet (2.30), dexibuprofen (2.31), dexketoprofen (2.32), diclofenac (2.33), diflunisal (2.34), droxicam (2.35), eltenac (2.36), enfenamic acid (2.37), etersalate (2.38), etodolac (2.39), etofenamat (2.40), etoricoxib (2.41), feclobuzon (2.42), felbinac (2.43), fenbufen (2.44), fenclofenac (2.45), fenoprofen (2.46), fentiazac (2.47), fepradinol (2.48), feprazone (2.49), flobufen (2.50), floctafenin (2.51), flufenamic acid (2.52), flufenisal (2.53), flunoxaprofen (2.54), flurbiprofen (2.55), flurbiprofenaxetil (2.56), furofenac (2.57), furprofen (2.58), glucametacin (2.59), ibufenac (2.60), ibuprofen (2.61), indobufen (2.62), indometacin (2.63), indometacinfarnesil (2.64), indoprofen (2.65), isoxepac (2.66), isoxicam (2.67), ketoprofen (2.68), ketorolac (2.69), lobenzarit (2.70), lonazolac (2.71), lornoxicam (2.72), loxoprofen (2.73), lumiracoxib (2.74), meclofenamic acid (2.75), meclofen, mefenamic acid (2.76), meloxicam (2.77), mesalazin (2.78), miroprofen (2.79), mofezolac (2.80), nabumetone (2.81), naproxen (2.82), nifluminic acid (2.83), olsalazine (2.84), oxaprozin (2.85), oxipinac (2.86), oxyphenbutazone (2.87), parecoxib (2.88), phenylbutazone (2.89), pelubiprofen (2.90), pimeprofen (2.91), pirazolac (2.92), priroxicam (2.93), pirprofen (2.94), pranoprofen (2.95), prifelon (2.96), prinomod (2.97), proglumetacin (2.98), proquazone (2.99), protizinic acid (2.100), rofecoxib (2.101), romazarit (2.102), salicylamide (2.103), salicylic acid (2.104), salmistein (2.105), salnacedin (2.106), salsalate (2.107), sulindac (2.108), sudoxicam (2.109), suprofen (2.110), talniflumat (2.111), tenidap (2.112), tenosal (2.113), tenoxicam (2.114), tepoxalin (2.115), tiaprofenic acid (2.116), taramide (2.117), tilnoprofenarbamel (2.118), timegadine (2.119), tinoridine (2.120), tiopinac (2.121), tolfenamic acid (2.122), tolmetin (2.123), ufenamate (2.124), valdecoxib (2.125), ximoprofen (2.126), zaltoprofen (2.127) and zoliprofen (2.128).

Also particularly preferred are the above drug combinations which contain, in addition to one or more, preferably one PDE4 inhibitor of general formula 1, as NSAID (2) at least one COX 2 inhibitor selected from among celecoxib (2.25), etoricoxib (2.41), lumiracoxib (2.74), parecoxib (2.88), rofecoxib (2.101) and valdecoxib (2.125).

Also particularly preferred are the above drug combinations which contain, in addition to one or more, preferably one PDE4 inhibitor of general formula 1 at least one NSAID (2) selected from among acetylsalicylic acid (2.3), celecoxib (2.25), diclofenac (2.33), ibuprofen (2.61), indometacin (2.63), lumiracoxib (2.74), meloxicam (2.77), naproxen (2.82) and priroxicam (2.93).

Still more preferred are those of the above drug combinations which contain, in addition to one or more, preferably one PDE4 inhibitor of general formula 1, at least one NSAID (2) selected from among acetylsalicylic acid (2.3), diclofenac (2.33), meloxicam (2.77), naproxen (2.82) and ibuprofen (2.61).

Particularly preferred within the scope of the present invention are those of the above drug combinations which are selected from among 1.1 and 2.3; 1.1 and 2.33; 1.1 and 2.77; 1.1 and 2.82; 1.1 and 2.61; 1.2 and 2.3; 1.2 and 2.33; 1.2 and 2.77; 1.2 and 2.82; 1.2 and 2.61; 1.3 and 2.3; 1.3 and 2.33; 1.3 and 2.77; 1.3 and 2.82; 1.3 and 2.61; 1.4 and 2.3; 1.4 and 2.33; 1.4 and 2.77; 1.4 and 2.82; 1.4 and 2.61; 1.5 and 2.3; 1.5 and 2.33; 1.5 and 2.77; 1.5 and 2.82; 1.5 and 2.61; 1.6 and 2.3; 1.6 and 2.33; 1.6 and 2.77; 1.6 and 2.82; 1.6 and 2.61; 1.7 and 2.3; 1.7 and 2.33; 1.7 and 2.77; 1.7 and 2.82; 1.7 and 2.61; 1.8 and 2.3; 1.8 and 2.33; 1.8 and 2.77; 1.8 and 2.82; 1.8 and 2.61; 1.9 and 2.3; 1.9 and 2.33; 1.9 and 2.77; 1.9 and 2.82; 1.9 and 2.61; 1.10 and 2.3; 1.10 and 2.33; 1.10 and 2.77; 1.10 and 2.82; 1.10 and 2.61; 1.11 and 2.3; 1.11 and 2.33; 1.11 and 2.77; 1.11 and 2.82; 1.11 and 2.61; 1.12 and 2.3; 1.12 and 2.33; 1.12 and 2.77; 1.12 and 2.82; 1.12 and 2.61; 1.13 and 2.3; 1.13 and 2.33; 1.13 and 2.77; 1.13 and 2.82; 1.13 and 2.61; 1.14 and 2.3; 1.14 and 2.33; 1.14 and 2.77; 1.14 and 2.82; 1.14 and 2.61; 1.15 and 2.3; 1.15 and 2.33; 1.15 and 2.77; 1.15 and 2.82; 1.15 and 2.61; 1.16 and 2.3; 1.16 and 2.33; 1.16 and 2.77; 1.16 and 2.82; 1.16 and 2.61; 1.17 and 2.3; 1.17 and 2.33; 1.17 and 2.77; 1.17 and 2.82; 1.17 and 2.61; 1.18 and 2.3; 1.18 and 2.33; 1.18 and 2.77; 1.18 and 2.82; 1.18 and 2.61; 1.19 and 2.3; 1.19 and 2.33; 1.19 and 2.77; 1.19 and 2.82; 1.19 and 2.61; 1.20 and 2.3; 1.20 and 2.33; 1.20 and 2.77; 1.20 and 2.82; 1.20 and 2.61; 1.21 and 2.3; 1.21 and 2.33; 1.21 and 2.77; 1.21 and 2.82; 1.21 and 2.61; 1.22 and 2.3; 1.22 and 2.33; 1.22 and 2.77; 1.22 and 2.82; 1.22 and 2.61; 1.23 and 2.3; 1.23 and 2.33; 1.23 and 2.77; 1.23 and 2.82; 1.23 and 2.61; 1.24 and 2.3; 1.24 and 2.33; 1.24 and 2.77; 1.24 and 2.82; 1.24 and 2.61; 1.25 and 2.3; 1.25 and 2.33; 1.25 and 2.77; 1.25 and 2.82; 1.25 and 2.61; 1.26 and 2.3; 1.26 and 2.33; 1.26 and 2.77; 1.26 and 2.82; 1.26 and 2.61; 1.27 and 2.3; 1.27 and 2.33; 1.27 and 2.77; 1.27 and 2.82; 1.27 and 2.61; 1.28 and 2.3; 1.28 and 2.33; 1.28 and 2.77; 1.28 and 2.82; 1.28 and 2.61; 1.29 and 2.3; 1.29 and 2.33; 1.29 and 2.77; 1.29 and 2.82; 1.29 and 2.61; 1.30 and 2.3; 1.30 and 2.33; 1.30 and 2.77; 1.30 and 2.82; 1.30 and 2.61; 1.31 and 2.3; 1.31 and 2.33; 1.31 and 2.77; 1.31 and 2.82; 1.31 and 2.61; 1.32 and 2.3; 1.32 and 2.33; 1.32 and 2.77; 1.32 and 2.82; 1.32 and 2.61; 1.33 and 2.3; 1.33 and 2.33; 1.33 and 2.77; 1.33 and 2.82; 1.33 and 2.61; 1.34 and 2.3; 1.34 and 2.33; 1.34 and 2.77; 1.34 and 2.82; 1.34 and 2.61; 1.35 and 2.3; 1.35 and 2.33; 1.35 and 2.77; 1.35 and 2.82; 1.35 and 2.61; 1.36 and 2.3; 1.36 and 2.33; 1.36 and 2.77; 1.36 and 2.82; 1.36 and 2.61, 1.37 and 2.3; 1.37 and 2.33; 1.37 and 2.77; 1.37 and 2.82; 1.37 and 2.61; 1.38 and 2.3; 1.38 and 2.33; 1.38 and 2.77; 1.38 and 2.82; 1.38 and 2.61; 1.39 and 2.3; 1.39 and 2.33; 1.39 and 2.77; 1.39 and 2.82; 1.39 and 2.61; 1.40 and 2.3; 1.40 and 2.33; 1.40 and 2.77; 1.40 and 2.82; 1.40 and 2.61; 1.41 and 2.3; 1.41 and 2.33; 1.41 and 2.77; 1.41 and 2.82; 1.41 and 2.61; 1.42 and 2.3; 1.42 and 2.33; 1.42 and 2.77; 1.42 and 2.82; 1.42 and 2.61; 1.43 and 2.3; 1.43 and 2.33; 1.43 and 2.77; 1.43 and 2.82; 1.43 and 2.61; 1.44 and 2.3; 1.44 and 2.33; 1.44 and 2.77; 1.44 and 2.82; 1.44 and 2.61; 1.45 and 2.3; 1.45 and 2.33; 1.45 and 2.77; 1.45 and 2.82; 1.45 and 2.61.

The invention relates particularly to those of the above drug combinations wherein the PDE4 inhibitor of general formula 1 is administered in a single dose of 0.01 mg to 50 mg, preferably 0.05 to 30 mg, more preferably 0.1 to 20 mg, particularly 0.5 to 10 mg.

Also particularly preferred are the above mentioned drug combinations, wherein the NSAID (2) used is either
  acetylsalicylic acid (2.3) in a single dose of 50 to 2000 mg, preferably 100 to 500 mg,
  diclofenac (2.33) in a single dose of 25 mg to 150 mg, preferably 25 to 100 mg,
  meloxicam (2.77) in a single dose of 7.5 mg to 30 mg, preferably 10 to 20 mg,
  naproxen in a single dose of 250 to 1000 mg, preferably 250 to 750 mg, and
  ibuprofen in a single dose of 200 to 2400 mg, preferably 200 to 800 mg,
this single dose in each case being given once or twice a day.

In particular the invention relates to the above mentioned drug combinations, wherein the or at least one or more of the PDE4 inhibitor-mediated side effects is considerably reduced or avoided completely by comparison with the sole administration of the PDE4 inhibitor used in the drug combination. These PDE4 inhibitor-mediated side effects are preferably selected from among weight loss, leukocytosis, neutrophilia, nausea, vomiting, diarrhoea (including the occurrence of inflammatory parameters and the proliferation of fibroblasts in the mesentery). These PDE4 inhibitor-mediated side effects are more preferably selected from weight loss, leukocytosis, neutrophilia and diarrhoea. These PDE4 inhibitor-mediated side effects relate particularly to the occurrence of diarrhoea.

The present invention further relates to the use of an NSAID (2) for reducing the side effects of one or more PDE4-inhibitors in the treatment of a disease selected from among respiratory complaints, pulmonary diseases, gastrointestinal ailments and diseases and also inflammatory diseases of the joints, skin or eyes, cancers and diseases of the peripheral or central nervous system.

In another aspect the present invention relates to the use of a combination containing one or more PDE4-inhibitors and at least one NSAID (2) for the treatment of a disease selected from among respiratory complaints, pulmonary diseases, gastrointestinal ailments and diseases and also inflammatory diseases of the joints, skin or eyes, cancers and diseases of the peripheral or central nervous system.

It is also preferable to use the combination of one or more, preferably one, PDE4 inhibitor of general formula 1,

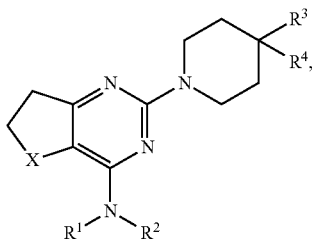

wherein X, $R^1$, $R^2$, $R^3$ and $R^4$ are defined as hereinbefore and according to the preferred definitions,
and at least one NSAID (2) for preparing a drug combination for the treatment of one of the diseases selected from respiratory complaints, pulmonary diseases, gastrointestinal ailments and diseases and also inflammatory diseases of the joints, skin or eyes, cancers and diseases of the peripheral or central nervous system, but particularly for the treatment of inflammatory and obstructive diseases such as COPD, chronic sinusitis, asthma, Crohn's disease and ulcerative colitis.

In a preferred aspect the invention relates to the use of the combination containing one or more PDE4-inhibitors—particularly one or more of the PDE4-inhibitors according to formula 1—and of the at least one NSAID (2) for preparing a drug combination for the treatment of the above mentioned diseases, characterised in that the PDE4 inhibitor—particularly the PDE4 inhibitor of formula 1—and the at least one NSAID (2) are administered together and simultaneously in a single formulation, this single formulation preferably being an oral formulation such as for example a tablet, capsule or the like.

It is also preferable to use the combination containing one or more PDE4-inhibitors -particularly one or more PDE4-inhibitors according to formula 1—and the at least one NSAID (2) to prepare a drug combination for the treatment of the above mentioned diseases, characterised in that the PDE4 inhibitor—particularly the PDE4 inhibitor of formula 1—and the at least one NSAID (2) are administered in two separate formulations separated from one another within a time interval of 0 to 6 hours. In this separate administration in two separate formulations the formulation containing the PDE4 inhibitor—particularly the PDE4 inhibitor of formula 1—may be an oral or inhalative formulation, but is preferably an oral formulation, and the formulation containing the at least one NSAID (2) is preferably an oral formulation. Moreover, when the combination is used in separate formulations to prepare a drug combination for the treatment of the above mentioned diseases the formulation containing the PDE4 inhibitor—particularly the PDE4 inhibitor of formula 1—is preferably administered once a day and the formulation containing the at least one NSAID (2) is preferably administered either once or twice a day.

For the use of the combination as described above, particularly preferred PDE4-inhibitors of general formula 1 are those selected from among:

1.1 (R)-2-{2-[4-(4-chlorophenyl)-piperidin-1-yl]-5-oxo-6,7-dihydro-5H-5λ4-thieno[3,2-d]pyrimidin-4-ylamino}-3-methylbutan-1-ol
1.2 (1-{2-[4-(4-chlorophenyl)-piperidin-1-yl]-5-oxo-6,7-dihydro-5H-5λ4-thieno[3,2-d]pyrimidin-4-ylamino}-cyclopropyl)-methanol
1.3 (R)-2-{2-[4-(4-chlorophenyl)-piperidin-1-yl]-5-oxo-6,7-dihydro-5H-5λ4-thieno[3,2-d]pyrimidin-4-ylamino}-pentan-1-ol
1.4 (R)-1-{2-[4-(4-chlorophenyl)-piperidin-1-yl]-5-oxo-6,7-dihydro-5H-5λ4-thieno[3,2-d]pyrimidin-4-ylamino}-1-(4-fluorophenyl)-2-methylpropan-2-ol
1.5 (S)-5-{2-[4-(4-chlorophenyl)-piperidin-1-yl]-5-oxo-6,7-dihydro-5H-5λ4-thieno[3,2-d]pyrimidin-4-ylamino}-1-methylpiperidin-2-one
1.6 {2-[4-(4-chlorophenyl)-piperidin-1-yl]-5-oxo-6,7-dihydro-5H-5λ4-thieno[3,2-d]pyrimidin-4-yl}-(tetrahydropyran-4-yl)-amine
1.7 1-(4-(1-hydroxymethylcyclopropylamino)-5-oxo-6,7-dihydro-5H-5λ4-thieno[3,2-d]pyrimidin-2-yl)-3'-methyl-1'H-spiro[piperidin-4,4'-quinazolin]-2'(3'H)-one
1.8 {1-[2-(4-benzo[d]isoxazol-3-yl-piperidin-1-yl)-5-oxo-6,7-dihydro-5H-5λ4-thieno[3,2-d]pyrimidin-4-ylamino]-cyclopropyl}-methanol
1.9 (1-{2-[4-(2-ethyl-5-fluoro-1H-indol-3-yl)-piperidin-1-yl]-5-oxo-6,7-dihydro-5H-5λ4-thieno[3,2-d]pyrimidin-4-ylamino}-cyclopropyl)-methanol
1.10 1-[4-((S)-1-methyl-6-oxopiperidin-3-ylamino)-5-oxo-6,7-dihydro-5H-5λ4-thieno[3,2-d]pyrimidin-2-yl]-4-phenylpiperidin-4-carbonitrile
1.11 3'-methyl-1-(4-(tetrahydro-2H-pyran-4-ylamino)-5-oxo-6,7-dihydro-5H-5λ4-thieno[3,2-d]pyrimidin-2-yl)-1'H-spiro[piperidin-4,4'-quinazolin]-2'(3'H)-one
1.12 (3-fluorophenyl)-[5-oxo-2-(3,4,5,6-tetrahydro-2H-[4,4']bipyridinyl-1-yl)-6,7-dihydro-5H-5λ4-thieno[3,2-d]pyrimidin-4-yl]-amine
1.13 {2-[4-(2-ethyl-5-fluoro-1H-indol-3-yl)-piperidin-1-yl]-5-oxo-6,7-dihydro-5H-5λ4-thieno[3,2-d]pyrimidin-4-yl}-(3-fluorophenyl)-amine
1.14 (1-{2-[4-(2,4-difluorophenyl)-piperidin-1-yl]-5-oxo-6,7-dihydro-5H-5λ4-thieno[3,2-d]pyrimidin-4-ylamino}-cyclopropyl)-methanol
1.15 {2-[4-(2,4-difluorophenyl)-piperidin-1-yl]-5-oxo-6,7-dihydro-5H-5λ4-thieno[3,2-d]pyrimidin-4-yl}-(tetrahydropyran-4-yl)-amine
1.16 (S)-5-[2-(4-benzoxazol-2-yl-piperidin-1-yl)-5-oxo-6,7-dihydro-5H-5λ4-thieno[3,2-d]pyrimidin-4-ylamino]-1-methylpiperidin-2-one
1.17 (1-{2-[4-(6-fluorobenzo[d]isoxazol-3-yl)-piperidin-1-yl]-5-oxo-6,7-dihydro-5H-5λ4-thieno[3,2-d]pyrimidin-4-ylamino}-cyclopropyl)-methanol
1.18 (1-{2-[4-(5-fluorobenzo[d]isoxazol-3-yl)-piperidin-1-yl]-5-oxo-6,7-dihydro-5H-5λ4-thieno[3,2-d]pyrimidin-4-ylamino}-cyclopropyl)-methanol
1.19 {2-[4-(5-furan-2-yl-2H-pyrazol-3-yl)-piperidin-1-yl]-5-oxo-6,7-dihydro-5H-5λ4-thieno[3,2-d]pyrimidin-4-yl}-(tetrahydropyran-4-yl)-amine 1.20 {3-fluorophenyl)-(5-oxo-2-[4-(3-pyridin-4-yl-[1,2,4]oxadiazol-5-yl)-piperidin-1-yl]-6,7-dihydro-5H-5λ4-thieno[3,2-d]pyrimidin-4-yl}-amine 1.21 (R)-3-methyl-2-{5-oxo-2-[4-(3-pyridin-4-yl-[1,2,4]oxadiazol-5-yl)-piperidin-1-yl]-6,7-dihydro-5H-5λ4-thieno[3,2-d]pyrimidin-4-ylamino}-butan-1-ol 1.22 (S)-5-{2-[4-(4-fluorophenoxy)-piperidin-1-yl]-5-oxo-6,7-dihydro-5H-5λ4-thieno[3,2-d]pyrimidin-4-ylamino}-1-methylpiperidin-2-one 1.23 (2-{4-[4-(4,5-dihydrooxazol-2-yl)-phenoxy]-piperidin-1-yl}-5-oxo-6,7-dihydro-5H-5λ4-thieno[3,2-d]pyrimidin-4-yl)-(tetrahydropyran-4-yl)-amine 1.24 4-{1-[5-oxo-4-(tetrahydropyran-4-ylamino)-6,7-dihydro-5H-5λ4-thieno[3,2-d]pyrimidin-2-yl]-piperidin-4-yloxy}-benzoic acid 1.25 2-(1-{2-[4-(4-chlorophenyl)-piperidin-1-yl]-5-oxo-6,7-dihydro-5H-5λ4-thieno[3,2-d]pyrimidin-4-ylamino}-cyclopropyl)-propan-2-ol 1.26 {2-[4-(5-tert-butyl-1-methyl-1H-indol-3-yl)-piperidin-1-yl]-5-oxo-6,7-dihydro-5H-5λ4-thieno[3,2-d]pyrimidin-4-yl}-(tetrahydropyran-4-yl)-amine 1.27 2-[4-(5-furan-2-yl-1-methyl-1H-pyrazol-3-yl)-piperidin-1-yl]-5-oxo-6,7-dihydro-5H-5λ4-thieno[3,2-d]pyrimidin-4-yl}-(tetrahydropyran-4-yl)-amine 1.28 (S)-5-(2-{4-[4-(4,5-dihydrooxazol-2-yl)-phenoxy]-piperidin-1-yl}-5-oxo-6,7-dihydro-5H-5λ4-thieno[3,2-d]pyrimidin-4-ylamino)-1-methylpiperidin-2-one 1.29 {2-[4-(5-furan-2-yl-2-methyl-2H-pyrazol-3-yl)-piperidin-1-yl]-5-oxo-6,7-dihydro-5H-5λ4-thieno[3,2-d]pyrimidin-4-yl}-(tetrahydropyran-4-yl)-amine 1.30 {2-[4-(1-methyl-1H-imidazo[4,5-c]pyridin-2-yl)-piperidin-1-yl]-5-oxo-6,7-dihydro-5H-5λ4-thieno[3,2-d]pyrimidin-4-yl}-(tetrahydropyran-4-yl)-amine 1.31 2-methoxy-N-{1-[5-oxo-4-(tetrahydropyran-4-ylamino)-6,7-dihydro-5H-5λ4-thieno[3,2-d]pyrimidin-2-yl]-4-phenylpiperidin-4-ylmethyl}-acetamide 1.32 N-cyclopropyl-N-methyl-4-{1-[5-oxo-4-(tetrahydropyran-4-ylamino)-6,7-dihydro-5H-5λ4-thieno[3,2-d]pyrimidin-2-yl]-piperidin-4-yl}-benzamide 1.33 N-cyclopropyl-N-methyl-4-{1-[5-oxo-4-(tetrahydropyran-4-ylamino)-6,7-dihydro-5H-5λ4-thieno[3,2-d]pyrimidin-2-yl]-piperidin-4-yloxy}-benzamide 1.34 {5-oxo-2-[4-(pyridin-4-yloxy)-piperidin-1-yl]-6,7-dihydro-5H-5λ4-thieno[3,2-d]pyrimidin-4-yl}-(tetrahydropyran-4-yl)-amine 1.35 {2-[4-(4-chlorophenoxy)-piperidin-1-yl]-5-oxo-6,7-dihydro-5H-5λ4-thieno[3,2-d]pyrimidin-4-yl}-(tetrahydropyran-4-yl)-amine 1.36 (S)-1-methyl-5-{2-[4-(5-methyl-4-phenyloxazol-2-yl)-piperidin-1-yl]-5-oxo-6,7-dihydro-5H-5λ4-thieno[3,2-d]pyrimidin-4-ylamino}-piperidin-2-one 1.37 (1-{2-[4-(5-methyl-4-phenyloxazol-2-yl)-piperidin-1-yl]-5-oxo-6,7-dihydro-5H-5λ4-thieno[3,2-d]pyrimidin-4-ylamino}-cyclopropyl)-methanol 1.38 (S)-5-{2-[4-(4,5-diphenyloxazol-2-yl)-piperidin-1-yl]-5-oxo-6,7-dihydro-5H-5λ4-thieno[3,2-d]pyrimidin-4-ylamino}-1-methylpiperidin-2-one 1.39 {4-(4-chlorophenyl)-1-[5-oxo-4-(tetrahydropyran-4-ylamino)-6,7-dihydro-5H-5λ4-thieno[3,2-d]pyrimidin-2-yl]-piperidin-4-yl}-methanol 1.40 [1-(2-{4-[5-(4-chlorophenyl)-4-methyloxazol-2-yl]-piperidin-1-yl}-5-oxo-6,7-dihydro-5H-5λ4-thieno[3,2-d]pyrimidin-4-ylamino)-cyclopropyl]-methanol 1.41 4-(4-chlorophenyl)-1-[5-oxo-4-(tetrahydropyran-4-ylamino)-6,7-dihydro-5H-5λ4-thieno[3,2-d]pyrimidin-2-yl]-piperidin-4-ol 1.42 {2-[4-(4-chlorophenyl)-4-methoxypiperidin-1-yl]-5-oxo-6,7-dihydro-5H-5λ4-thieno[3,2-d]pyrimidin-4-yl}-(tetrahydropyran-4-yl)-amine 1.43 4-{1-[4-(1-hydroxymethylcyclopropylamino)-5-oxo-6,7-dihydro-5H-5λ4-thieno[3,2-d]pyrimidin-2-yl]-piperidin-4-yloxy}-benzonitrile 1.44 {5-oxo-2-[4-(4,5,6,7-tetrahydrobenzoxazol-2-yl)-piperidin-1-yl]-6,7-dihydro-5H-5λ4-thieno[3,2-d]pyrimidin-4-yl}-(tetrahydropyran-4-yl)-amine 1.45 (S)-5-{2-[4-(4-chlorophenyl)-piperidin-1-yl]-5,5-dioxo-6,7-dihydro-5H-5λ6-thieno[3,2-d]pyrimidin-4-ylamino}-1-methylpiperidin-2-one.

In the use described above, the at least one NSAID (2) is preferably selected from among: aceclofenac (2.1), acemetacin (2.2), acetylsalicylic acid (2.3), alclofenac (2.4), alminoprofen (2.5), amfenac (2.6), ampiroxicam (2.7), antolmetinguacil (2.8), anirolac (2.9), antrafenine (2.10), azapropazone (2.11), benorilate (2.12), bermoprofen (2.13), bindarit (2.14), bromfenac (2.15), bucloxinic acid (2.16), bucolom (2.17), bufexamac (2.18), bumadizone (2.19), butibufen (2.20), butixirate (2.21), carbasalate calcium (2.22), carprofen (2.23), choline magnesium trisalicylate (2.24), celecoxib (2.25), cinmetacin (2.26), cinnoxicam (2.27), clidanac (2.28), clobuzarit (2.29), deboxamet (2.30), dexibuprofen (2.31), dexketoprofen (2.32), diclofenac (2.33), diflunisal (2.34), droxicam (2.35), eltenac (2.36), enfenamic acid (2.37), etersalate (2.38), etodolac (2.39), etofenamat (2.40), etoricoxib (2.41), feclobuzon (2.42), felbinac (2.43), fenbufen (2.44), fenclofenac (2.45), fenoprofen (2.46), fentiazac (2.47), fepradinol (2.48), feprazone (2.49), flobufen (2.50), floctafenin (2.51), flufenamic acid (2.52), flufenisal (2.53), flunoxaprofen (2.54), flurbiprofen (2.55), flurbiprofenaxetil (2.56), furofenac (2.57), furprofen (2.58), glucametacin (2.59), ibufenac (2.60), ibuprofen (2.61), indobufen (2.62), indometacin (2.63), indometacinfarnesil (2.64), indoprofen (2.65), isoxepac (2.66), isoxicam (2.67), ketoprofen (2.68), ketorolac (2.69), lobenzarit (2.70), lonazolac (2.71), lornoxicam (2.72), loxoprofen (2.73), lumiracoxib (2.74), meclofenamic acid (2.75), meclofen, mefenamic acid (2.76), meloxicam (2.77), mesalazin (2.78), miroprofen (2.79), mofezolac (2.80), nabumetone (2.81), naproxen (2.82), nifluminsäure (2.83), olsalazine (2.84), oxaprozin (2.85), oxipinac (2.86), oxyphenbutazone (2.87), parecoxib (2.88), phenylbutazone (2.89), pelubiprofen (2.90), pimeprofen (2.91), pirazolac (2.92), priroxicam (2.93), pirprofen (2.94), pranoprofen (2.95), prifelon (2.96), prinomod (2.97), proglumetacin (2.98), proquazone (2.99), protizinic acid (2.100), rofecoxib (2.101), romazarit (2.102), salicylamide (2.103), salicylic acid (2.104), salmistein (2.105), salnacedin (2.106), salsalate (2.107), sulindac (2.108), sudoxicam (2.109), suprofen (2.110), talniflumat (2.111), tenidap (2.112), tenosal (2.113), tenoxicam (2.114), tepoxalin (2.115), tiaprofenic acid (2.116), taramide (2.117), tilnoprofenarbamel (2.118), timegadine (2.119), tinoridine (2.120), tiopinac (2.121), tolfenamic acid (2.122), tolmetin (2.123), ufenamate (2.124), valdecoxib (2.125), ximoprofen (2.126), zaltoprofen (2.127) and zoliprofen (2.128).

More preferably, in the use described above, an NSAID (2) is used which is selected from among acetylsalicylic acid (2.3), celecoxib (2.25), diclofenac (2.33), ibuprofen (2.61), indometacin (2.63), lumiracoxib (2.74), meloxicam (2.77), naproxen (2.82) and priroxicam (2.93).

Even more preferably, in the use described above, an NSAID (2) is used which is selected from among acetylsalicylic acid (2.3), diclofenac (2.33), meloxicam (2.77), naproxen (2.82) and ibuprofen (2.61).

Particularly, in the use described above, an NSAID (2) is used which is selected from among acetylsalicylic acid (2.3), preferably in a single dose of 50 to 2000 mg, more preferably 100 to 500 mg, diclofenac (2.33), preferably in a single dose of 25 to 150 mg, more preferably 25 to 100 mg, meloxicam (2.77), preferably in a single dose of 7.5 to 30 mg, more preferably 10 to 20 mg naproxen (2.82), preferably in a single dose of 250 to 1000 mg, more preferably 250 to 750 mg, and ibuprofen (2.61), preferably in a single dose of 200 to 2400 mg, more preferably 200 to 800 mg used, while this single dose may be administered once or twice a day.

In particular, in the above-mentioned uses of the combination for treating the above mentioned diseases the PDE4 inhibitor of general formula 1 is given in a single dose of 0.01 mg to 50 mg, preferably 0.05 to 30 mg, more preferably 0.1 to 20 mg, particularly 0.5 to 10 mg.

In particular, the invention relates to the above mentioned uses, wherein the or at least one or more of the PDE4 inhibitor-mediated side effects is substantially reduced or prevented completely, by comparison with the sole administration of the PDE4 inhibitor used in the drug combination.

The invention also particularly relates to the use of NSAIDs, preferably as hereinbefore defined and according to the preferred definitions, for reducing or avoiding one or more PDE4 inhibitor-mediated side effects.

These PDE4 inhibitor-mediated side effects are preferably selected from among weight loss, leukocytosis, neutrophilia, nausea, vomiting, diarrhoea (including the occurrence of inflammatory parameters and the proliferation of fibroblasts in the mesentery). These PDE4 inhibitor-mediated side effects are more preferably selected from weight loss, leukocytosis, neutrophilia and diarrhoea. These PDE4 inhibitor-mediated side effects relate particularly to the occurrence of diarrhoea.

BRIEF DESCRIPTION OF THE FIGURES

FIG. 1B shows the determination of the proportion of white blood cells (×1000 cells/μl blood, FIG. 1B, left-hand Figure) and of the proportion of neutrophils (in % of white blood cells, FIG. 1B, right-hand Figure) 95 hours after t0 (the time of the first administration on day 1,0800) from the blood of 4 or 5 of the rats from the individual groups. (statistics: One-way analysis of variance; ns=not significant; ***=p<0.001).

FIG. 2A shows the body weights of the rats from the different groups as a percentage change from the time of the first administration (day 1,0800 hours (=time t0)). The average ± standard deviation of the body weights at time t0 was 306±11 g.

FIG. 2B shows the determination of the proportion of white blood cells (×1000 cells/μl blood, FIG. 2B, left-hand Figure) and of the proportion of neutrophils (in % of white blood cells, FIG. 2B, right-hand Figure) 95 hours after t0 (the time of the first administration on day 1,0800 hours) from the blood of 5 of the rats from the individual groups. (statistics: One-way analysis of variance; ns=not significant; *=p<0.05; ***=p<0001).

SYNTHESIS INSTRUCTIONS

Figure 1A:
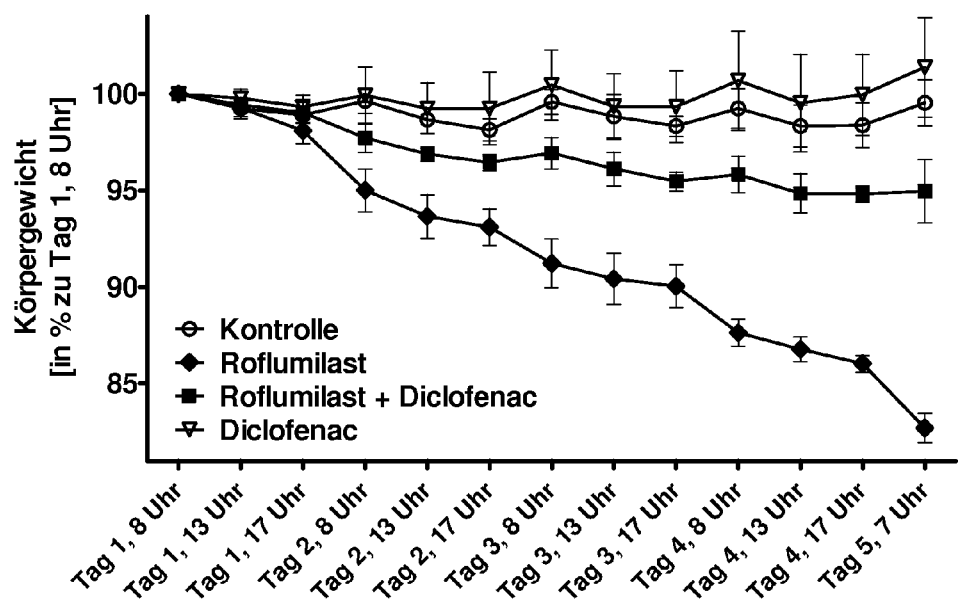
FIG. 1A shows the body weights of the rats from the different groups (control group, Roflumilast group, Roflumilast+Diclofenac group, Diclofenac group) as a percentage change from the time of the first administration (day 1,0800 hours (=time t0)). The average ± standard deviation of the body weights at time t0 was 355±17 g.

The compounds of general formula (I) may be prepared according to the following general synthesis scheme in which the substituents of general formula (I) have the meanings given hereinbefore. These methods are to be understood as illustrating the invention without restricting it to their subject-matter.

GENERAL SYNTHESIS SCHEME 1

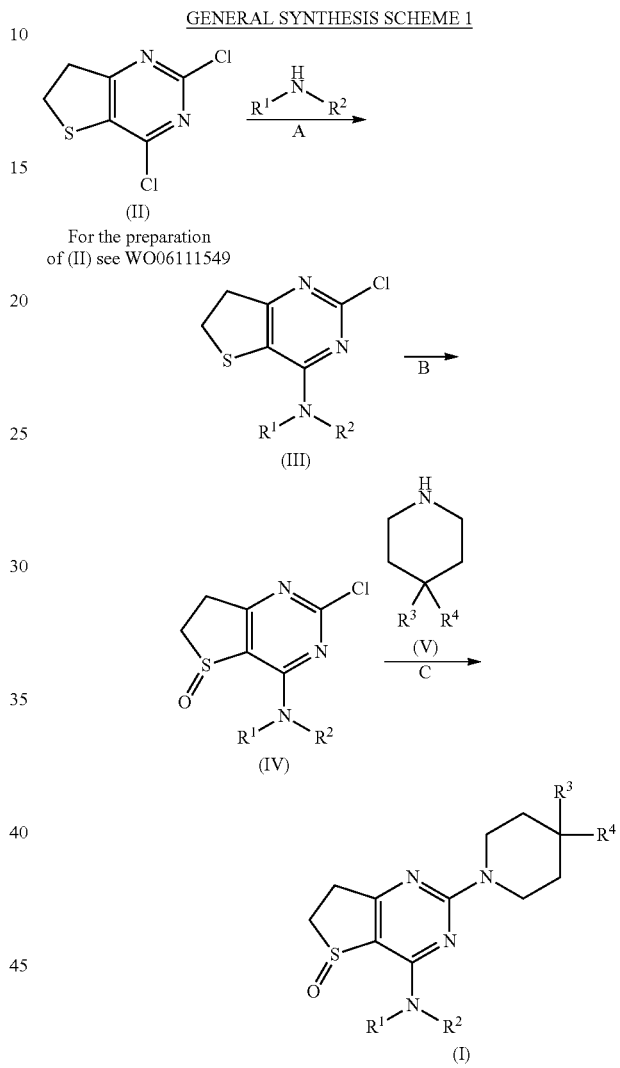

1. SYNTHESIS OF (R)-2-{2-[4-(4-CHLOROPHE-NYL)-PIPERIDIN-1-YL]-5-OXO-6,7-DIHYDRO-5H-5λ⁴-THIENO[3,2-D]PYRIMIDIN-4-YLAMINO}-3-METHYLBUTAN-1-OL

Example 1.1

1.1 (R)-2-(2-chloro-6,7-dihydrothieno[3,2-d]pyrimidin-4-ylamino)-3-methylbutan-1-ol (III-1)

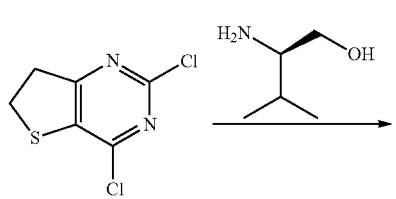

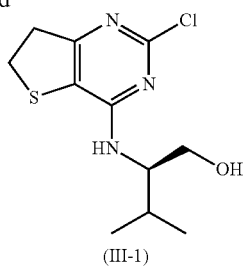

(III-1)

7.2 g 2,4-dichloro-6,7-dihydrothieno[3,2-d]pyrimidine (II) are placed in 36 ml dioxane, then first 18 ml diisopropylethylamine are added, followed by 6.1 g (R)-(−)-2-amino-3-methyl-1-butanol. The reaction mixture is heated to 100° C. until there is no further reaction, then cooled and evaporated down. The residue is treated with petroleum ether/ethyl acetate (9:1) in the ultrasound bath and the solid is suction filtered and dried. 8.3 g (III-1) are obtained in the form of a solid. Analytical HPLC (method A): RT=2.75 min 1.2 (R)-2-(2-chloro-5-oxo-6,7-dihydro-5H-5$\lambda^4$-thieno[3,2-d]pyrimidin-4-ylamino)-3-methylbutan-1-ol (IV-1)

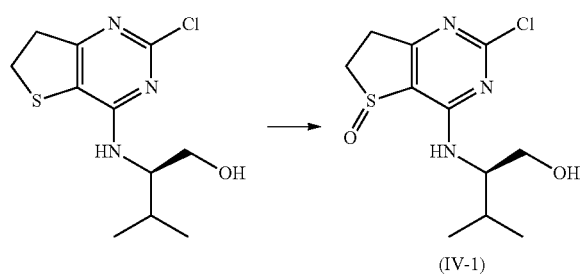

(IV-1)

4.1 g S-(−)-1,1'-Bi-2-naphthol are placed in 15 ml chloroform under argon, then 0.44 ml titanium(IV)-isopropoxide and 0.54 ml of water are added. The reaction mixture is stirred for 1 hour at ambient temperature. Then a suspension of 4.1 g (III-1) in 107 ml dichloromethane is added. The reaction mixture is cooled to −2° C. and after 30 minutes 2.7 ml tert-butylhydroperoxide 5-6 M in decane are added dropwise. The reaction mixture is stirred at −2° C. until there is no further reaction and made basic with NH$_4$OH. The product is extracted with dichloromethane and purified by chromatography (silica gel, ethyl acetate/methanol 100/0 to 86/14). 2.45 g (IV-1) are obtained in the form of a solid. Analytical HPLC (method A): RT=2.37 min 1.3 (R)-2-{2-[4-(4-chlorophenyl)-piperidin-1-yl]-5-oxo-6,7-dihydro-5H-5$\lambda^4$-thieno[3,2-d]pyrimidin-4-ylamino}-3-methylbutan-1-ol Example 1.1

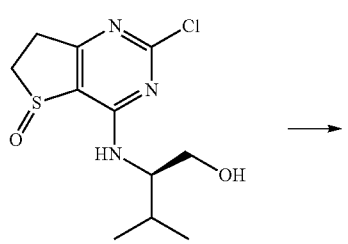

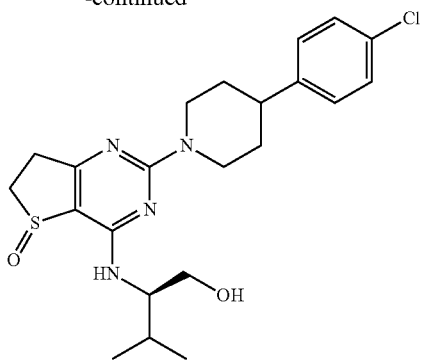

Example 1.1

0.2 g (IV-1) is placed in 3 ml dioxane and 360 μl diisopropylethylamine, combined with 0.16 g 4-(4-chlorophenyl)-piperidine and heated in the microwave at 120° C. until there is no further reaction. The reaction mixture is mixed with water, extracted with dichloromethane and the product is purified by chromatography (silica gel, dichloromethane/methanol 100/0 to 92/8). 0.33 g Example 1.1 are obtained in the form of a solid. Analytical HPLC-MS (method A): RT=1.24 min.

2. SYNTHESIS OF (1-{2-[4-(4-CHLOROPHENYL)-PIPERIDIN-1-YL]-5-OXO-6,7-DIHYDRO-5H-5$\lambda^4$-THIENO[3,2-D]PYRIMIDIN-4-YLAMINO}-CYCLOPROPYL)-METHANOL Example 1.2

2.1 tert-butyl (1-hydroxymethylcyclopropyl)-carbamidate

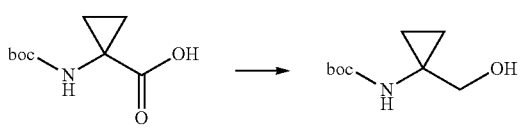

1 g 1-(BOC-amino)-cyclopropanecarboxylic acid is dissolved in 20 ml dimethoxyethane and cooled to −70° C. Then 0.65 ml N-methylmorpholine are added and 0.71 ml isobutylchloroformate in 5 ml dimethoxyethane is added dropwise. The reaction mixture is heated to −5° C. The precipitate is suction filtered. The eluate is cooled to −15° C. and 0.303 g sodium borohydride are slowly added. The reaction mixture is then stirred for 30 minutes at ambient temperature, mixed with water and the product is extracted with dichloromethane. The organic phase is dried and evaporated to dryness. 1.04 g product are obtained in the form of a solid. $^1$H NMR (400 MHz, DMSO): 1.36 (9H, s); 0.61 (2H, t); 0.52 (2H, t).

2.2 1-aminocyclopropanemethanol

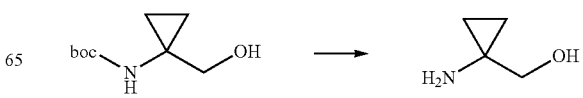

1.04 g tert-butyl (1-hydroxymethylcyclopropyl)-carbamidate are placed in 5 ml dioxane. 2.5 ml HCl in dioxane (4 mol/l) are added dropwise. The reaction mixture is stirred for 15 h at ambient temperature. The solvent is evaporated down by half and the precipitated solid is suction filtered. 0.5 g product are obtained as the hydrochloride. $^1$H NMR (400 MHz, DMSO): 5.27 (1H, t); 0.91 (2H, t); 0.71 (2H, t).

2.3 [1-(2-chloro-6,7-dihydrothieno[3,2-d]pyrimidin-4-ylamino)-cyclopropyl]-methanol (III-2)

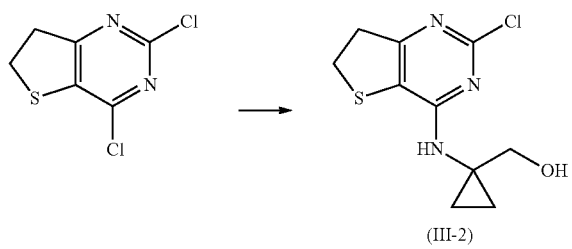 [SMILES: Clc1nc(Cl)c2c(n1)CCS2 ; OCC1(Nc2nc(Cl)nc3c2SCC3)CC1 ; "(III-2)"]

(III-2)

1.4 g (II) are placed in 10 ml dioxane, then 3.6 ml diisopropylethylamine are added followed by 1 g 1-aminocyclopropanmethanol (cf. 2.2). The reaction mixture is heated to 160° C. until there is no further reaction, then cooled and evaporated down. The residue is treated with cyclohexane/ethyl acetate (4:1) in the ultrasound bath, the solid is suction filtered and dried. 1.24 g (III-2) are obtained in the form of a solid. Analytical HPLC-MS (method A): RT=1.01 min.

2.4 [1-(2-chloro-5-oxo-6,7-dihydro-5H-5λ$^4$-thieno[3,2-d]pyrimidin-4-ylamino)-cyclopropyl]-methanol (IV-2)

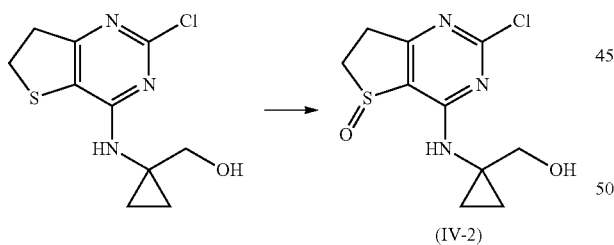

(IV-2)

0.28 g S-(−)-1,1'-Bi-2-naphthol are placed in 20 ml chloroform under argon, then 0.14 ml titanium(IV)-isopropoxide and 0.17 ml of water are added. The reaction mixture is stirred for 1 hour at ambient temperature. Then a suspension of 1.2 g (III-2) in 40 ml dichloromethane and 2 ml of methanol is added. The reaction mixture is cooled to −5° C. and after 30 minutes 0.91 ml tert-butylhydroperoxid 5-6 M in decane are added dropwise. The reaction mixture is stirred at −5° C. until there is no further reaction and made basic with NH$_4$OH. The aqueous phase is washed with dichloromethane and freeze-dried. 1 g (IV-2) is obtained in the form of a solid. Analytical HPLC-MS (method A) RT=0.85 min 2.5 (1-{2-[4-(4-chlorophenyl)-piperidin-1-yl]-5-oxo-6,7-dihydro-5H-5λ$^4$-thieno[3,2-d]pyrimidin-4-ylamino}-cyclopropyl)-methanol Example 1.2

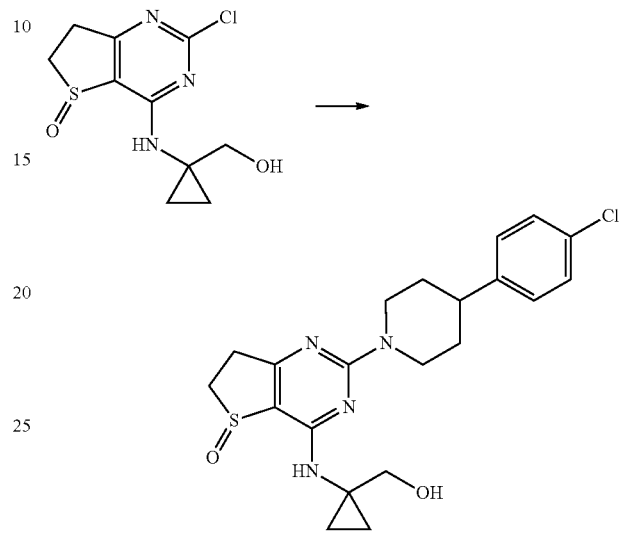

Example 1.2

Starting from 0.17 g (IV-2) and 0.15 g 4-(4-chlorophenyl)-piperidine 0.14 g Example 1.2 are prepared and purified analogously to Example 1.1 (cf. 1.3). Analytical HPLC-MS (method B): RT=1.32 min.

3. SYNTHESIS OF (R)-2-{2-[4-(4-CHLOROPHENYL)-PIPERIDIN-1-YL]-5-OXO-6,7-DIHYDRO-5H-5λ$^4$-THIENO[3,2-D]PYRIMIDIN-4-YLAMINO}-PENTAN-1-OL

Example 1.3

3.1 (R)-2-(2-chloro-6,7-dihydrothieno[3,2-d]pyrimidin-4-ylamino)-pentan-1-ol (III-3)

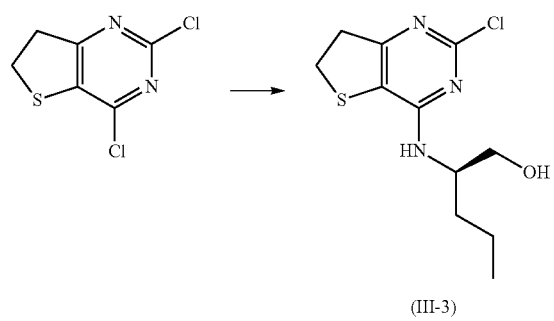 [SMILES: Clc1nc(Cl)c2c(n1)CCS2 ; CCC[C@H](CO)Nc1nc(Cl)nc2c1SCC2 ; "(III-3)"]

(III-3)

1.4 g 2,4-dichloro-6,7-dihydrothieno[3,2-d]pyrimidine (II) are placed in 9 ml dioxane, then 3.5 ml diisopropylethylamine are added followed by 0.9 g D-norvalinol. The reaction mixture is heated in the microwave at 120° C. until there is no further reaction then cooled and evaporated down. The residue is treated with petroleum ether/ethyl acetate 9:1 in the ultrasound bath, the solid is suction filtered and dried. 1.5 g (III-3) are obtained in the form of a solid. $^1$H NMR (400 MHz, DMSO): 4.67 (1H, t); 0.86 (3H, t).

3.2 (R)-2-(2-chloro-5-oxo-6,7-dihydro-5H-5λ$^4$-thieno[3,2-d]pyrimidin-4-ylamino)-pentan-1-ol (IV-3)

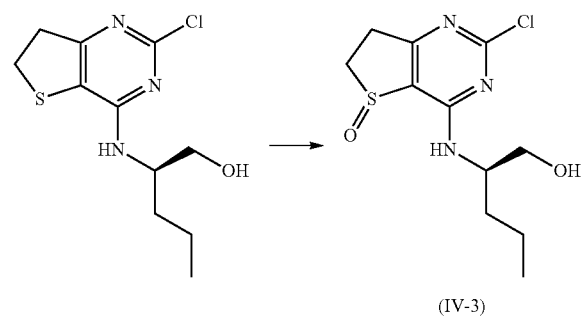 [SMILES: CCC[C@H](CO)Nc1nc(Cl)nc2c1SCC2 ; CCC[C@H](CO)Nc1nc(Cl)nc2c1S(=O)CC2 ; "(IV-3)"]

(IV-3)

0.3 g S-(−)-1,1'-Bi-2-naphthol are placed in 5 ml chloroform under argon, then 0.15 ml titanium(IV)-isopropoxide and 0.19 ml of water are added. The reaction mixture is stirred for 1 hour at ambient temperature. Then a suspension of 1.4 g (III-3) in 20 ml dichloromethane is added. The reaction mixture is cooled to −5° C. and after 30 minutes 0.95 ml tert-butylhydroperoxide 5-6 M in decane are added dropwise. The reaction mixture is stirred at −5° C. until there is no further reaction and made basic with NH$_4$OH. The product is extracted with dichloromethane and purified by chromatography (ethyl acetate/methanol 100/0 to 80/20). 1.17 g (IV-3) are obtained in the form of a solid. Analytical HPLC (method A): RT=2.41 min

3.3 (R)-2-{2-[4-(4-chlorophenyl)-piperidin-1-yl]-5-oxo-6,7-dihydro-5H-5λ$^4$-thieno[3,2-d]pyrimidin-4-ylamino}-pentan-1-ol Example 1.3

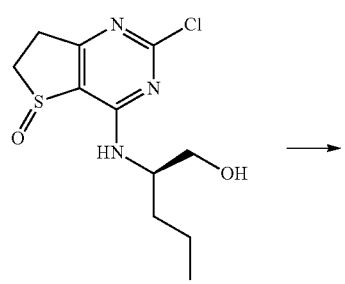

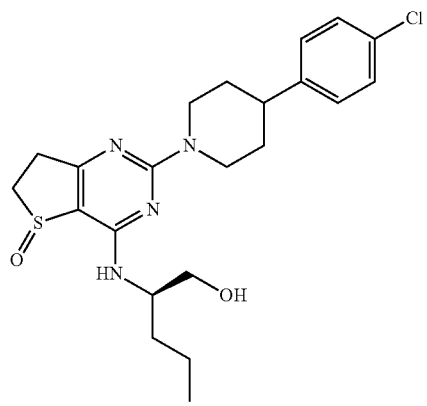

Example 1.3

0.2 g (IV-3) are placed in 4 ml dioxane and 237 µl diisopropylethylamine, combined with 0.149 g 4-(4-chlorophenyl)-piperidine and heated in the microwave for 30 min at 130° C. The reaction mixture is mixed with water and the product is extracted with dichloromethane. The residue is treated with acetonitrile in the ultrasound bath and the solid is suction filtered. 0.104 g Example 1.3 are obtained in the form of a solid. Analytical HPLC-MS (method A): RT=1.29 min.

4. SYNTHESIS OF (R)-1-{2-[4-(4-CHLOROPHENYL)-PIPERIDIN-1-YL]-5-OXO-6,7-DIHYDRO-5H-5λ$^4$-THIENO[3,2-D]PYRIMIDIN-4-YLAMINO}-1-(4-FLUOROPHENYL)-2-METHYLPROPAN-2-OL

Example 1.4

4.1 methyl (R)-amino-(4-fluorophenyl)-acetate

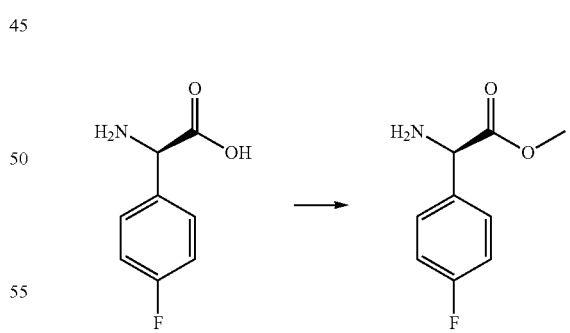

4 g (R)-4-fluorophenylglycine are suspended in 80 ml of methanol. While cooling with the ice bath 3.28 ml of thionyl chloride are slowly added dropwise, so that the temperature is maintained between 15° C. and 20° C. The reaction mixture is stirred for 12 hours at ambient temperature and then evaporated to dryness. 5.1 g of the product are obtained in the form of the hydrochloride. Analytical HPLC-MS (method A): RT=0.8 min.

4.2 methyl (R)-(4-fluorophenyl)-(2,2,2-trifluoroacetylamino)-acetate

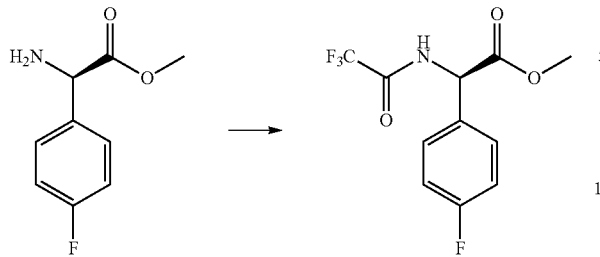

5.1 g methyl (R)-amino-(4-fluorophenyl)-acetate are placed in 36.5 ml abs. tetrahydrofuran, then 3.9 ml triethylamine are added. The reaction mixture is cooled to −70° C. 3.9 ml trifluoracetic anhydride are then slowly added dropwise, so that the temperature does not exceed −60° C. The reaction mixture is stirred for 12 hours at ambient temperature and then mixed with water. Then potassium hydrogen carbonate is added until there is no more foaming and the product is extracted with ethyl acetate. 6.2 g of the product are obtained in the form of an oil. Analytical HPLC-MS (method A): RT=1.28 min.

4.3 2,2,2-trifluoro-N—[(R)-1-(4-fluorophenyl)-2-hydroxy-2-methylpropyl]-acetamide

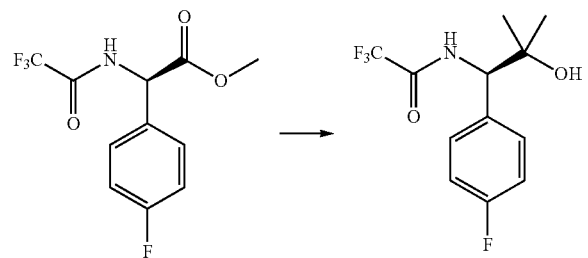 [SMILES: COC(=O)[C@H](NC(=O)C(F)(F)F)c1ccc(F)cc1 ; CC(C)(O)[C@H](NC(=O)C(F)(F)F)c1ccc(F)cc1]

6.2 g methyl (R)-(4-fluorophenyl)-(2,2,2-trifluoroacetylamino)-acetate are placed in 195 ml abs. tetrahydrofuran and the reaction mixture is cooled to +3° C. 37.2 ml of a methylmagnesium iodide solution (3 M) are slowly added dropwise, so that the temperature does not exceed +10° C. The reaction mixture is stirred for 12 hours at ambient temperature and then stirred into ice water. Ammonium chloride is added until the precipitate is dissolved and the product is extracted with ethyl acetate. 5.6 g of the product are obtained in the form of an oil. Analytical HPLC-MS (method A): RT=1.19 min

4.4 (R)-1-amino-1-(4-fluorophenyl)-2-methylpropan-2-ol

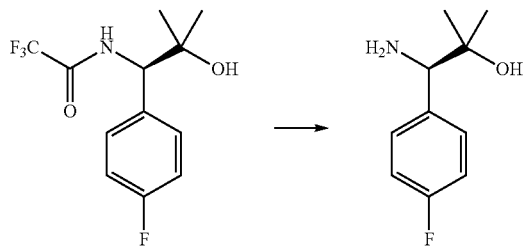 [SMILES: CC(C)(O)[C@H](NC(=O)C(F)(F)F)c1ccc(F)cc1 ; CC(C)(O)[C@H](N)c1ccc(F)cc1]

5.6 g of 2,2,2-trifluoro-N—[(R)-1-(4-fluorophenyl)-2-hydroxy-2-methylpropyl]-acetamide and 2.27 g KOH are suspended in 60 ml of methanol. The reaction mixture is stirred for 20 hours at 60° C., then mixed with water and the product is extracted with dichloromethane. 3.2 g product are obtained in the form of an oil. Analytical HPLC-MS (method A): RT=0.79 min.

4.5 (R)-1-(2-chloro-6,7-dihydrothieno[3,2-d]pyrimidin-4-ylamino)-1-(4-fluorophenyl)-2-methylpropan-2-ol (III-4)

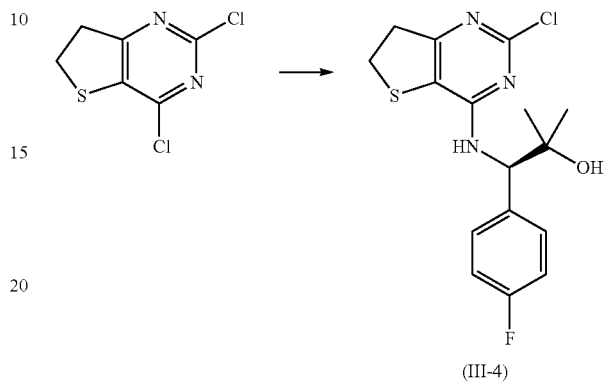

(III-4)

0.533 g (II), 0.850 g (R)-1-amino-1-(4-fluorophenyl)-2-methylpropan-2-ol and 1.3 ml diisopropylethylamine are suspended in 9.8 ml dioxane. The reaction mixture is heated in the microwave for 2 hours at 80° C. and then evaporated to dryness. The residue is mixed with water. The precipitate formed is suction filtered and purified by chromatography (silica gel, petroleum ether/ethyl acetate 100/0 to 60/40). 0.260 g (III-4) are obtained in the form of a solid. Analytical HPLC-MS (method A): 1.39 min.

4.6 (R)-1-(2-chloro-5-oxo-6,7-dihydro-5H-5$\lambda^4$-thieno[3,2-d]pyrimidin-4-ylamino)-1-(4-fluorophenyl)-2-methylpropan-2-ol (IV-4)

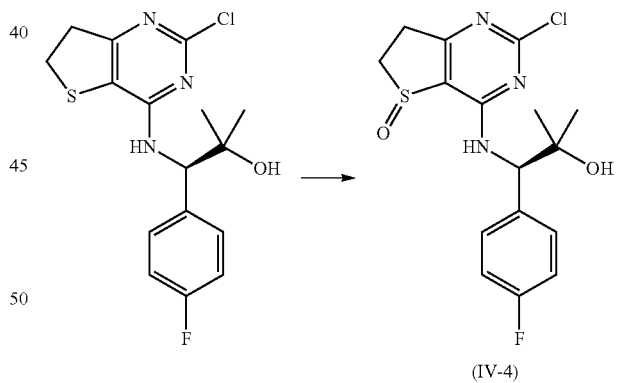

(IV-4)

0.24 g S-(−)-1,1'-Bi-2-naphthol are placed in 4 ml chloroform under argon, then 0.125 ml titanium(IV)-isopropoxide and 0.15 ml of water are added. The reaction mixture is stirred for 1 hour at ambient temperature. Then a suspension of 1.51 g (III-4) in 26 ml chloroform is added. The reaction mixture is cooled to −6° C. and after 30 minutes 0.78 ml tert-butylhydroperoxide 5-6 M in decane are added dropwise. The reaction mixture is stirred at −6° C. until there is no further reaction and made basic with $NH_4OH$. The product is extracted with dichloromethane and purified by chromatography (dichloromethane/methanol 100/0 to 95/5). 0.62 g (IV-4) are obtained in the form of a solid. Analytical HPLC-MS (method A): RT=1.19 min.

4.7 (R)-1-{2-[4-(4-chlorophenyl)-piperidin-1-yl]-5-oxo-6,7-dihydro-5H-5λ⁴-thieno[3,2-d]pyrimidin-4-ylamino}-1-(4-fluorophenyl)-2-methylpropan-2-ol Example 1.4

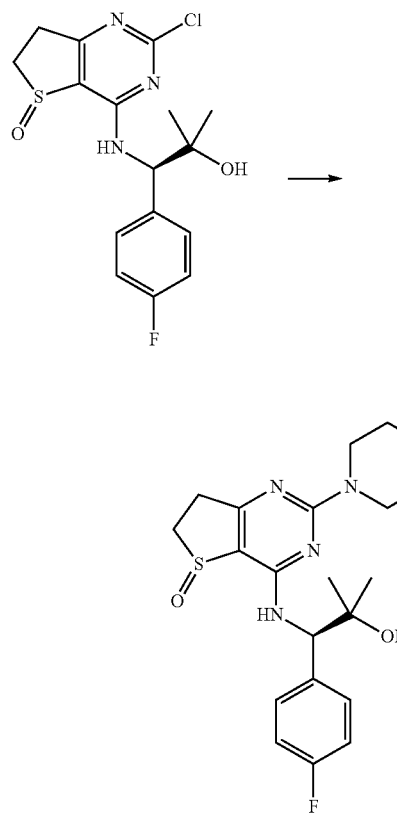

Eample 1.4

Starting from 0.24 g (IV-4) and 0.15 g 4-(4-chlorophenyl)-piperidine 0.19 g Example 1.4 are prepared analogously to Example 1.1 (cf. 1.3). The product is purified by chromatography (dichloromethane/methanol 100/0 to 96/4). Analytical HPLC-MS (method A): RT=1.36 min.

5. SYNTHESIS OF (S)-5-{2-[4-(4-CHLOROPHE-NYL)-PIPERIDIN-1-YL]-5-OXO-6,7-DIHYDRO-5H-5λ⁴-THIENO[3,2-D]PYRIMIDIN-4-YLAMINO}-1-METHYLPIPERIDIN-2-ONE

Example 1.5

5.1 (S)-5-dibenzylaminopiperidin-2-one

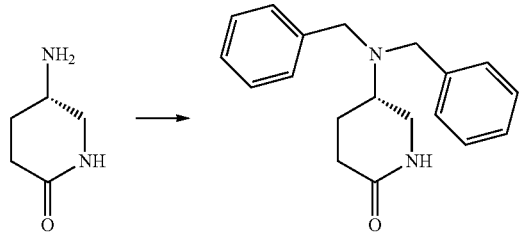 [SMILES: N[C@H]1CCC(=O)NC1 ; O=C1CC[C@H](N(Cc2ccccc2)Cc2ccccc2)CN1]

0.600 g 4-(S)-amino-delta-valerolactam hydrochloride, 0.970 ml benzylbromide and 1.5 g sodium hydrogen carbonate are suspended in 30 ml of ethanol. The reaction mixture is then stirred for 8 hours at 80° C. and then evaporated to dryness. The residue is suspended in water and the product is extracted with dichloromethane and purified by chromatography (silica gel, dichloromethane/methanol 100/0 to 95/5). 0.500 g product are obtained in the form of an oil. Analytical HPLC-MS (method A): RT=1.01 min.

5.2 (S)-5-dibenzylamino-1-methylpiperidin-2-one

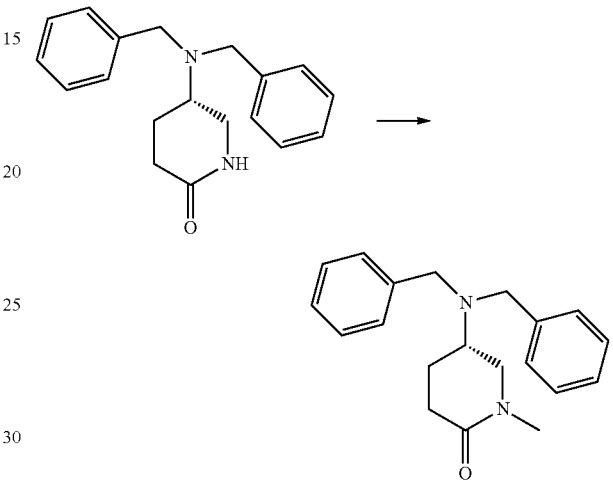

0.500 g (S)-5-dibenzylaminopiperidin-2-one are suspended in 15 ml of tetrahydrofuran. While cooling with the ice bath 0.175 g potassium-tert-butoxide are added. The reaction mixture is then stirred for 30 minutes at ambient temperature. While cooling with the ice bath 0.095 ml methyl iodide are added. The reaction mixture is then stirred for 48 hours at ambient temperature and then combined with a saturated NaCl solution. The product is extracted with ethyl acetate. 0.450 g product are obtained in the form of an oil. Analytical HPLC-MS (method A): RT=1.07 min.

5.3 (S)-5-amino-1-methylpiperidin-2-one

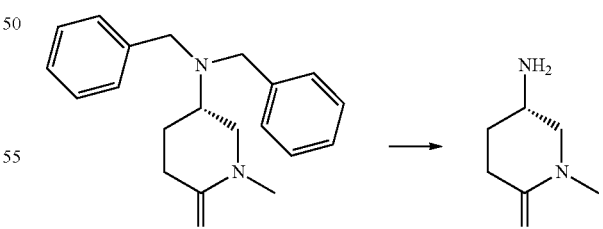

0.450 g (S)-5-dibenzylamino-1-methylpiperidin-2-one are suspended in 25 ml of methanol and hydrogenated with 0.150 g Pd/C 10% at a pressure of 3 bar and at a temperature of 60° C. After 16 hours the catalyst is removed by suction filtering and the filtrate is evaporated to dryness. 0.190 g of the product are obtained in the form of an oil. ¹H NMR (400 MHz, DMSO): 2.76 (3H, s).

5.4 (S)-5-(2-chloro-6,7-dihydrothieno[3,2-d]pyrimidin-4-ylamino)-1-methylpiperidin-2-one (III-5)

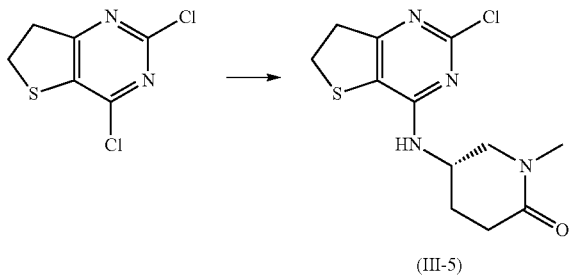 [SMILES: Clc1nc(Cl)c2c(n1)CCS2 ; CN1C[C@@H](Nc2nc(Cl)nc3c2SCC3)CCC1=O ; "(III-5)"]

(III-5)

0.27 g (II) are placed in 3 ml dioxane, then first 0.45 ml diisopropylethylamine are added, followed by 0.25 g (S)-5-amino-1-methylpiperidin-2-one. The reaction mixture is heated to 130° C. until there is no further reaction then cooled and evaporated down. The product is extracted with dichloromethane and purified by chromatography (preparative HPLC, method A). 0.26 g (III-5) are obtained in the form of a solid. Analytical HPLC-MS (method A): RT=1.06 min.

5.5 (S)-5-(2-chloro-5-oxo-6,7-dihydro-5H-5λ$^4$-thieno[3,2-d]pyrimidin-4-ylamino)-1-methylpiperidin-2-one (IV-5)

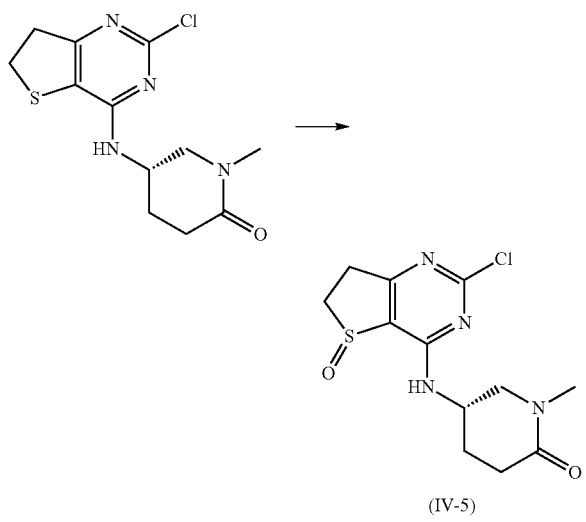

(IV-5)

0.04 g S-(−)-1,1'-bi-2-naphthol are placed in 5 ml chloroform under argon, then 0.02 ml titanium(IV)-isopropoxide and 0.025 ml of water are added. The reaction mixture is stirred for 1 hour at ambient temperature. Then a suspension of 0.2 g (III-5) in 4 ml dichloromethane is added. The reaction mixture is cooled to −5° C. and after 20 minutes 0.12 ml tert-butylhydroperoxide 5-6 M in decane are added dropwise. The reaction mixture is stirred at −5° C. until there is no further reaction and made basic with NH$_4$OH. The product is purified by chromatography (silica gel, ethyl acetate/methanol 100/0 to 60/40). 0.09 g (IV-5) are obtained in the form of a solid. Analytical HPLC-MS (method A): RT=0.83 min.

5.6 (S)-5-{2-[4-(4-chlorophenyl)-piperidin-1-yl]-5-oxo-6,7-dihydro-5H-5λ$^4$-thieno[3,2-d]pyrimidin-4-ylamino}-1-methylpiperidin-2-one Example 1.5

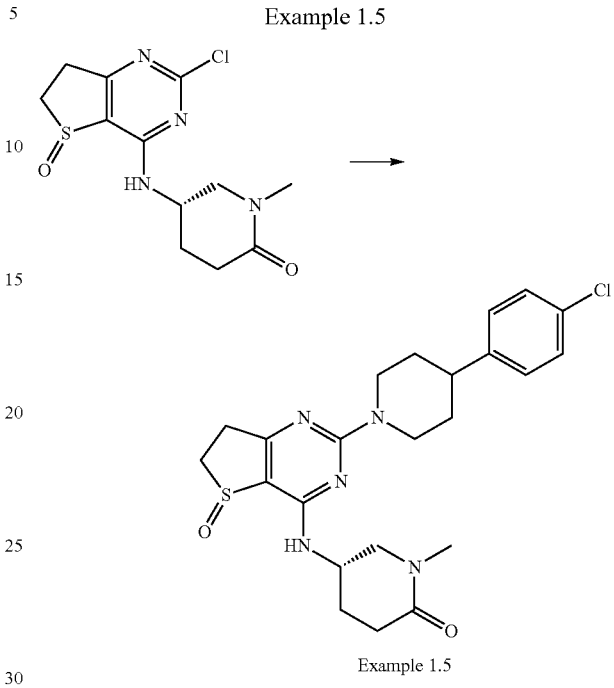

Example 1.5

Starting from 0.2 g (IV-5) and 0.18 g 4-(4-chlorophenyl)-piperidine, 0.17 g Example 1.5 are prepared analogously to Example 1.1 (cf. 1.3). The product is purified by chromatography (preparative HPLC, method A). The product fractions are made basic with ammonia and freeze-dried. Analytical HPLC-MS (method A): RT=1.18 min

6. SYNTHESIS OF {2-[4-(4-CHLOROPHENYL)-PIPERIDIN-1-YL]-5-OXO-6,7-DIHYDRO-5H-5λ$^4$-THIENO[3,2-D]PYRIMIDIN-4-YL}-(TETRAHYDROPYRAN-4-YL)-AMINE

Example 1.6

6.1 (2-chloro-6,7-dihydrothieno[3,2-d]pyrimidin-4-yl)-(tetrahydropyran-4-yl)-amine (III-6)

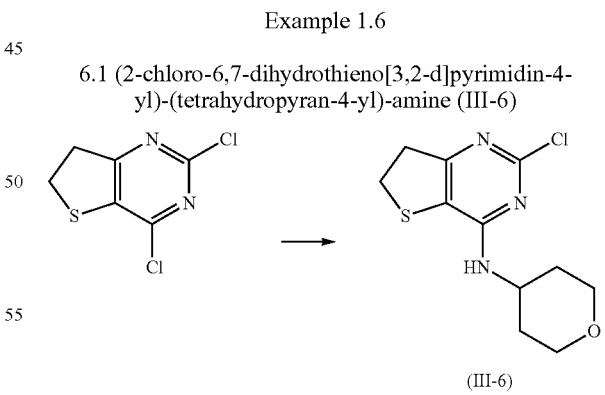

(III-6)

0.68 g (II) are placed in 6 ml dioxane, then first 1.72 ml diisopropylethylamine are added, followed by 0.6 g of 4-aminotetrahydropyran. The reaction mixture is heated to 130° C. until there is no further reaction then cooled and evaporated down. The product is treated with water in the ultrasound bath, then suction filtered and dried. 0.66 g (III-6) are obtained in the form of a solid. Analytical HPLC-MS (method C): RT=1.08 min.

6.2 (2-chloro-5-oxo-6,7-dihydro-5H-5λ⁴-thieno[3,2-d]pyrimidin-4-yl)-(tetrahydropyran-4-yl)-amine (IV-6)

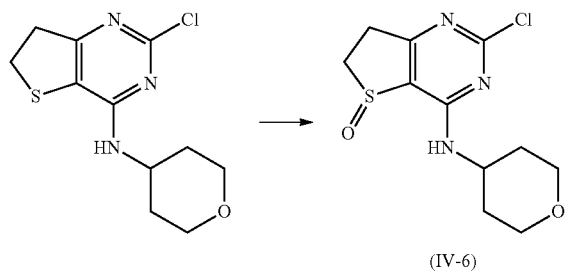 [SMILES: Clc1nc2c(c(NC3CCOCC3)n1)SCC2 ; O=S1CCc2nc(Cl)nc(NC3CCOCC3)c21 ; "(IV-6)"]

(IV-6)

0.14 g S-(−)-1,1'-Bi-2-naphthol are placed in 5 ml chloroform under argon, then 0.072 ml titanium(IV)-isopropoxide and 0.087 ml of water are added. The reaction mixture is stirred for 45 minutes at ambient temperature. Then a suspension of 0.66 g (III-6) in 25 ml chloroform is added. The reaction mixture is cooled to −10° C. and after 60 minutes 0.444 ml tert-butylhydroperoxide 5-6 M in decane are added dropwise. The reaction mixture is stirred at −10 to −4° C. until there is no further reaction and mixed with water. The product is extracted with dichloromethane and purified by chromatography (silica gel, ethyl acetate/methanol 100/0 to 80/20). 0.42 g (IV-6) are obtained in the form of a solid. Analytical HPLC-MS (method A): RT=0.94 min.

6.3 {2-[4-(4-chlorophenyl)-piperidin-1-yl]-5-oxo-6,7-dihydro-5H-5λ4-thieno[3,2-d]pyrimidin-4-yl}-(tetrahydropyran-4-yl)-amine Example 1.6

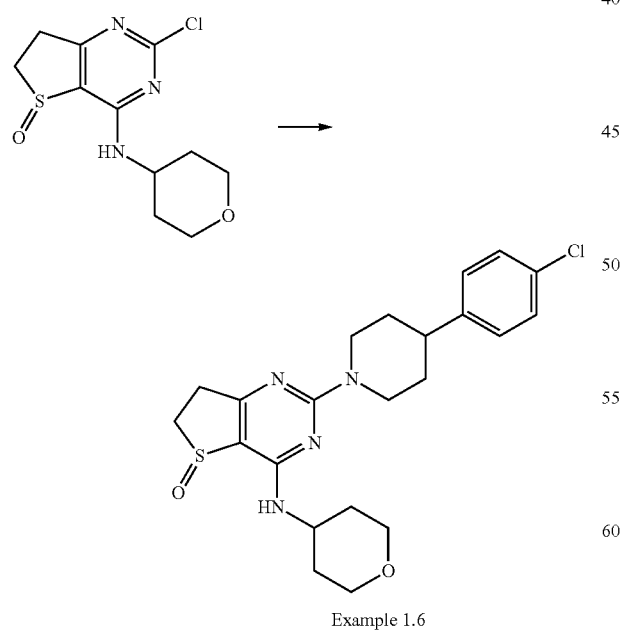

Example 1.6

Starting from 0.18 g (IV-6) and 0.17 g 4-(4-chlorophenyl)-piperidine 0.23 g Example 1.6 are prepared analogously to Example 1.1 (cf. 1.3). The product is treated with water in the ultrasound bath and the solid is suction filtered. Analytical HPLC-MS (method A): RT=1.24 min

7. SYNTHESIS OF 1-(4-(1-HYDROXYMETHYL-CYCLOPROPYLAMINO)-5-OXO-6,7-DIHYDRO-5H-5λ⁴-THIENO[3,2-D]PYRIMIDIN-2-YL)-3'-METHYL-1'H-SPIRO[PIPERIDIN-4,4'-QUINAZOLIN]-2'(3'H)-ONE

Example 1.7

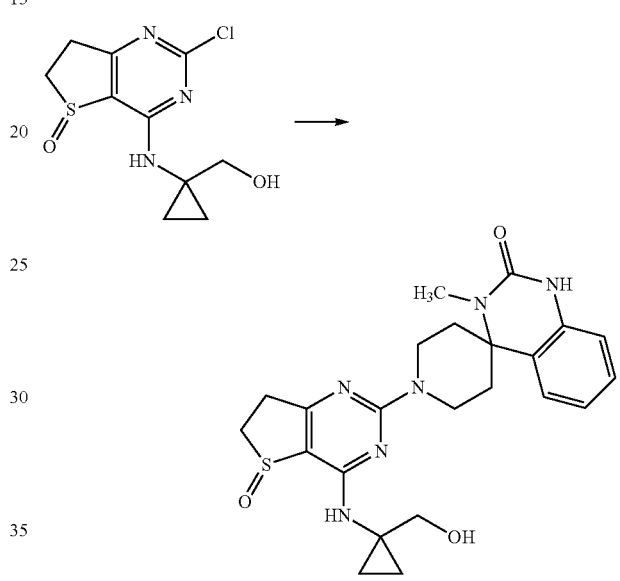

Example 1.7

Starting from (IV-2) (cf. 2.4) and 3'-methyl-1'H-spiro[piperidin-4,4'-quinazolin]-2'(37-1)-one (*Chem. Pharm. Bull.* 1988, 4659) (0.1 mmol) mixed in 400 μl NMP and the mixture is heated to 120° C. for 30 min in the microwave. Then 600 μL DMF are added, the reaction solution is purified by preparative HPLC-MS (method A) and the product fractions are freeze-dried. Analytical HPLC-MS (method C): RT=1.52 min.

8. SYNTHESIS OF {1-[2-(4-BENZO[d]ISOXAZOL-3-YL-PIPERIDIN-1-YL)-5-OXO-6,7-DIHYDRO-5H-5λ⁴-THIENO[3,2-D]PYRIMIDIN-4-YLAMINO]-CYCLOPROPYL}-METHANOL

Example 1.8

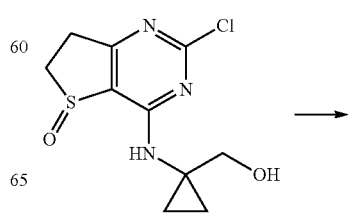

-continued

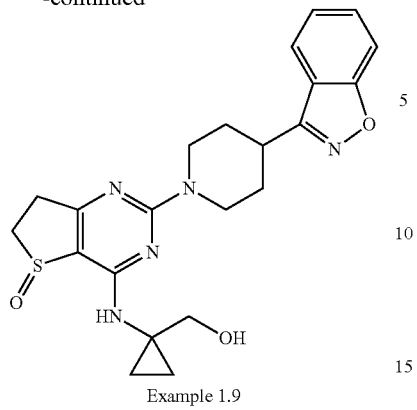

Example 1.9

Starting from (IV-2) (cf. 2.4) and 3-piperidin-4-yl-benzo[d]isoxazole, Example 1.8 can be prepared and purified analogously to Example 1.7 (cf. 7.). Analytical HPLC-MS (method C): RT=1.7 min.

9. SYNTHESIS OF (1-{2-[4-(2-ETHYL-5-FLUORO-1H-INDOL-3-YL)-PIPERIDIN-1-YL]-5-OXO-6,7-DIHYDRO-5H-5λ⁴-THIENO[3,2-D]PYRIMIDIN-4-YLAMINO}-CYCLOPROPYL)-METHANOL

Example 1.9

9.1 2-but-1-ynyl-4-fluorophenylamine

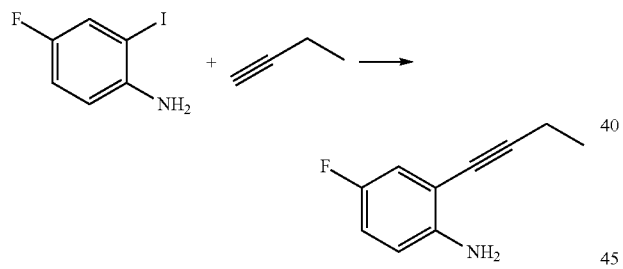

80 ml of tetrahydrofuran is placed under argon. 5 g 4-fluoro-2-iodophenylamine, 0.74 g dichlorobis(triphenylphosphine) palladium(II), 0.2 g copper iodide and 8.8 ml triethylamine are added. 4 g gaseous 1-butyne are passed through the suspension. The reaction mixture is stirred under argon for 15 hours at ambient temperature, then filtered through Celite and evaporated to dryness. 3.4 g product are obtained in the form of a solid. ¹H NMR (400 MHz, DMSO): 2.45 (2H, q); 1.18 (3H, t).

9.2 2-ethyl-5-fluoro-1H-indole

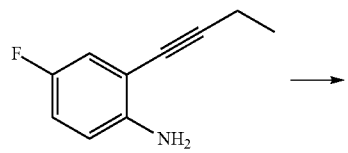

-continued

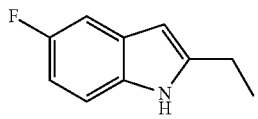

Under argon 4.9 g potassium-tert-butoxide are suspended in 25 ml N-methyl-2-pyrrolidinone and a suspension of 3.4 g 2-but-1-ynyl-4-fluorophenylamine in 25 ml N-methyl-2-pyrrolidinone is added dropwise thereto. The reaction mixture is stirred for 3 hours at ambient temperature and mixed with water. The product is extracted with diethyl ether and purified by chromatography (silica gel, cyclohexane/ethyl acetate 100/0-90/10). 2.83 g product are obtained in the form of a solid. ¹H NMR (400 MHz, DMSO): 2.72 (2H, q); 1.27 (3H, t).

9.3 2-ethyl-5-fluoro-3-(1.2.3.6-tetrahydropyridin-4-yl)-1H-indole

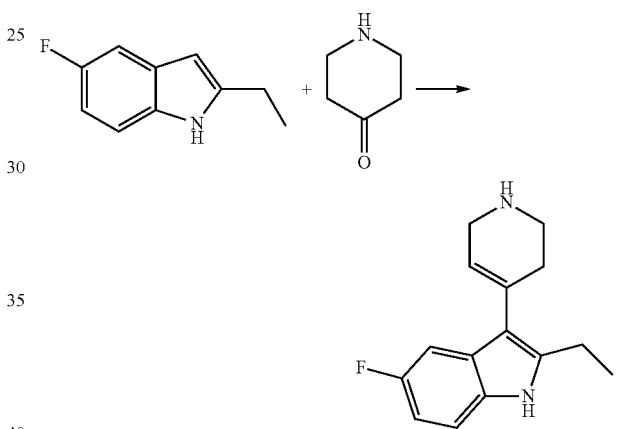

2.83 g 2-ethyl-5-fluoro-1H-indole are suspended in 50 ml acetic acid and heated to 90° C. A suspension of 6.66 g 4-piperidone in 15 ml phosphoric acid 2N is added. The reaction mixture is stirred for 3 hours at 90° C., combined with sodium hydroxide solution and the product is extracted with ethyl acetate. 2.85 g product are obtained in the form of a solid. ¹H NMR (400 MHz, DMSO): 5.63 (1H, s); 2.73 (2H, q); 1.23 (3H, t).

9.4 2-ethyl-5-fluoro-3-piperidin-4-yl-1H-indole (V-1)

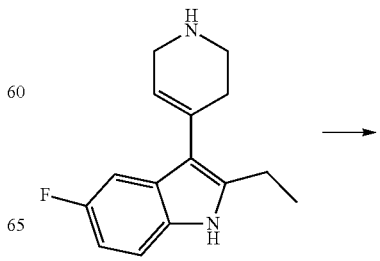

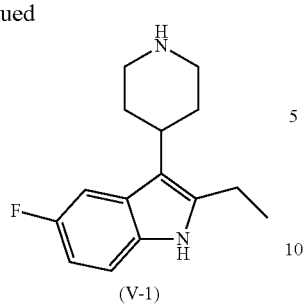

(V-1)

2.83 g 2-ethyl-5-fluoro-3-(1.2.3.6-tetrahydropyridin-4-yl)-1H-indole are suspended in 50 ml of methanol and hydrogenated with 0.3 g Pd/C 10% at normal pressure and ambient temperature. The catalyst is suction filtered and the filtrate is evaporated to dryness. 2.3 g (V-1) are obtained in the form of a solid. $^1$H NMR (400 MHz, DMSO): 2.70 (2H, q); 1.19 (3H, t).

9.5 (1-{2-[4-(2-ethyl-5-fluoro-1H-indol-3-yl)-piperidin-1-yl]-5-oxo-6,7-dihydro-5H-5$\lambda^4$-thieno[3,2-d]pyrimidin-4-ylamino}-cyclopropyl)-methanol Example 1.9

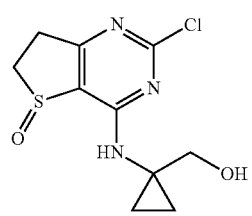

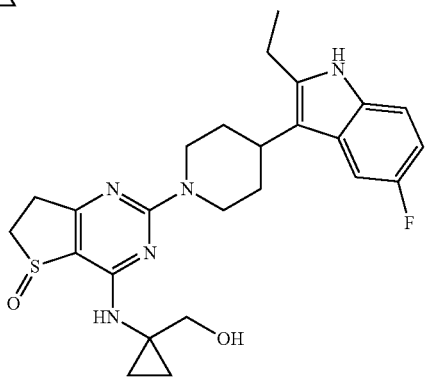

Example 1.9

Starting from (IV-2) (cf. 2.4) and (V-1) Example 1.9 can be prepared and purified analogously to Example 1.7 (cf. 7.). Analytical HPLC-MS (method C): RT=1.78 min.

10. SYNTHESIS OF 1-[4-((S)-1-METHYL-6-OXOPIPERIDIN-3-YLAMINO)-5-OXO-6,7-DIHYDRO-5H-5$\lambda^4$-THIENO[3,2-D]PYRIMIDIN-2-YL]-4-PHENYLPIPERIDINE-4-CARBONITRILE Example 1.10

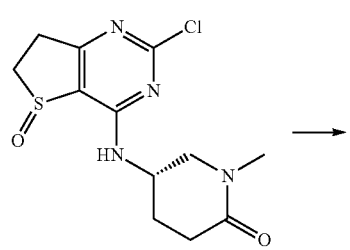

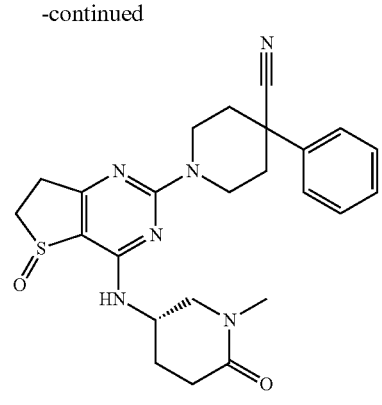

Example 1.10

Starting from (IV-5) (cf. 5.5) and 4-phenylpiperidine-4-carbonitrile Example 1.10 can be prepared and purified analogously to Example 1.7 (cf. 7). Analytical HPLC-MS (method C): RT=1.71 min.

11. SYNTHESIS OF 3'-METHYL-1-(4-(TETRAHYDRO-2H-PYRAN-4-YLAMINO)-5-OXO-6,7-DIHYDRO-5H-5$\lambda^4$-THIENO[3,2-D]PYRIMIDIN-2-YL)-1'H-SPIRO[PIPERIDIN-4,4'-QUINAZOLIN]-2'(3'H)-ONE Example 1.11

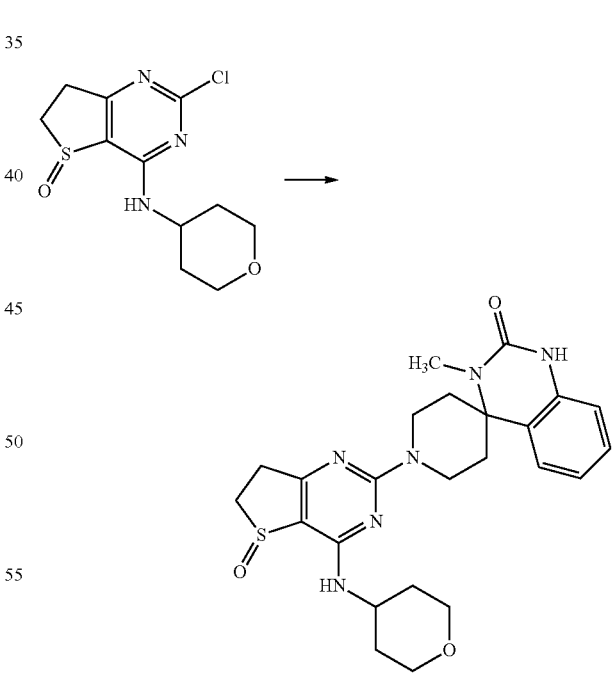

Example 1.11

Starting from (IV-6) (cf. 6.2) and 3'-methyl-1'H-spiro[piperidin-4,4'-quinazolin]-2'(37-1)-one (*Chem. Pharm. Bull.* 1988, 4659) Example 1.11 can be prepared and purified analogously to Example 1.7 (cf. 7.). Analytical HPLC-MS (method C): RT=1.56 min.

12. SYNTHESIS OF (3-FLUOROPHENYL)-[5-OXO-2-(3,4,5,6-TETRAHYDRO-2H-[4,4']BIPYRIDINYL-1-YL)-6,7-DIHYDRO-5H-5λ⁴-THIENO[3,2-D]PYRIMIDIN-4-YL]-AMINE

Example 1.12

12.1 (2-chloro-6,7-dihydrothieno[3,2-d]pyrimidin-4-yl)-(3-fluorophenyl)-amine (III-7)

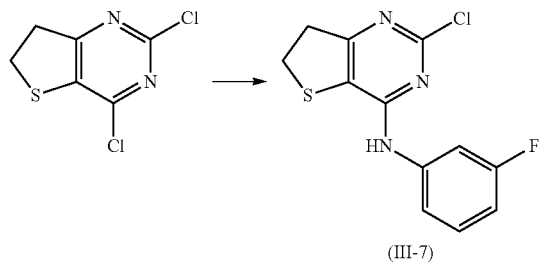

(III-7)

4 g (II) are placed in 15 ml dimethylformamide, then 4.5 ml diisopropylethylamine are added followed by 2.5 ml 3-fluorophenylamine. The reaction mixture is heated to 120° C. until there is no further reaction then cooled and evaporated down. The residue is mixed with water. The product is extracted with dichloromethane and purified by chromatography (silica gel, petroleum ether/ethyl acetate 80/20 to 60/40). 2.6 g (III-7) are obtained in the form of a solid. Analytical HPLC (method A): RT=3.27 min

12.2 2-chloro-5-oxo-6,7-dihydro-5H-5λ⁴-thieno[3,2-d]pyrimidin-4-yl)-(3-fluorophenyl)-amine (IV-7)

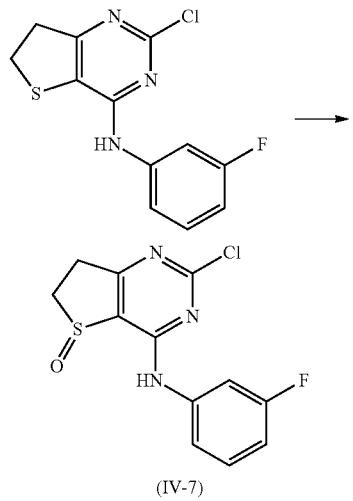

(IV-7)

0.102 g S-(−)-1,1'-bi-2-naphthol are placed in 0.5 ml chloroform under argon, then 0.052 ml titanium(IV)-isopropoxide and 0.064 ml of water are added. The reaction mixture is stirred for 45 minutes at ambient temperature. Then a suspension of 0.5 g (III-7) in 25 ml chloroform is added. The reaction mixture is cooled to −2°/−4° C. and after 20 minutes 0.323 ml tert-butylhydroperoxide 5-6 M in decane are added dropwise. The reaction mixture is stirred at −2/−4° C. until there is no further reaction and mixed with water. The product is extracted with dichloromethane and purified by chromatography (silica gel, dichloromethane/methanol 100/0 to 95/5). 0.47 g (IV-7) are obtained in the form of a solid. Analytical HPLC-MS (method A): RT=1.15 min.

12.3 (3-fluorophenyl)-[5-oxo-2-(3,4,5,6-tetrahydro-2H-[4,4]bipyridinyl-1-yl)-6,7-dihydro-5H-5λ⁴-thieno[3,2-d]pyrimidin-4-yl]-amine Example 1.12

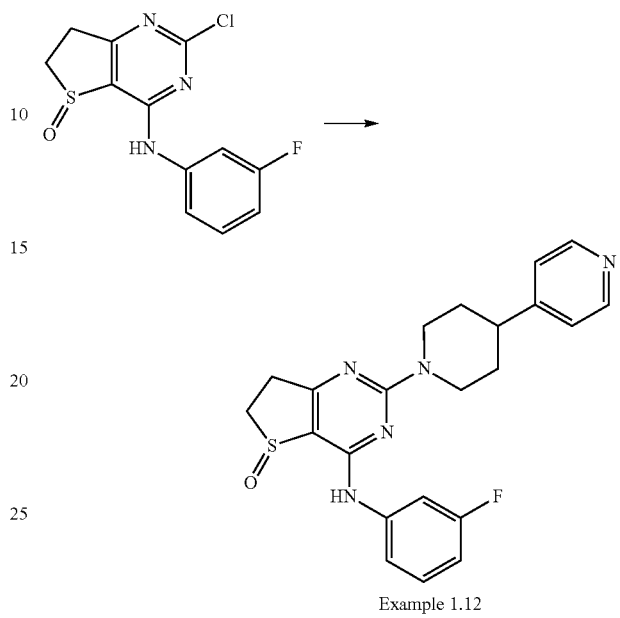

Example 1.12

Starting from (IV-7) (cf. 12.2) and 1,2,3,4,5,6-hexahydro-[4,4]bipyridinyl Example 1.12 can be prepared and purified as the trifluoroacetate analogously to Example 1.7 (cf. 7.). Analytical HPLC-MS (method C): RT=1.55 min.

13. SYNTHESIS OF {2-[4-(2-ETHYL-5-FLUORO-1H-INDOL-3-YL)-PIPERIDIN-1-YL]-5-OXO-6,7-DIHYDRO-5H-5λ⁴-THIENO[3,2-D]PYRIMIDIN-4-YL}-(3-FLUOROPHENYL)-AMINE

Example 1.13

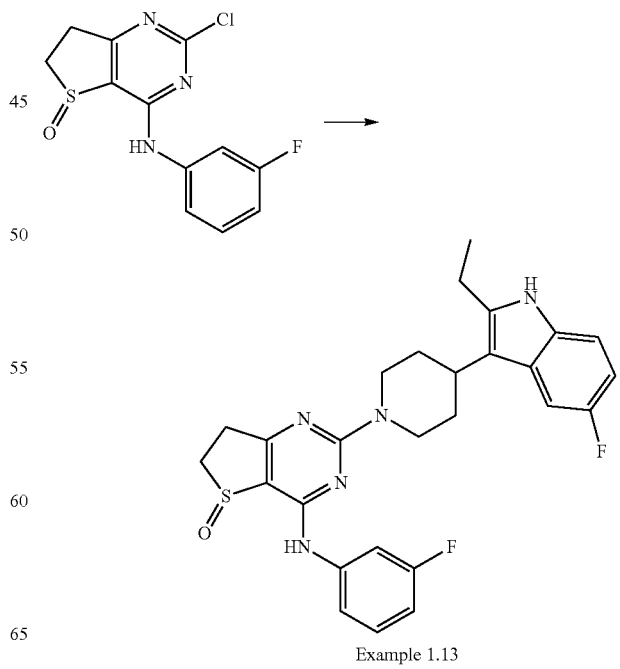

Example 1.13

Starting from (IV-7) (cf. 12.2) and (V-1) (cf. 9.4) Example 1.13 can be prepared and purified analogously to Example 1.7 (cf. 7.). Analytical HPLC-MS (method C): RT=2.12 min.

14. SYNTHESIS OF (1-{2-[4-(2,4-DIFLUOROPHENYL)-PIPERIDIN-1-YL]-5-OXO-6,7-DIHYDRO-5H-5λ⁴-THIENO[3,2-D]PYRIMIDIN-4-YLAMINO}-CYCLOPROPYL)-METHANOL

Example 1.14

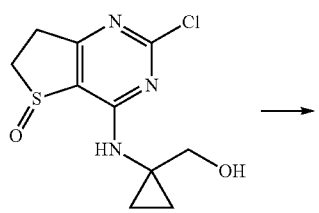

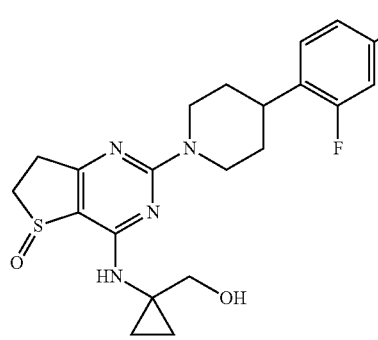

Example 1.14

Starting from (IV-2) (cf. 2.4) and 4-(2,4-difluorophenyl)-piperidine Example 1.14 may be prepared analogously to Example 1.7 (cf. 7.). The product may be purified by chromatography (preparative HPLC, method B). Analytical HPLC-MS (method D): RT=1.18 min.

15. SYNTHESIS OF {2-[4-(2,4-DIFLUOROPHENYL)-PIPERIDIN-1-YL]-5-OXO-6,7-DIHYDRO-5H-5λ⁴-THIENO[3,2-D]PYRIMIDIN-4-YL}-(TETRAHYDROPYRAN-4-YL)-AMINE

Example 1.15

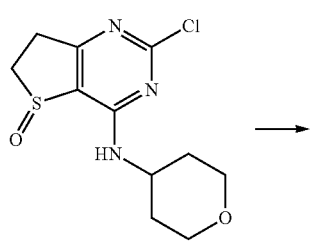

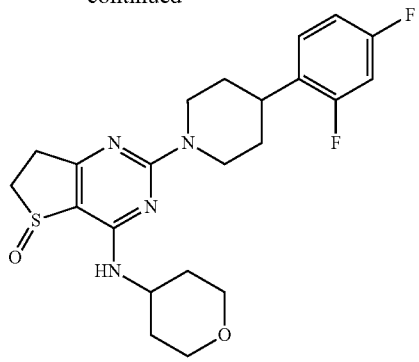

Example 1.15

Starting from (IV-6) (cf. 6.2) and 4-(2,4-difluorophenyl)-piperidine Example 1.15 can be prepared and purified analogously to Example 1.14 (cf. 14.). Analytical HPLC-MS (method D): RT=1.23 min.

16. SYNTHESIS OF (S)-5-[2-(4-BENZOXAZOL-2-YL-PIPERIDIN-1-YL)-5-OXO-6,7-DIHYDRO-5H-5λ⁴-THIENO[3,2-D]PYRIMIDIN-4-YLAMINO]-1-METHYLPIPERIDIN-2-ONE

Example 1.16

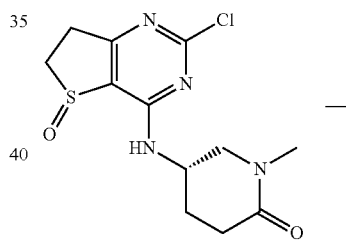

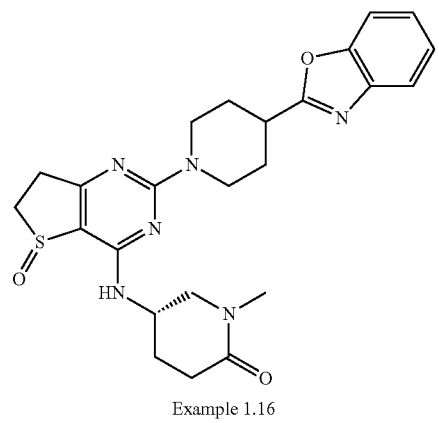

Example 1.16

Starting from (IV-5) (cf. 5.5) and 2-piperidin-4-yl-benzoxazole Example 1.16 can be prepared and purified analogously to Example 1.14 (cf. 14.). Analytical HPLC-MS (method B): RT=1.18 min.

17. SYNTHESIS OF (1-{2-[4-(6-FLUOROBENZO[d]ISOXAZOL-3-YL)-PIPERIDIN-1-YL]-5-OXO-6,7-DIHYDRO-5H-5λ⁴-THIENO[3,2-D]PYRIMIDIN-4-YLAMINO}-CYCLOPROPYL)-METHANOL

Example 1.17

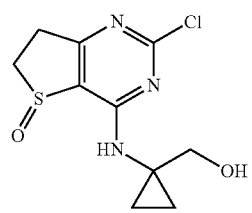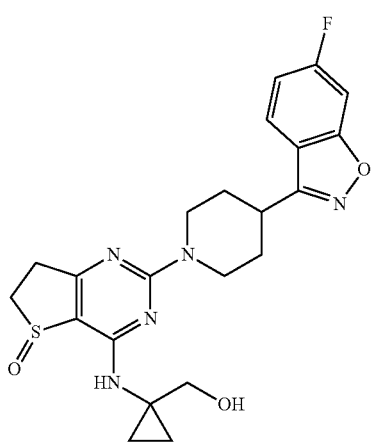

Example 1.17

Starting from (IV-2) (cf. 2.4) and 6-fluoro-3-piperidin-4-yl-benzo[d]isoxazole

Example 1.17 can be prepared and purified analogously to Example 1.7 (cf. 7.). Analytical HPLC-MS (method C): RT=1.76 min.

18. SYNTHESIS OF (1-{2-[4-(5-FLUOROBENZO[d]ISOXAZOL-3-YL)-PIPERIDIN-1-YL]-5-OXO-6,7-DIHYDRO-5H-5λ⁴-THIENO[3,2-D]PYRIMIDIN-4-YLAMINO}-CYCLOPROPYL)-METHANOL

Example 1.18

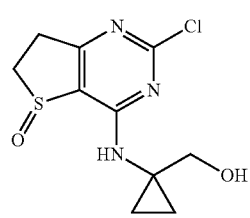

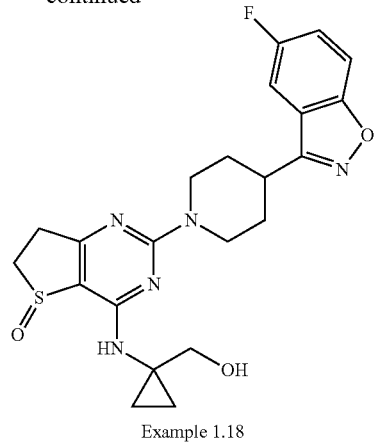

Example 1.18

Starting from (IV-2) (cf. 2.4) and 5-fluoro-3-piperidin-4-yl-benzo[d]isoxazole

Example 1.17 can be prepared and purified analogously to Example 1.7 (cf. 7.). Analytical HPLC-MS (method C): RT=1.74 min.

19. SYNTHESIS OF {2-[4-(5-FURAN-2-YL-2H-PYRAZOL-3-YL)-PIPERIDIN-1-YL]-5-OXO-6,7-DIHYDRO-5H-5λ⁴-THIENO[3,2-D]PYRIMIDIN-4-YL}-(TETRAHYDROPYRAN-4-YL)-AMINE

Example 1.19

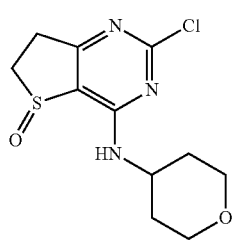

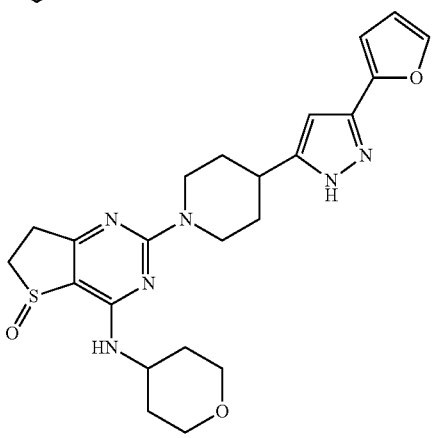

Example 1.19

Starting from (IV-6) (cf. 6.2) and 4-(5-furan-2-yl-2H-pyrazol-3-yl)-piperidine Example 1.19 can be prepared and purified analogously to Example 1.11 (cf. 11.). Analytical HPLC-MS (method C): RT=1.64 min.

20. SYNTHESIS OF (3-FLUOROPHENYL)-{5-OXO-2-[4-(3-PYRIDIN-4-YL-[1,2,4]OXADIAZOL-5-YL)-PIPERIDIN-1-YL]-6,7-DIHYDRO-5H-5λ⁴-THIENO[3,2-D]PYRIMIDIN-4-YL}-AMINE

Example 1.20

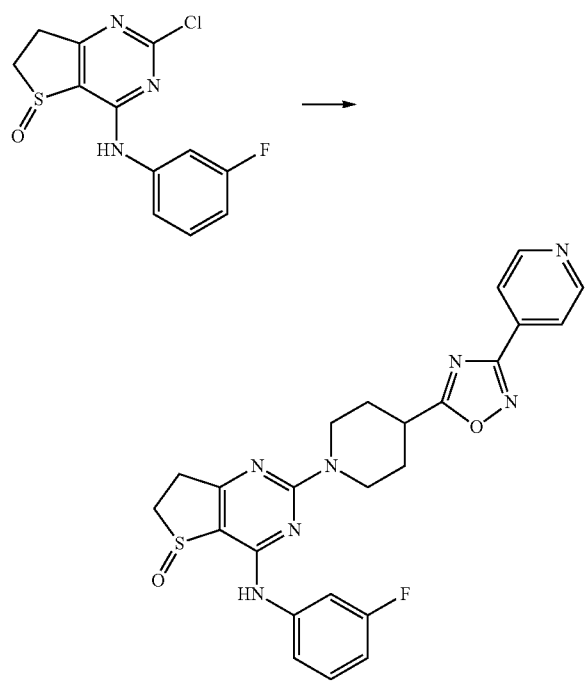

Example 1.20

Starting from (IV-7) (cf. 12.2) and 4-(5-piperidin-4-yl-[1,2,4]oxadiazol-3-yl)-pyridine Example 1.20 can be prepared and purified as the trifluoroacetate analogously to Example 1.7 (cf. 7.). Analytical HPLC-MS (method C): RT=1.72 min.

21. SYNTHESIS OF (R)-3-METHYL-2-15-OXO-2-[4-(3-PYRIDIN-4-YL-[1,2,4]OXADIAZOL-5-YL)-PIPERIDIN-1-YL]-6,7-DIHYDRO-5H-5λ⁴-THIENO[3,2-D]PYRIMIDIN-4-YLAMINO)-BUTAN-1-OL

Example 1.21

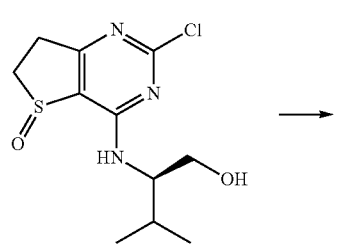

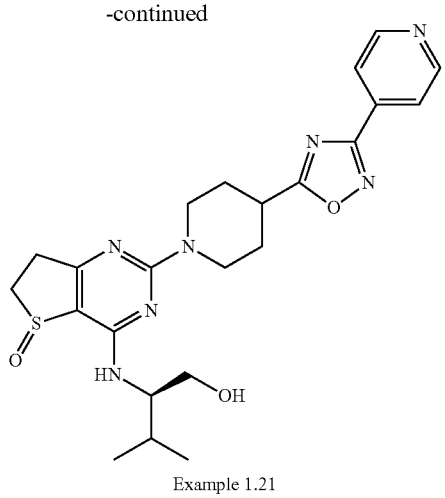

Example 1.21

Starting from (IV-1) (cf. 1.2) and 4-(5-piperidin-4-yl-[1,2,4]oxadiazol-3-yl)-pyridine Example 1.21 can be prepared and purified as the trifluoroacetate analogously to Example 1.7 (cf. 7.). Analytical HPLC-MS (method C): RT=1.48 min.

22. SYNTHESIS OF: (S)-5-{2-[4-(4-FLUOROPHENOXY)-PIPERIDIN-1-YL]-5-OXO-6,7-DIHYDRO-5H-5λ⁴-THIENO[3,2-D]PYRIMIDIN-4-YLAMINO}-1-METHYLPIPERIDIN-2-ONE

Example 1.22

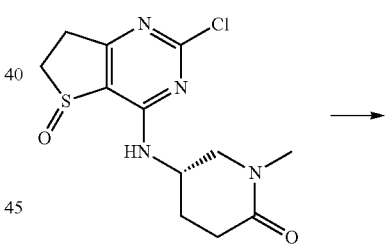

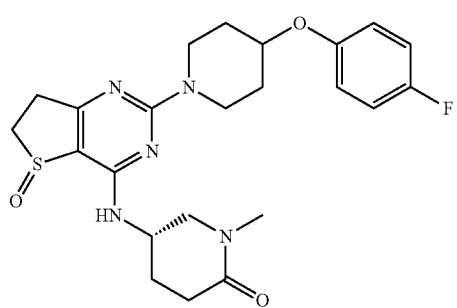

Example 1.22

Starting from (IV-5) (cf. 5.5) and 4-(4-fluorophenoxy)-piperidine Example 1.22 can be prepared and purified analogously to Example 1.16 (cf. 16.). Analytical HPLC-MS (method A): RT=1.15 min.

23. SYNTHESIS OF: (2-{4-[4-(4,5-DIHYDROOX-AZOL-2-YL)-PHENOXY]-PIPERIDIN-1-YL}-5-OXO-6,7-DIHYDRO-5H-5λ⁴-THIENO[3,2-D]PY-RIMIDIN-4-YL)-(TETRAHYDROPYRAN-4-YL)-AMINE

Example 1.23

23.1 tert-butyl 4-(toluene-4-sulphonyloxy)-piperidine-1-carboxylate

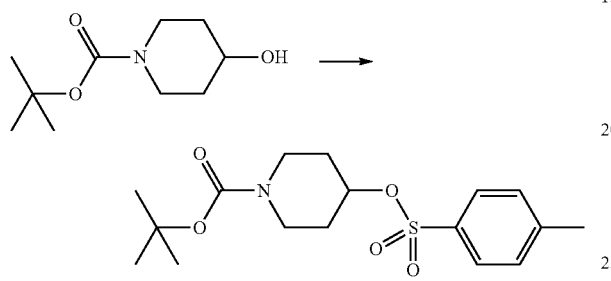

5 g tert-butyl 4-hydroxypiperidine-1-carboxylate are placed in 15 ml of pyridine, then 4.7 g p-toluenesulphonyl chloride are added batchwise. The reaction mixture is stirred at ambient temperature, after 12 hours it is poured onto ice water and the mixture obtained is stirred for a further hour at ambient temperature. The precipitated solid is suction filtered and dried. 7.5 g product are obtained.

23.2 tert-butyl 4-[4-(4,5-dihydrooxazol-2-yl)-phenoxy]-piperidine-1-carboxylate

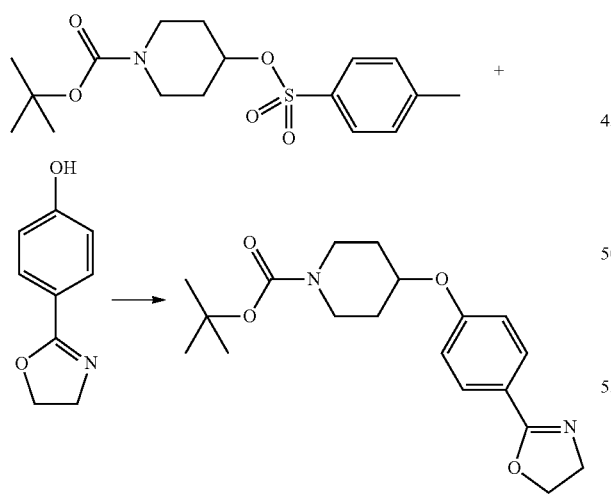

2.0 g 4-(4,5-dihydroxazol-2-yl)-phenol (cf. U.S. Pat. No. 5,491,201) are placed in 30 ml dimethylformamide, then 3.3 g potassium carbonate and 4.2 g tert-butyl 4-(toluene-4-sulphonyloxy)-piperidine-1-carboxylate are added. The reaction mixture is stirred at 75° C., after 12 hours it is mixed with water and the precipitated solid is suction filtered and dried. 2.8 g product are obtained.

23.3 4-[4-(4,5-dihydrooxazol-2-yl)-phenoxy]-piperidine (V-2)

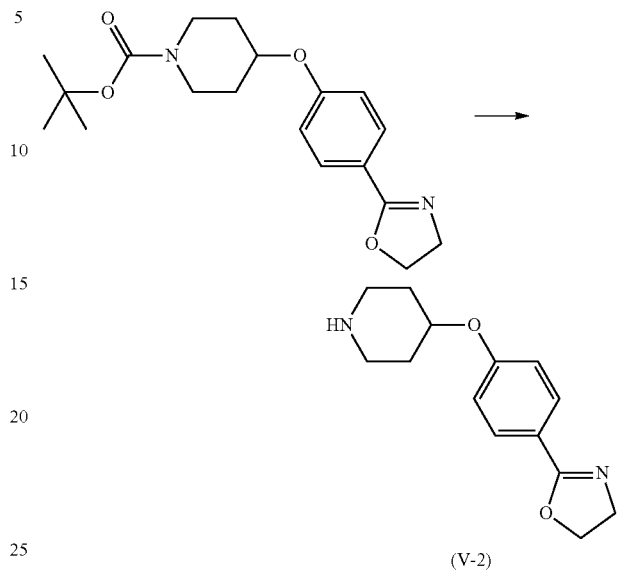

50 mg tert-butyl 4-[4-(4,5-dihydrooxazol-2-yl)-phenoxy]-piperidine-1-carboxylate are taken and mixed with 6 ml of a (5/1) dichloromethane/trifluoroacetic acid mixture. The reaction mixture is stirred at ambient temperature and after 15 min it is cautiously mixed with a saturated NaHCO₃ solution. The organic phase is dried and evaporated to dryness. 20 mg (V-2) are obtained.

23.4 (2-{4-[4-(4,5-dihydrooxazol-2-yl)-phenoxy]-piperidin-1-yl}-5-oxo-6,7-dihydro-5H-5λ⁴-thieno[3,2-d]pyrimidin-4-yl)-(tetrahydropyran-4-yl)-amine Example 1.23

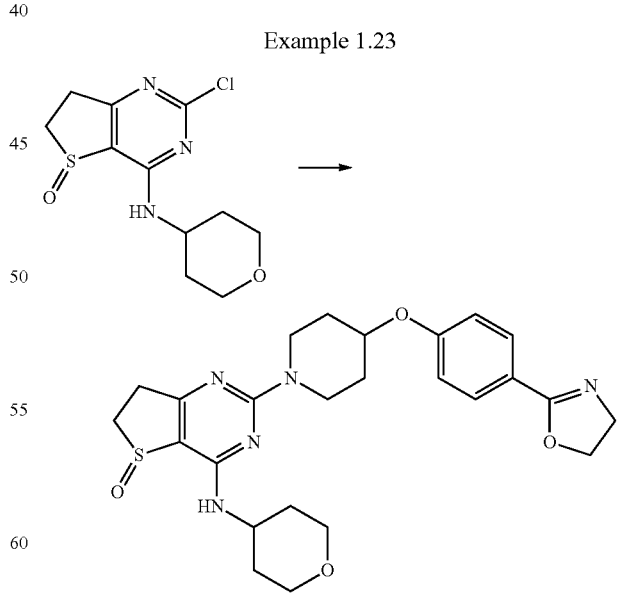

Example 1.23

Starting from (IV-6) (cf. 6.2) and (V-2) Example 1.23 can be prepared and purified analogously to Example 1.14 (cf. 14.). Analytical HPLC-MS (method A): RT=0.99 min.

24. SYNTHESIS OF: 4-{1-[5-OXO-4-(TETRAHYDROPYRAN-4-YLAMINO)-6,7-DIHYDRO-5H-5λ⁴-THIENO[3,2-D]PYRIMIDIN-2-YL]-PIPERIDIN-4-YLOXY}-BENZOIC ACID

Example 1.24

24.1 methyl 4-{1-[5-oxo-4-(tetrahydropyran-4-ylamino)-6,7-dihydro-5H-5λ⁴-thieno[3,2-d]pyrimidin-2-yl]-piperidin-4-yloxy}-benzoate

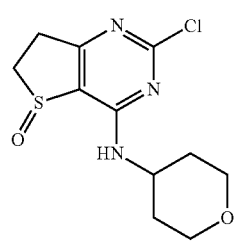
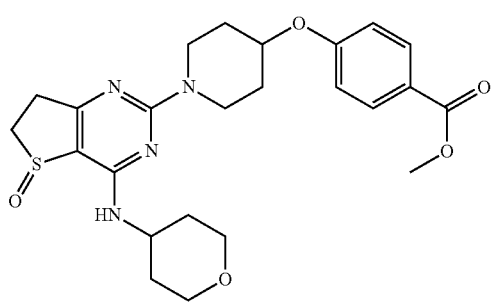

Starting from (IV-6) (cf. 6.2) and methyl 4-(piperidin-4-yloxy)-benzoate (*J. Med. Chem.* 2002, 3406), methyl 4-{1-[5-oxo-4-(tetrahydropyran-4-ylamino)-6,7-dihydro-5H-5λ⁴-thieno[3,2-d]pyrimidin-2-yl]-piperidin-4-yloxy}-benzoate can be prepared and purified analogously to Example 1.15 (cf. 15.). Analytical HPLC-MS (method A): RT=1.17 min.

24.2 4-{1-[5-oxo-4-(tetrahydropyran-4-ylamino)-6,7-dihydro-5H-5λ⁴-thieno[3,2-d]pyrimidin-2-yl]-piperidin-4-yloxy}-benzoic acid

Example 1.24

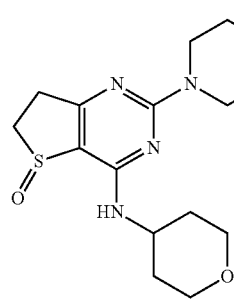
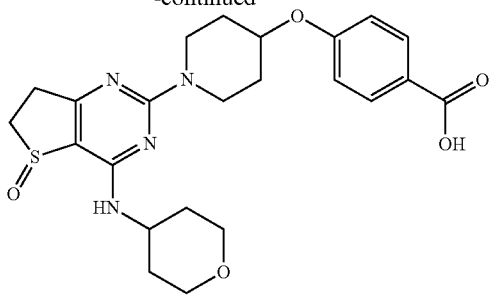

Example 1.24

80 mg of methyl 4-{1-[5-oxo-4-(tetrahydropyran-4-ylamino)-6,7-dihydro-5H-5λ⁴-thieno[3,2-d]pyrimidin-2-yl]-piperidin-4-yloxy}-benzoate are placed in 1.5 ml of methanol, then 560 µl of a 1N NaOH solution are added. The reaction mixture is stirred at 50° C. until there is no further reaction, then combined with a 1 M HCl solution. The product is extracted with dichloromethane. 77 mg Example 1.24 are obtained in the form of a solid. Analytical HPLC-MS (method B): RT=1.19 min.

25. SYNTHESIS OF 2-(1-{2-[4-(4-CHLOROPHENYL)-PIPERIDIN-1-YL]-5-OXO-6,7-DIHYDRO-5H-5λ⁴-THIENO[3,2-D]PYRIMIDIN-4-YLAMINO}-CYCLOPROPYL)-PROPAN-2-OL

Example 1.25

25.1 2-[1-(2-chloro-6,7-dihydrothieno[3,2-d]pyrimidin-4-ylamino)-cyclopropyl]-propan-2-ol (III-8)

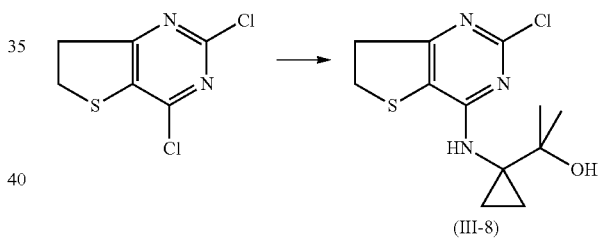

(III-8)

2.7 g (II) are placed in 30 ml dioxane, then 6.8 ml diisopropyl-ethylamine and 1.8 g 2-(1-aminocyclopropyl)-propan-2-ol (cf. *Liebigs Ann. Chem.* 1978.1194) are added. The reaction mixture is heated to 160° C. until there is no further reaction and after cooling it is evaporated to dryness. The residue is mixed with ice water. The product is extracted with dichloromethane and purified by chromatography. 125 mg (III-8) are obtained in the form of a solid. Analytical HPLC-MS (method A): RT=1.08 min.

25.2 2-[1-(2-chloro-5-oxo-6,7-dihydro-5H-5λ⁴-thieno[3,2-d]pyrimidin-4-ylamino)-cyclopropyl]-propan-2-ol (IV-8)

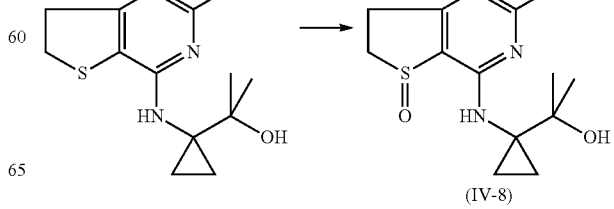

(IV-8)

21.6 mg S-(−)-1,1'-bi-2-naphthol are placed in 1 ml chloroform under argon, then 11 μl titanium(IV)-isopropoxide and 14 μl water are added. The reaction mixture is stirred for 1 hour at ambient temperature. Then a mixture of 120 mg (III-8) in 4 ml dichloromethane is added. The reaction mixture is cooled to −5° C. and after 30 minutes 69.5 μl tert-butylhydroperoxide 5-6 M in decane are added dropwise. The reaction mixture is stirred at −5° C. After 2 days the same amounts of S-(−)-1,1'-bi-2-naphthol, titanium(IV)-isopropoxide, water and tert-butylhydroperoxide are added again. The reaction mixture is stirred at −5° C. to 5° C. until there is no further reaction, mixed with water and made basic with NH₄OH. The organic phase is evaporated to dryness and the product is purified by chromatography (preparative HPLC, method B). 105 mg (IV-8) are obtained as. Analytical HPLC-MS (method A): RT=0.96 min.

25.3 2-(1-{2-[4-(4-chlorophenyl)-piperidin-1-yl]-5-oxo-6,7-dihydro-5H-5λ⁴-thieno[3,2-d]pyrimidin-4-ylamino}-cyclopropyl)-propan-2-ol Example 1.25

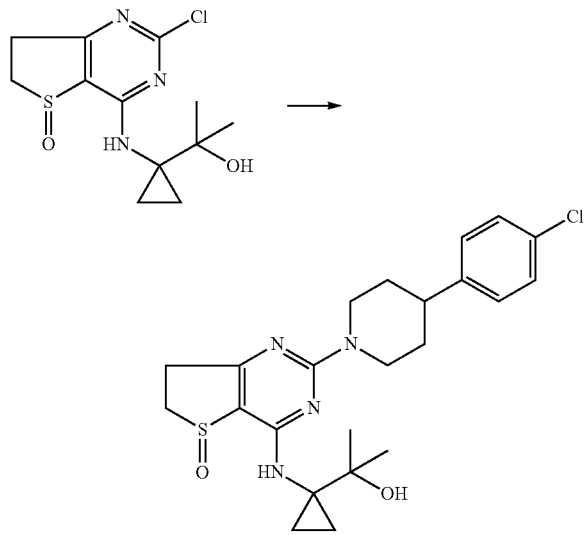

Example 1.25

Starting from (IV-8) and 4-(4-chlorophenyl)-piperidine hydrochloride Example 1.25 can be prepared and purified analogously to Example 1.14 (cf. 14.). Analytical HPLC-MS (method B): RT=1.37 min.

26. SYNTHESIS OF: {2-[4-(5-tert-BUTYL-1-METHYL-1H-INDOL-3-YL)-PIPERIDIN-1-YL]-5-OXO-6,7-DIHYDRO-5H-5λ⁴-THIENO[3,2-D]PYRIMIDIN-4-YL}-(TETRAHYDROPYRAN-4-YL)-AMINE Example 1.26

26.1 tert-butyl 4-(1H-indol-3-yl)-piperidine-1-carboxylate

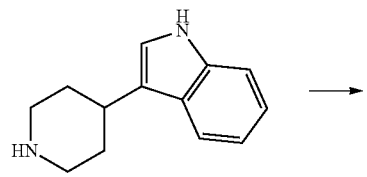

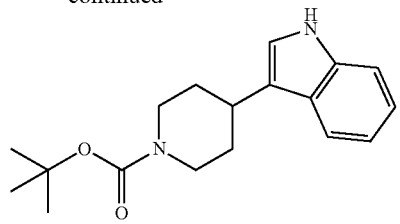

10 g 3-piperidin-4-yl-1H-indole are placed in 300 mL THF and 10.9 g di-tert-butyl-dicarbonate are added. The reaction mixture is stirred overnight at ambient temperature and evaporated to dryness. The residue is mixed with water and the product is extracted with diethyl ether and purified by chromatography. 9 g of the product are obtained in the form of a solid.

26.2 tert-butyl 4-(1-methyl-1H-indol-3-yl)-piperidine-1-carboxylate

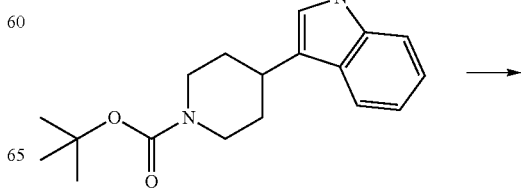

500 mg tert-butyl 4-(1H-indol-3-yl)-piperidine-1-carboxylate are placed in 8 ml dimethylformamide and 73.3 mg sodium hydride (60% in mineral oil) are added. After 15 min 175 μl methyl iodide are added. The reaction mixture is stirred at ambient temperature. After the reaction is complete the product is purified directly by preparative HPLC (method C). 302 mg of the product are obtained in the form of an oil. Analytical HPLC-MS (method A): RT=1.65 min.

26.3 5-tert-butyl-1-methyl-3-piperidin-4-yl-1H-indole (V-3)

-continued

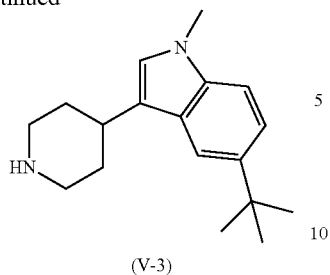

(V-3)

365 mg tert-butyl 4-(1-methyl-1H-indol-3-yl)-piperidine-1-carboxylate are placed in 1 ml dichloromethane and combined with 1.03 ml trifluoroacetic acid. The reaction mixture is stirred at ambient temperature. After 12 and 16 h another 1.03 ml trifluoroacetic acid are added. After a further 12 h the reaction mixture is evaporated to dryness. The residue is combined with toluene and evaporated to dryness. The residue is triturated with diethyl ether, the precipitate is suction filtered and dried. 154 mg (V-3) are obtained in the form of a solid. Analytical HPLC-MS (method A): RT=1.34 min.

26.4 {2-[4-(5-tert-butyl-1-methyl-1H-indol-3-yl)-piperidin-1-yl]-5-oxo-6,7-dihydro-5H-5λ⁴-thieno[3,2-d]pyrimidin-4-yl}-(tetrahydropyran-4-yl)-amine Example 1.26

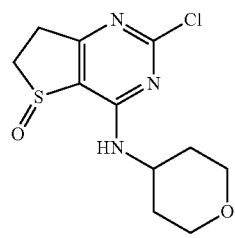

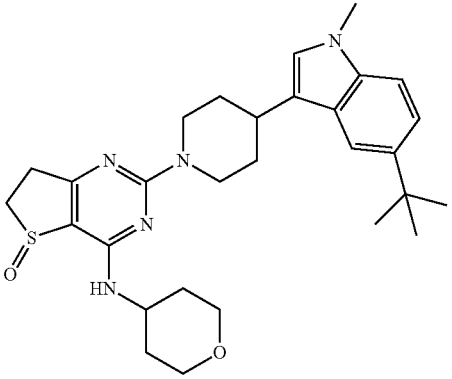

Example 1.26

Starting from (IV-6) (cf. 6.2) and (V-3), Example 1.26 can be prepared and purified analogously to Example 1.14 (cf. 14.). Analytical HPLC-MS (method B): RT=1.16 min.

27. SYNTHESIS OF: {2-[4-(5-FURAN-2-YL-1-METHYL-1H-PYRAZOL-3-YL)-PIPERIDIN-1-YL]-5-OXO-6,7-DIHYDRO-5H-5λ⁴-THIENO[3,2-D]PYRIMIDIN-4-YL}-(TETRAHYDROPYRAN-4-YL)-AMINE

Example 1.27

27.1 tert-butyl 14-(5-furan-2-yl-2H-pyrazol-3-yl)-piperidine-1-carboxylate

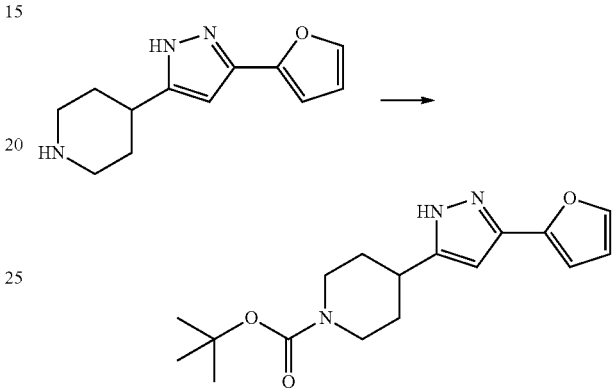

200 mg 4-(5-furan-2-yl-2H-pyrazol-3-yl)-piperidine are placed in 2 ml dioxane. Then 0.34 ml of water and 155 mg sodium carbonate are added. The reaction mixture is stirred at ambient temperature. After 5 min 204 mg di-tert-butyl-dicarbonate are added. After 3 h the reaction mixture is mixed with water and the product is extracted with dichloromethane. 300 mg product are obtained in the form of an oil. Analytical HPLC-MS (method B): RT=1.54 min.

27.2 tert-butyl 4-(5-furan-2-yl-2-methyl-2H-pyrazol-3-yl)-piperidine-1-carboxylate and tert-butyl 4-(5-furan-2-yl-1-methyl-1H-pyrazol-3-yl)-piperidine-1-carboxylate

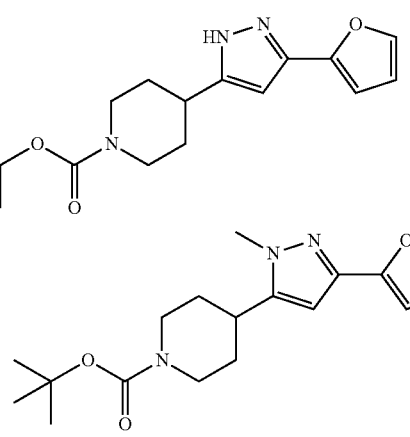

Isomer 1

+

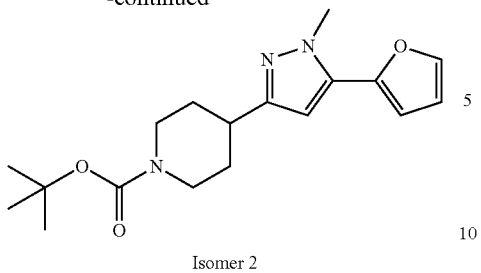

Isomer 2

250 mg tert-butyl 14-(5-furan-2-yl-2H-pyrazol-3-yl)-piperidine-1-carboxylate are placed in 1.5 ml dimethylformamide. The reaction mixture is cooled in the ice bath and 40 mg sodium hydride (60% in mineral oil) are added. After 10 min 60 μl methyl iodide are added. The reaction mixture is stirred for 30 min at 5° C. and then for 4 h at ambient temperature. The product is then purified directly by preparative HPLC (method D). 90 mg of isomer 1 and 50 mg of isomer 2 are obtained in the form of a solid. Analytical HPLC-MS (method D): RT=1.33 min (isomer 1); RT=1.28 (isomer 2).

27.3 4-(5-furan-2-yl-1-methyl-1H-pyrazol-3-yl)-piperidine (V-4)

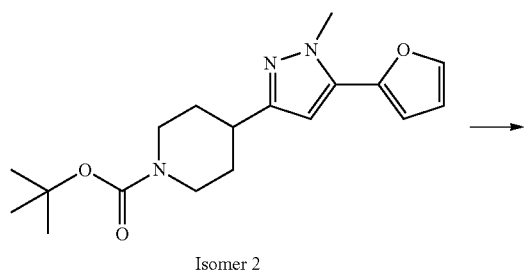

Isomer 2

(V-4)

47 mg isomer 2 are placed in 1 ml dichloromethane and 120 μl trifluoroacetic acid are added. The reaction mixture is stirred for 2 h at ambient temperature, then evaporated to dryness. The residue is combined with toluene and evaporated to dryness. The residue is mixed with water, made basic with conc. ammonia and the product is extracted with dichloromethane. 23 mg (V-4) are obtained in the form of a solid. Analytical HPLC-MS (method B): RT=0.85 min

27.4 {2-[4-(5-furan-2-yl-1-methyl-1H-pyrazol-3-yl)-piperidin-1-yl]-5-oxo-6,7-dihydro-5H-5λ⁴-thieno[3,2-d]pyrimidin-4-yl}-(tetrahydropyran-4-yl)-amine Example 1.27

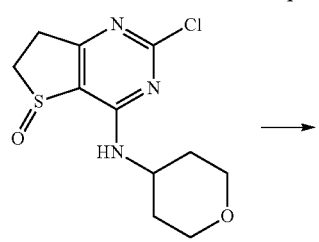

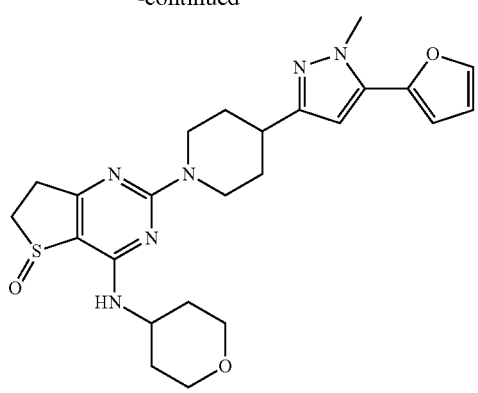

Example 1.27

Starting from (IV-6) (cf. 6.2) and (V-4) Example 1.27 can be prepared and purified analogously to Example 1.14 (cf. 14). Analytical HPLC-MS (method B): RT=1.21 min.

28. SYNTHESIS OF: (S)-5-(2-{4-[4-(4,5-DIHYDROOXAZOL-2-YL)-PHENOXY]-PIPERIDIN-1-YL}-5-OXO-6,7-DIHYDRO-5H-5λ⁴-THIENO[3,2-D]PYRIMIDIN-4-YLAMINO)-1-METHYLPIPERIDIN-2-ONE

Example 1.28

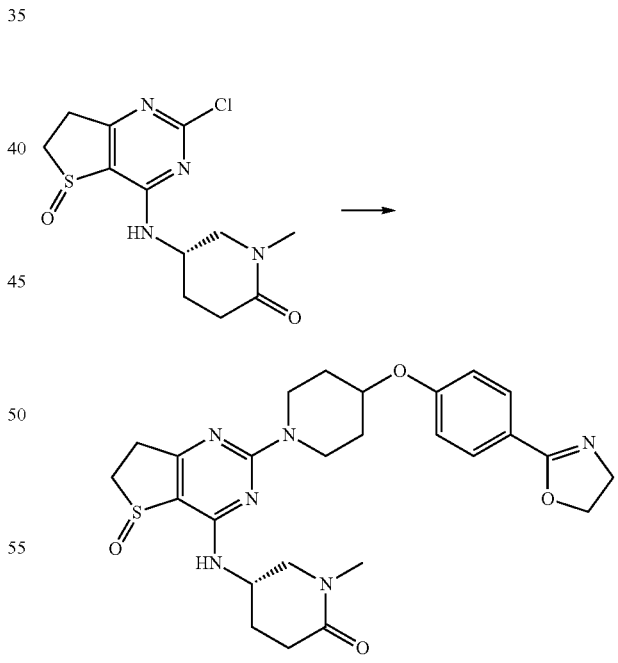

Example 1.28

Starting from (IV-5) (cf. 5.5) and (V-2) (cf. 23.3) Example 1.28 can be prepared and purified analogously to Example 1.16 (cf. 16.). Analytical HPLC-MS (method B): RT=1.07 min.

29. SYNTHESIS OF: {2-[4-(5-FURAN-2-YL-2-METHYL-2H-PYRAZOL-3-YL)-PIPERIDIN-1-YL]-5-OXO-6,7-DIHYDRO-5H-5λ⁴-THIENO[3,2-D]PYRIMIDIN-4-YL}-(TETRAHYDROPYRAN-4-YL)-AMINE

Example 1.29

29.1 4-(5-furan-2-yl-2-methyl-2H-pyrazol-3-yl)-piperidine (V-5)

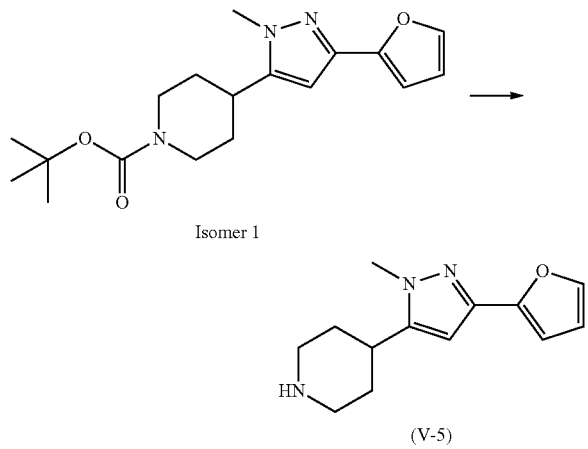

Starting from isomer 1 (cf. 27.2), (V-5) may be prepared analogously to (V-4) (cf. 27.3). Analytical HPLC-MS (method D): RT=0.89 min.

29.2 Synthesis of: {2-[4-(5-furan-2-yl-2-methyl-2H-pyrazol-3-yl)-piperidin-1-yl]-5-oxo-6,7-dihydro-5H-5λ⁴-thieno[3,2-d]pyrimidin-4-yl}-(tetrahydropyran-4-yl)-amine Example 1.29

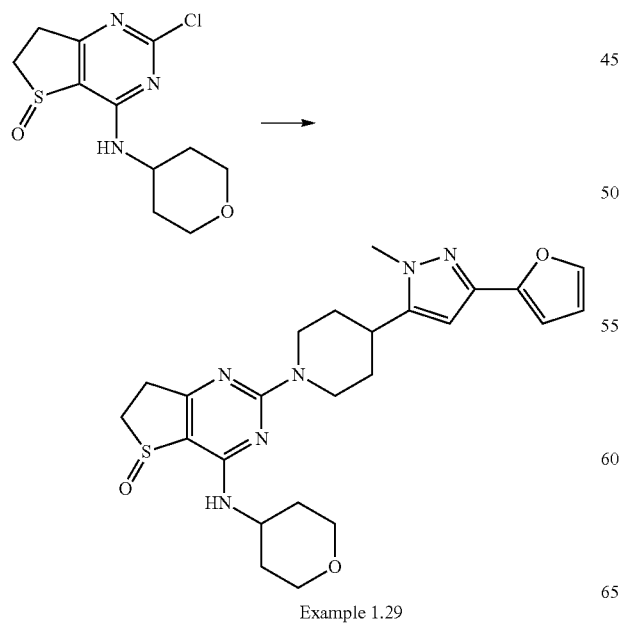

Example 1.29

Starting from (IV-6) (cf. 6.2) and (V-5) Example 1.29 can be prepared and purified analogously to Example 1.14 (cf. 14.). Analytical HPLC-MS (method B): RT=1.26 min.

30. SYNTHESIS OF: {2-[4-(1-METHYL-1H-IMIDAZO[4,5-c]PYRIDIN-2-YL)-PIPERIDIN-1-YL]-5-OXO-6,7-DIHYDRO-5H-5λ⁴-THIENO[3,2-D]PYRIMIDIN-4-YL}-(TETRAHYDROPYRAN-4-YL)-AMINE

Example 1.30

30.1 methyl-(3-nitropyridin-4-yl)-amine

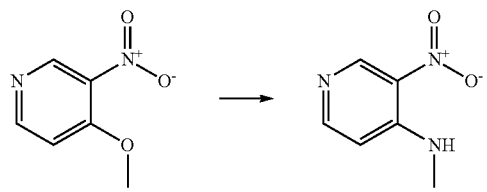

2.36 g 4-methoxy-3-nitro-pyridine and 2.33 ml methylamine (40% in water) are refluxed in 25 ml of ethanol for 3 h. Then the reaction mixture is evaporated to dryness. 2.3 g product are obtained in the form of a solid.

30.2 N⁴-methylpyridin-3,4-diamine

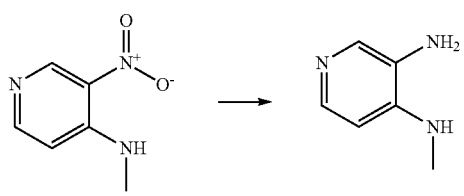

2.3 g methyl-(3-nitropyridin-4-yl)-amine are hydrogenated in 50 ml of methanol with 0.8 g Raney nickel for 2.5 h at 50° C. under 50 psi hydrogen pressure. The catalyst is filtered off and the filtrate is evaporated to dryness. The product is purified by chromatography (Alox, dichloromethane/methanol of 99/1 to 19/1). 1.55 g product are obtained in the form of a solid. m.p: 163-165° C.

30.3 1-methyl-2-piperidin-4-yl-1H-imidazo[4,5-c]pyridine (V-6):

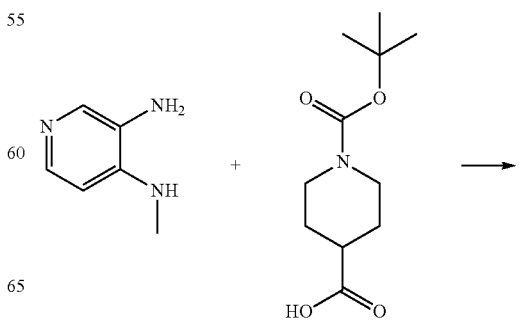

-continued

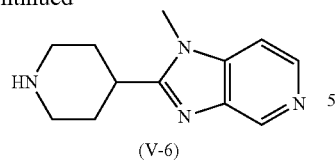
(V-6)

450 mg M-methylpyridin-3,4-diamine and 838 mg mono-tert-butyl piperidine-1,4-dicarboxylate are heated in 8.6 g polyphosphoric acid for 4 h at 200° C. After cooling the mixture is made basic with 4 N NaOH and acidified with trifluoroacetic acid. The mixture is purified by preparative HPLC (method C). 3.37 g (50%) (V-6) are obtained as the trifluoroacetate. Analytical HPLC-MS (method B): RT=0.30 min.

30.4 {2-[4-(1-methyl-1H-imidazo[4,5-c]pyridin-2-yl)-piperidin-1-yl]-5-oxo-6,7-dihydro-5H-5$\lambda^4$-thieno[3,2-d]pyrimidin-4-yl}-(tetrahydropyran-4-yl)-amine Example 1.30

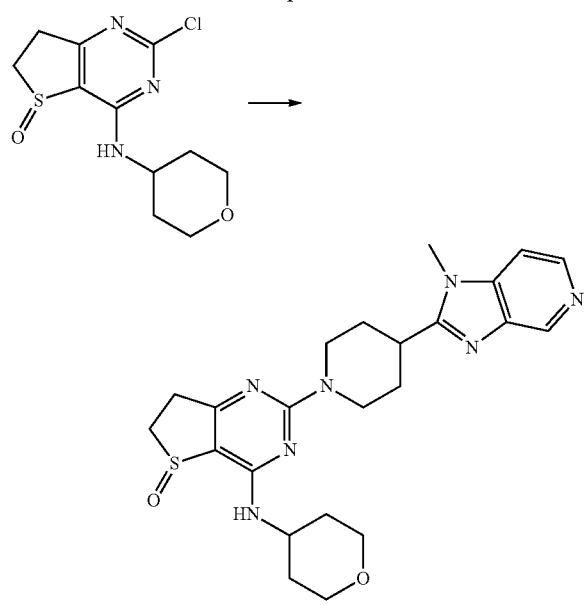

Example 1.30

Starting from (IV-6) (cf. 6.2) and (V-6) Example 1.30 can be prepared and purified analogously to Example 1.14 (cf. 14). Analytical HPLC-MS (method D): RT=0.86 min.

31. SYNTHESIS OF 2-METHOXY-N-1-[5-OXO-4-(TETRAHYDROPYRAN-4-YLAMINO)-6,7-DIHYDRO-5H-5$\lambda^4$-THIENO[3,2-D]PYRIMIDIN-2-YL]-4-PHENYLPIPERIDIN-4-YLMETHYL)-ACETAMIDE Example 1.31

31.1 tert-butyl 4-[(2-methoxyacetylamino)-methyl]-4-phenylpiperidine-1-carboxylate

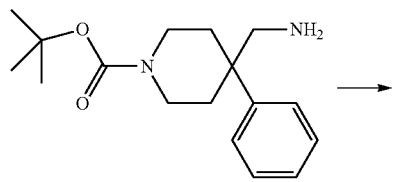

-continued

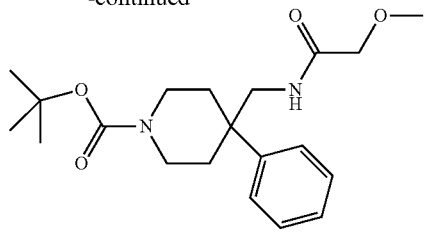

3.7 g of commercial tert-butyl 4-aminomethyl-4-phenyl-piperidine-1-carboxylate and 3 ml diisopropylethylamine are placed in 30 ml dichloromethane. Then 2.25 ml methoxyacetyl chloride are slowly added. The reaction mixture is stirred at ambient temperature until there is no further reaction, then mixed with water. The organic phase is evaporated to dryness. 4.7 g product are obtained in the form of an oil.

31.2 2-methoxy-N-(4-phenylpiperidin-4-ylmethyl)-acetamide (V-7)

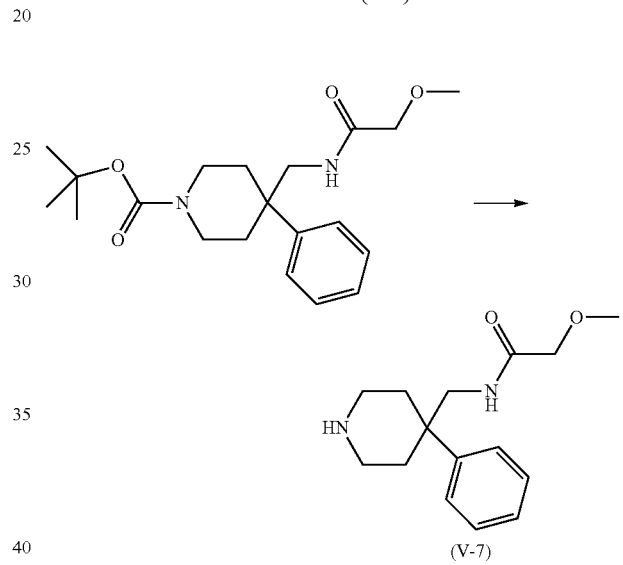
(V-7)

1 g tert-butyl 4-[(2-methoxyacetylamino)-methyl]-4-phenylpiperidine-1-carboxylate are placed in 4 ml dichloromethane. Then 1.7 ml trifluoroacetic acid are added and the mixture is stirred overnight at ambient temperature. The reaction mixture is made basic with potassium carbonate and the organic phase is evaporated to dryness. 610 mg (V-7) are obtained in the form of an oil.

31.3 Synthesis of 2-methoxy-N-{1-[5-oxo-4-(tetrahydropyran-4-ylamino)-6,7-dihydro-5H-5$\lambda^4$-thieno[3,2-d]pyrimidin-2-yl]-4-phenylpiperidin-4-ylmethyl}-acetamide Example 1.31

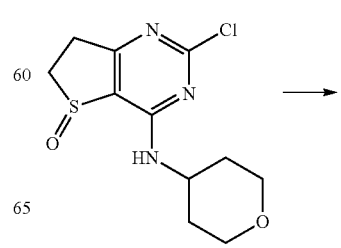

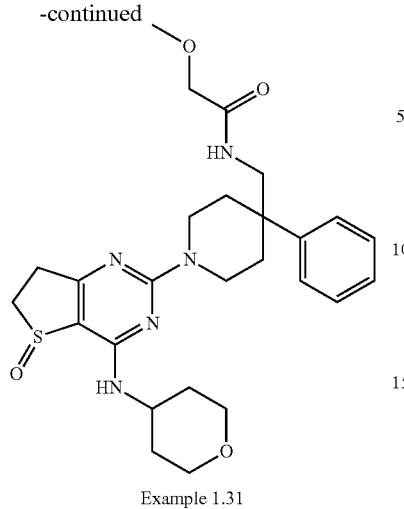

Example 1.31

Starting from (IV-6) (cf. 6.2) and (V-7) Example 1.31 can be prepared and purified analogously to Example 1.15 (cf. 15.). Analytical HPLC-MS (method B): RT=1.21 min.

32. SYNTHESIS OF: N-CYCLOPROPYL-N-METHYL-4-{1-[5-OXO-4-(TETRAHYDRO PYRAN-4-YLAMINO)-6,7-DIHYDRO-5H-5λ$^4$-THIENO[3,2-D]PYRIMIDIN-2-YL]-PIPERIDIN-4-YL}-BENZAMIDE

Example 1.32

32.1 tert-butyl 4-[4-(cyclopropylmethylcarbamoyl)-phenyl]-piperidine-1-carboxylate 500 mg tert-butyl 4-(4-carboxyphenyl)-piperidine-1-carboxylate are placed in 28 ml dimethylformamide, then 1.14 ml diisopropylethylamine and 747 mg HATU are added. The reaction mixture is stirred for 15 min at ambient temperature, then 194 mg cyclopropylmethylamine hydrochloride are added. The reaction mixture is stirred overnight at ambient temperature. Then the product is purified by preparative HPLC (method A). 480 mg product are obtained in the form of an oil. Analytical HPLC-MS (method B): RT=1.64 min.

32.2 N-cyclopropyl-N-methyl-4-piperidin-4-yl-benzamide (V-8)

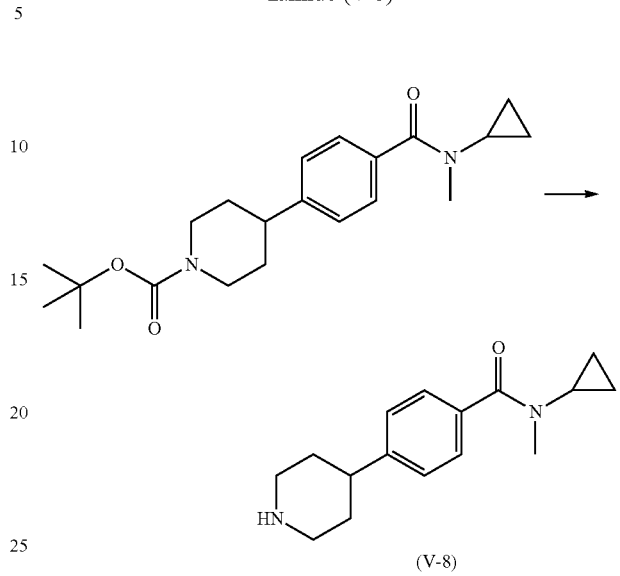

480 mg tert-butyl 4-[4-(cyclopropylmethylcarbamoyl)-phenyl]-piperidine-1-carboxylate are placed in 7.8 ml dichloromethane and combined with 1.09 ml trifluoroacetic acid. The reaction mixture is stirred for 1.5 h at ambient temperature and then evaporated to dryness. The residue is combined with toluene and evaporated to dryness once more. 444 mg (V-8) are obtained as the trifluoroacetate. Analytical HPLC-MS (method B): RT=1.11 min.

32.3 N-cyclopropyl-N-methyl-4-{1-[5-oxo-4-(tetrahydropyran-4-ylamino)-6,7-dihydro-5H-5λ$^4$-thieno[3,2-d]pyrimidin-2-yl]-piperidin-4-yl}-benzamide Example 1.32

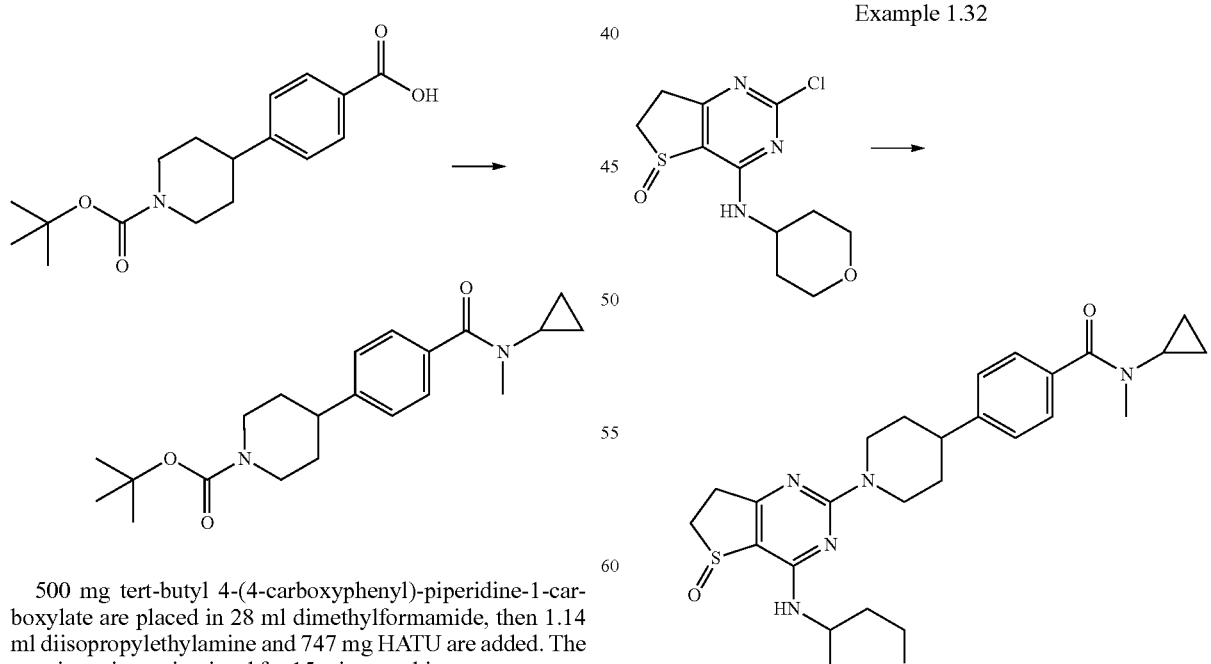

Example 1.32

Starting from (IV-6) (cf. 6.2) and (V-8) Example 1.32 can be prepared and purified analogously to Example 1.14 (cf. 14.). Analytical HPLC-MS (method D): RT=1.05 min.

33. SYNTHESIS OF: N-CYCLOPROPYL-N-METHYL-4-{1-[5-OXO-4-(TETRAHYDROPYRAN-4-YLAMINO)-6,7-DIHYDRO-5H-5$\lambda^4$-THIENO[3,2-D]PYRIMIDIN-2-YL]-PIPERIDIN-4-YLOXY}-BENZAMIDE Example 1.33

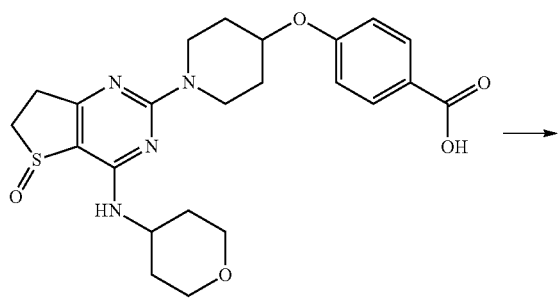

Example 1.24

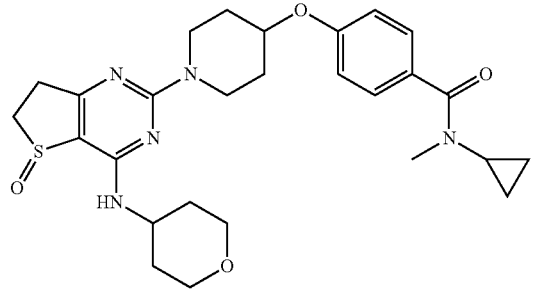

Example 1.33

55 mg of Example 1.24 (cf. 24.2) are placed in 2 ml dimethylformamide, then 81 µl diisopropylethylamine and 53.1 mg O-(7-azabenzotriazol-1-yl-)-N,N,N',N'-tetramethyluronium hexafluorophosphate (HATU) are added. After 15 min 13.8 mg cyclopropylmethylamin hydrochloride are added. The reaction mixture is stirred at ambient temperature until there is no further reaction and the product is purified directly by preparative HPLC (method B). 30 mg Example 1.33 are obtained in the form of a solid. Analytical HPLC-MS (method D): RT=1.03 min.

34. SYNTHESIS OF: {5-OXO-2-[4-(PYRIDIN-4-YLOXY)-PIPERIDIN-1-YL]-6,7-DIHYDRO-5H-5$\lambda^4$-THIENO[3,2-D]PYRIMIDIN-4-YL}-(TETRAHYDROPYRAN-4-YL)-AMINE Example 1.34

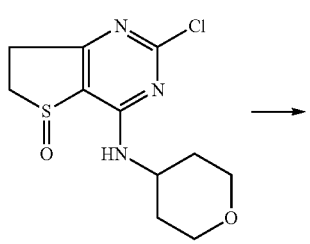

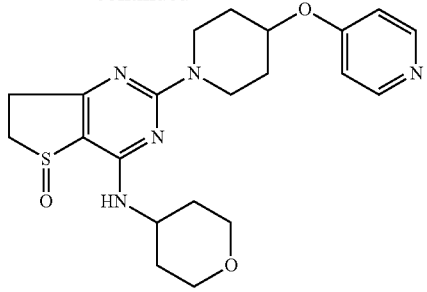

Example 1.34

Starting from (IV-6) (cf. 6.2) and 4-(piperidin-4-yloxy)-pyridine Example 1.34 can be prepared and purified analogously to Example 1.15 (cf. 15.). Analytical HPLC-MS (method B): RT=0.99 min.

35. SYNTHESIS OF: {2-[4-(4-CHLOROPHENOXY)-PIPERIDIN-1-YL]-5-OXO-6,7-DIHYDRO-5H-5$\lambda^4$-THIENO[3,2-D]PYRIMIDIN-4-YL}-(TETRAHYDROPYRAN-4-YL)-AMINE Example 1.35

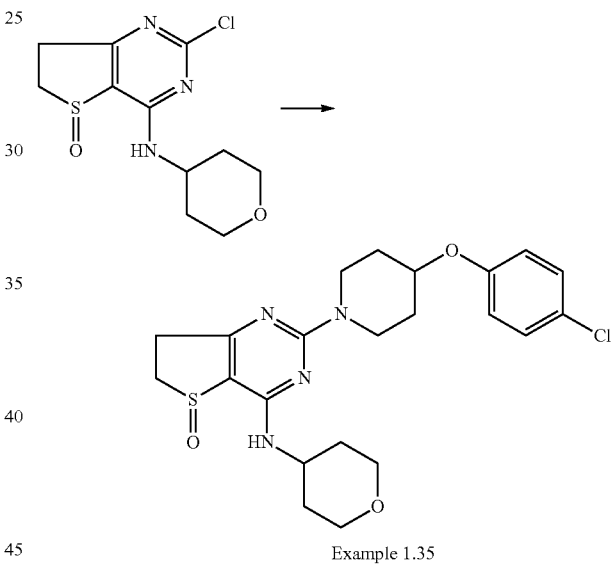

Example 1.35

Starting from (IV-6) (cf. 6.2) and 4-(4-chlorophenoxy)-piperidine Example 1.35 can be prepared and purified analogously to Example 1.15 (cf. 15.). Analytical HPLC-MS (method B): RT=1.39 min.

36. SYNTHESIS OF: (S)-1-METHYL-5-{2-[4-(5-METHYL-4-PHENYL-OXAZOL-2-YL)-PIPERIDIN-1-YL]-5-OXO-6,7-DIHYDRO-5H-5$\lambda^4$-THIENO[3,2-D]PYRIMIDIN-4-YLAMINO}-PIPERIDIN-2-ONE Example 1.36

36.1 4-(5-methyl-4-phenyloxazol-2-yl)-piperidine (V-9)

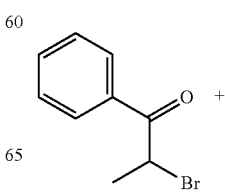

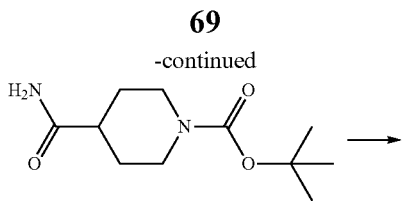

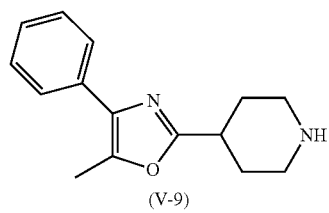

(V-9)

1.75 g 2-bromo-1-phenylpropan-1-one and 1.87 g tert-butyl 4-carbamoylpiperidine-1-carboxylate are placed in 0.5 ml NMP. The reaction mixture is heated to 160° C. for 20 min in the microwave and for 35 min in the oil bath, then after cooling it is taken up in methanol and evaporated to dryness. The residue is mixed with water, treated in the ultrasound bath and the insoluble oil is suction filtered. The mother liquor is purified by preparative HPLC (method C). 160 mg (V-9) are obtained as the trifluoroacetate. Analytical HPLC-MS (method B): RT=1.24 min.

36.2 (S)-1-methyl-5-{2-[4-(5-methyl-4-phenyloxazol-2-yl)-piperidin-1-yl]-5-oxo-6,7-dihydro-5H-5λ$^4$-thieno[3,2-d]pyrimidin-4-ylamino}-piperidin-2-one Example 1.36

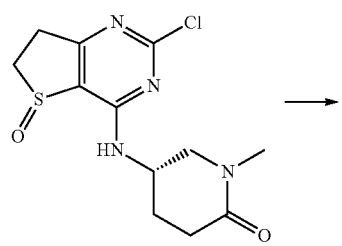

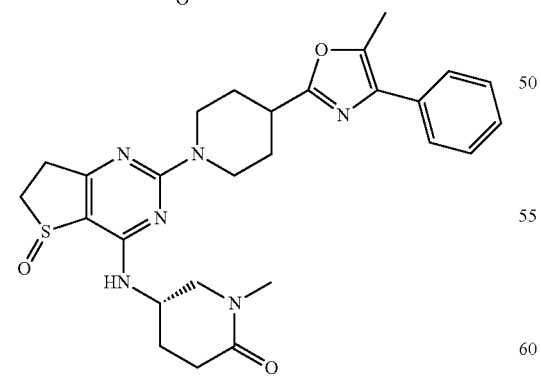

Example 1.36

Starting from (IV-5) (cf. 5.5) and (V-9) Example 1.36 can be prepared and purified analogously to Example 1.14 (cf. 14.). Analytical HPLC-MS (method D): RT=1.08 min.

37 SYNTHESIS OF: (1-{2-[4-(5-METHYL-4-PHENYLOXAZOL-2-YL)-PIPERIDIN-1-YL]-5-OXO-6,7-DIHYDRO-5H-5λ$^4$-THIENO[3,2-D]PYRIMIDIN-4-YLAMINO}-CYCLOPROPYL)-METHANOL

Example 1.37

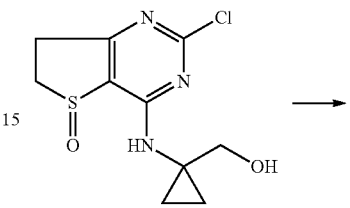

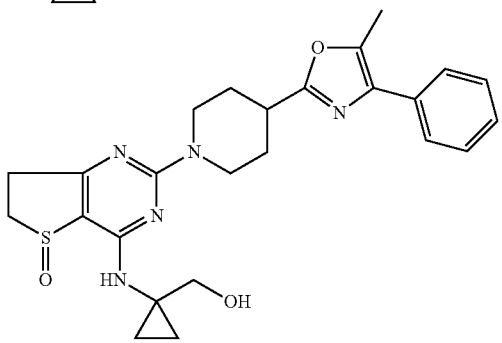

Example 1.37

Starting from (IV-2) (cf. 2.4) and (V-9) (cf. 36.1) Example 1.37 can be prepared and purified analogously to Example 1.14 (cf. 14.). Analytical HPLC-MS (method B): RT=1.33 min.

38. SYNTHESIS OF: (S)-5-{2-[4-(4,5-DIPHENYLOXAZOL-2-YL)-PIPERIDIN-1-YL]-5-OXO-6,7-DIHYDRO-5H-5λ$^4$-THIENO[3,2-D]PYRIMIDIN-4-YLAMINO}-1-METHYLPIPERIDIN-2-ONE

Example 1.38

38.1 tert-butyl 4-(4,5-diphenyloxazol-2-yl)-piperidine-1-carboxylate

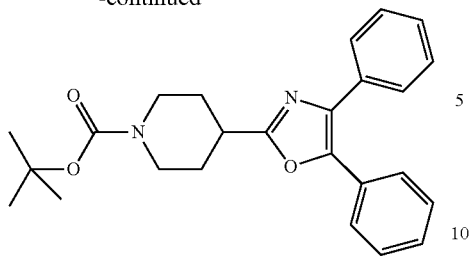

Starting from 1.08 g of mono-tert-butyl piperidine-1,4-dicarboxylate and 1 g 2-amino-1,2-diphenyl-ethanol the product may be prepared as described in the literature (cf. Tet. 2001, 4867). The product is purified by chromatography (method B). 560 mg are obtained in the form of an oil. Analytical HPLC-MS (method A): RT=1.72 min.

38.2 4-(4,5-diphenyloxazol-2-yl)-piperidine (V-10)

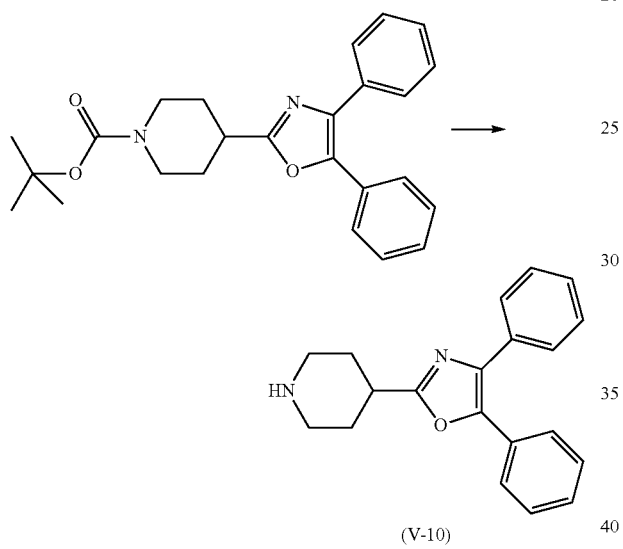

560 mg tert-butyl 4-(4,5-diphenyloxazol-2-yl)-piperidine-1-carboxylate are placed in 2 ml dichloromethane, then 1.1 ml trifluoroacetic acid are added. The reaction mixture is stirred for 15 hours at ambient temperature, then evaporated to dryness. The residue is combined with toluene and evaporated to dryness again. The residue is mixed with diethyl ether and the precipitated solid is suction filtered and dried. 510 mg (V-10) are obtained. Analytical HPLC-MS (method B): RT=1.38 min.

38.3 (S)-5-{2-[4-(4,5-diphenyloxazol-2-yl)-piperidin-1-yl]-5-oxo-6,7-dihydro-5H-5λ$^4$-thieno[3,2-d]pyrimidin-4-ylamino}-1-methylpiperidin-2-one Example 1.38

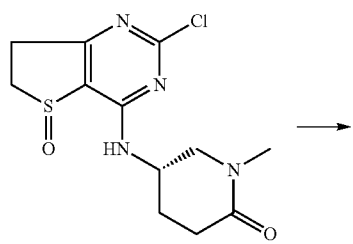

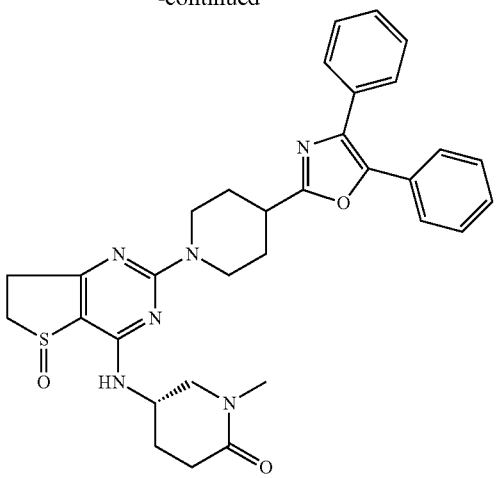

Example 1.38

Starting from (IV-5) (cf. 5.5) and (V-10) Example 1.38 can be prepared and purified analogously to Example 1.14 (cf. 14.). Analytical HPLC-MS (method B): RT=1.40 min.

39. SYNTHESIS OF: (4-(4-CHLOROPHENYL)-1-[5-OXO-4-(TETRAHYDROPYRAN-4-YLAMINO)-6,7-DIHYDRO-5H-5λ$^4$-THIENO[3,2-D]PYRIMIDIN-2-YL]-PIPERIDIN-4-YL)-METHANOL

Example 1.39

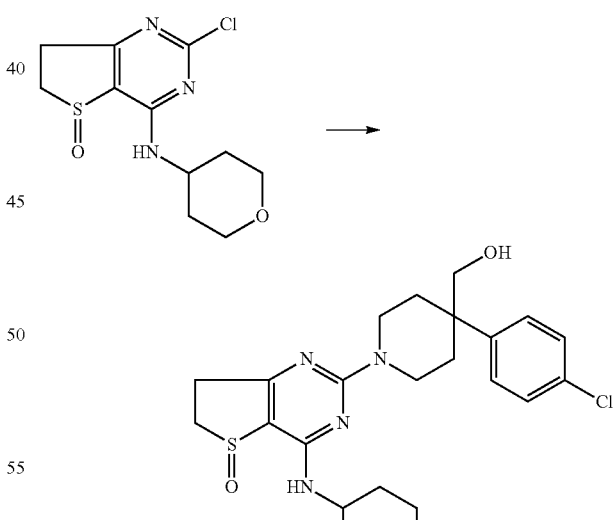

Example 1.39

Starting from (IV-6) (cf. 6.2) and [4-(4-chlorophenyl)-piperidin-4-yl]-methanol (J. Med. Chem. 2004, 497) Example 1.39 can be prepared and purified analogously to Example 1.15 (cf. 15.). Analytical HPLC-MS (method B): RT=1.24 min.

40. SYNTHESIS OF: [1-(2-{4-[5-(4-CHLOROPHE-NYL)-4-METHYLOXAZOL-2-YL]-PIPERIDIN-1-YL}-5-OXO-6,7-DIHYDRO-5H-5λ⁴-THIENO[3,2-D]PYRIMIDIN-4-YLAMINO)-CYCLOPROPYL]-METHANOL

Example 1.40

40.1 4-[5-(4-chlorophenyl)-4-methyloxazol-2-yl]-piperidine (V-11)

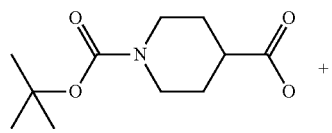

+

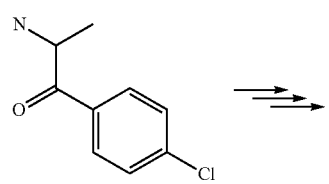

⇒

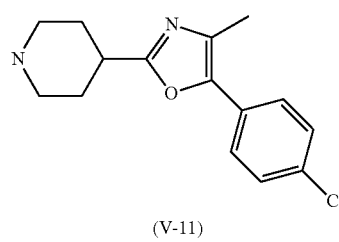

(V-11)

Starting from mono-tert-butyl piperidine-1,4-dicarboxylate and 2-amino-1-(4-chlorophenyl)-propan-1-one (cf. *J. Med. Chem.* 1974, 416), (V-11) may be prepared analogously to (V-10) (cf. 38.2). Analytical HPLC-MS (method B): RT=1.30 min.

40.2 [1-(2-{4-[5-(4-chlorophenyl)-4-methyloxazol-2-yl]-piperidin-1-yl}-5-oxo-6,7-dihydro-5H-5λ⁴-thieno[3,2-d]pyrimidin-4-ylamino)-cyclopropyl]-methanol Example 1.40

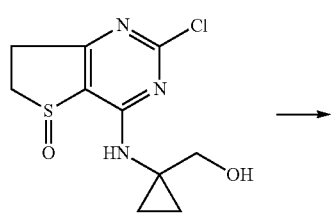

→

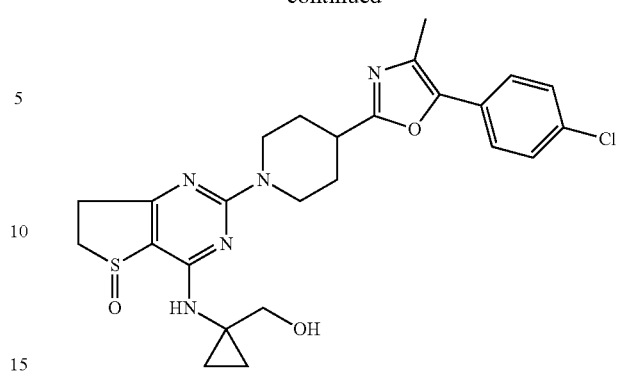

Example 1.40

Starting from (IV-2) (cf. 2.4) and (V-11), Example 1.40 can be prepared and purified analogously to Example 1.14 (cf. 14.). Analytical HPLC-MS (method B): RT=1.37 min.

41. SYNTHESIS OF: 4-(4-CHLOROPHENYL)-1-[5-OXO-4-(TETRAHYDROPYRAN-4-YLAMINO)-6,7-DIHYDRO-5H-5λ⁴-THIENO[3,2-D]PYRIMIDIN-2-YL]-PIPERIDIN-4-OL

Example 1.41

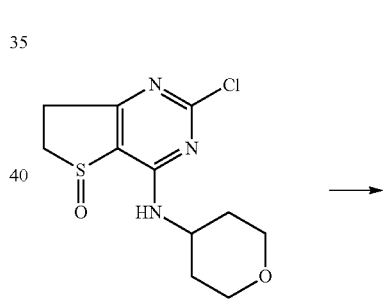

→

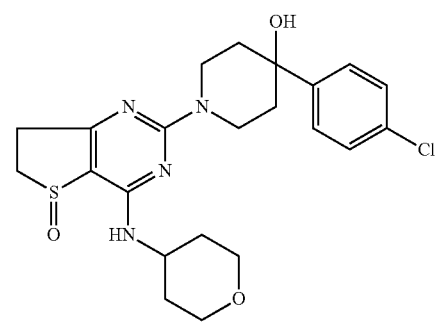

Example 1.41

Starting from (IV-6) (cf. 6.2) and 4-(4-chlorophenyl)-piperidin-4-ol, Example 1.41 can be prepared and purified analogously to Example 1.15 (cf. 15.). Analytical HPLC-MS (method B): RT=1.25 min.

42. SYNTHESIS OF: {2-[4-(4-CHLOROPHENYL)-4-METHOXYPIPERIDIN-1-YL]-5-OXO-6,7-DIHYDRO-5H-5λ⁴-THIENO[3,2-D]PYRIMIDIN-4-YL}-(TETRAHYDROPYRAN-4-YL)-AMINE

Example 1.42

42.1 tert-butyl 4-(4-chlorophenyl)-4-hydroxypiperidine-1-carboxylate 500 mg 4-(4-chlorophenyl)-piperidin-4-ol are placed in 6 ml dioxane, then 0.9 ml of water and 400 mg sodium carbonate are added. After 5 min, 530 mg di-tert-butyl-dicarbonate are added. The reaction mixture is stirred for 12 hours at ambient temperature, then mixed with water and the product is extracted with dichloromethane. 790 mg of product are obtained in the form of an oil. Analytical HPLC-MS (method B): RT=1.65 min.

42.2 tert-butyl 4-(4-chlorophenyl)-4-methoxypiperidine-1-carboxylate

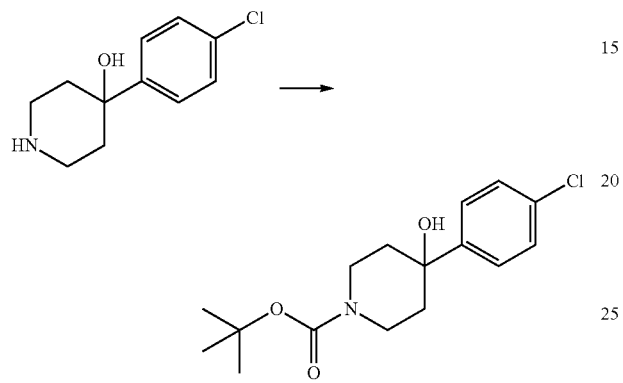

790 mg tert-butyl 4-(4-chlorophenyl)-4-hydroxypiperidine-1-carboxylate are placed in 5 ml dimethylformamide and 193 mg sodium hydride (60% in mineral oil) are added. The reaction mixture is stirred for 30 min at ambient temperature, then 267 µl methyl iodide are added. After 1 h the reaction mixture is poured onto ice and the product is extracted with diethyl ether. 650 mg product are obtained in the form of an oil. Analytical HPLC-MS (method B): RT=1.88 min.

42.3 4-(4-chlorophenyl)-4-methoxypiperidine (V-12)

650 mg tert-butyl 4-(4-chlorophenyl)-4-methoxypiperidine-1-carboxylate are placed in 3 ml dichloromethane, then 1.46 ml trifluoroacetic acid are added. The reaction mixture is stirred overnight at ambient temperature and evaporated to dryness. The residue is combined with toluene and evaporated to dryness again. The residue is triturated with diethyl ether and the solid is suction filtered. 450 mg (V-12) are obtained as the trifluoroacetate. Analytical HPLC-MS (method B): RT=1.22 min. 42.4 {2-[4-(4-chlorophenyl)-4-methoxypiperidin-1-yl]-5-oxo-6,7-dihydro-5H-5λ⁴-thieno[3,2-d]pyrimidin-4-yl}-(tetrahydropyran-4-yl)-amine Example 1.42

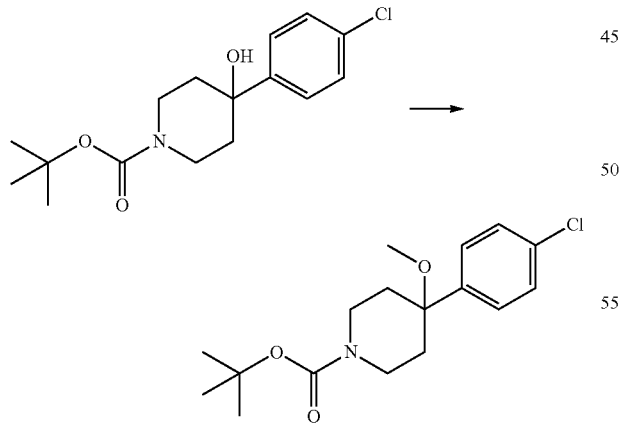

Example 1.42

Starting from (IV-6) (cf. 6.2) and (V-12), Example 1.42 can be prepared and purified analogously to Example 1.15 (cf. 15.). Analytical HPLC-MS (method B): RT=1.39 min.

43. SYNTHESIS OF: 4-{1-[4-(1-HYDROXYM-ETHYLCYCLOPROPYLAMINO)-5-OXO-6,7-DIHYDRO-5H-5λ⁴-THIENO[3,2-D]PYRIMIDIN-2-YL]-PIPERIDIN-4-YLOXY}-BENZONITRILE

Example 1.43

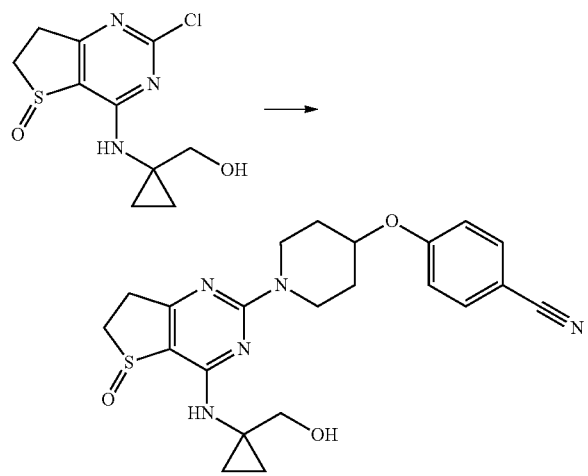

Example 1.43

Starting from (IV-2) (cf. 2.4) and 4-(piperidin-4-yloxy)-benzonitrile (WO2007/106705) Example 1.43 can be prepared and purified analogously to Example 1.14 (cf. 14.). Analytical HPLC-MS (method B): RT=1.24 min.

44. SYNTHESIS OF: 5-OXO-2-[4-(4,5,6,7-TETRAHYDROBENZOXAZOL-2-YL)-PIPERIDIN-1-YL]-6,7-DIHYDRO-5H-5λ⁴-THIENO[3,2-D]PYRIMIDIN-4-YL)-(TETRAHYDROPYRAN-4-YL)-AMINE

Example 1.44

44.1 2-(1-benzylpiperidin-4-yl)-4,5,6,7-tetrahydrobenzoxazole

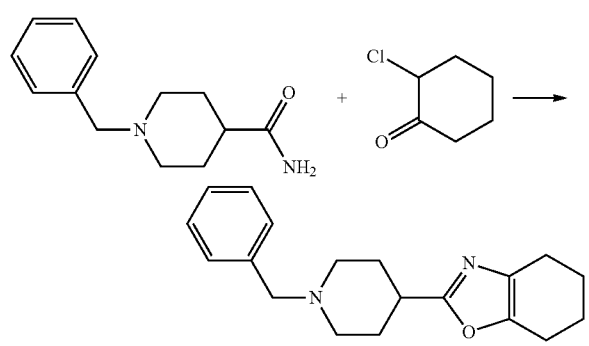

A mixture of 2.43 g 2-chlorocyclohexanone and 1 g 1-benzylpiperidine-4-carboxylic acid amide (WO2005/61483) is heated to 160° C. in the microwave until there is no further reaction. The product is purified by chromatography. 963 mg of the product are obtained. Analytical HPLC-MS (method B): RT=1.28 min.

44.2 2-piperidin-4-yl-4,5,6,7-tetrahydrobenzoxazole (V-13)

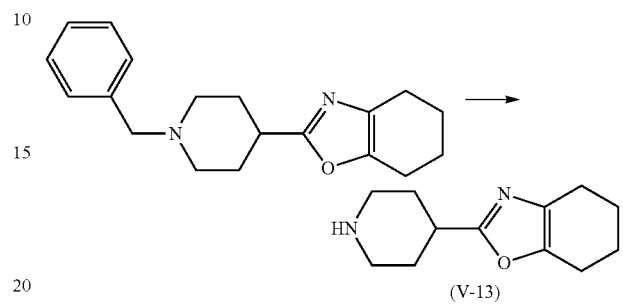

903 mg of 2-(1-benzyl-piperidin-4-yl)-4,5,6,7-tetrahydrobenzoxazole are placed in 20 ml of methanol and hydrogenated with 450 mg Pd/C 10% at a pressure of 3 bar and at ambient temperature. After 12 hours the catalyst is suction filtered and the filtrate is evaporated to dryness. The product is purified by chromatography. 469 mg (V-13) are obtained as the trifluoroacetate. Analytical HPLC-MS (method B): RT=1.09 min.

44.3 5-oxo-2-[4-(4,5,6,7-tetrahydrobenzoxazol-2-yl)-piperidin-1-yl]-6,7-dihydro-5H-5λ⁴-thieno[3,2-d]pyrimidin-4-yl)-(tetrahydropyran-4-yl)-amine Example 1.44

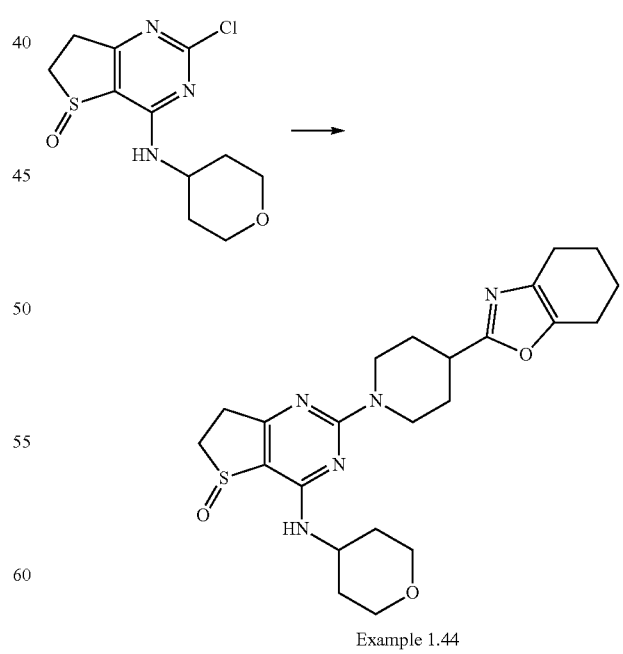

Example 1.44

Starting from (IV-6) (cf. 6.2) and (V-13), Example 1.44 can be prepared and purified analogously to Example 1.14 (cf. 14.). Analytical HPLC-MS (method B): RT=1.23 min.

Synthesis Scheme 2

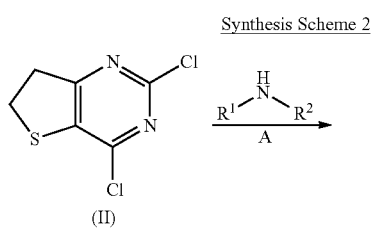

(II)

For the preparation of (II) see WO06111549

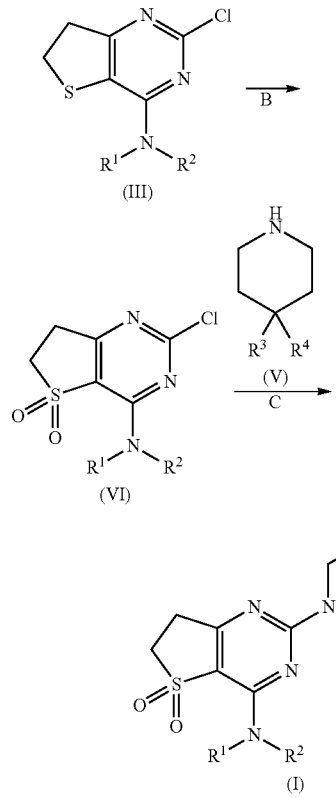

45. SYNTHESIS OF: (S)-5-{2-[4-(4-CHLOROPHE-NYL)-PIPERIDIN-1-YL]-5,5-DIOXO-6,7-DIHY-DRO-5H-5λ$^6$-THIENO[3,2-D]PYRIMIDIN-4-YLAMINO}-1-METHYLPIPERIDIN-2-ONE

Example 1.45

45.1 5-(2-chloro-5,5-dioxo-6,7-dihydro-5H-5λ$^6$-thieno[3,2-d]pyrimidin-4-ylamino)-1-methylpiperidin-2-one (VI-1)

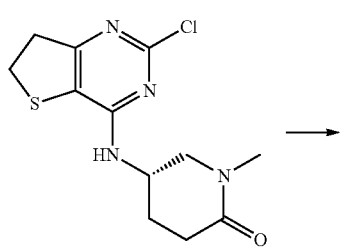

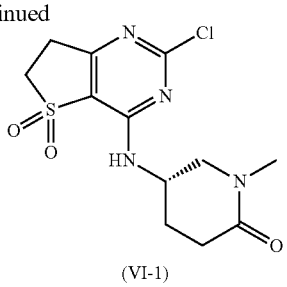

(VI-1)

200 mg (III-5) (cf. 5.4) are placed in 3 ml trifluoroacetic acid, then 165 μl hydrogen peroxide (35%) are slowly added dropwise. An exothermic reaction takes place. The reaction mixture is stirred for 12 hours at ambient temperature, then mixed with ice water and made basic with NH$_4$OH. The product is extracted with dichloromethane. 150 mg (VI-1) are obtained in the form of a solid.

45.2 (S)-5-{2-[4-(4-chlorophenyl)-piperidin-1-yl]-5,5-dioxo-6,7-dihydro-5H-5λ$^6$-thieno[3,2-d]pyrimidin-4-ylamino}-1-methylpiperidin-2-one Example 1.45

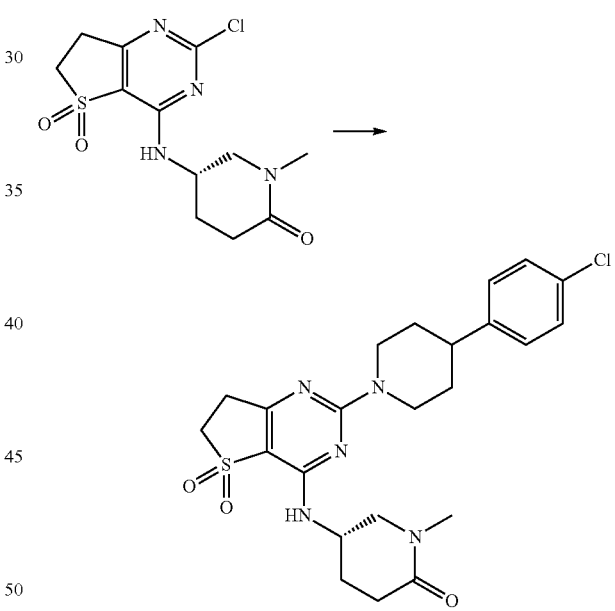

Starting from (VI-1) and 4-(4-chlorophenyl)-piperidine hydrochloride, Example 1.45 can be prepared and purified analogously to Example 1.14 (cf. 14.). Analytical HPLC-MS (method B): RT=1.48 min.

Methods of Chromatography

The Example compounds prepared according to the synthesis schemes shown above were characterised by the following chromatographic methods, which—if used—are individually specified in Tables B, D and E.

Analytical HPLC-MS, Method A

Waters ZMD mass spectrometer (positive ionisation (ESI$_+$)), Alliance 2690/2695 HPLC (diode array detector, wavelength range: 210 to 500 nm), Waters 2700 Autosampler, Waters 996/2996.

A: water with 0.10% TFA
B: acetonitrile with 0.10% TFA

| time in min | % A | % B | flow rate in ml/min |
|---|---|---|---|
| 0.00 | 95 | 5 | 2.50 |
| 0.20 | 95 | 5 | 2.50 |
| 1.50 | 2 | 98 | 2.50 |
| 1.70 | 2 | 98 | 2.50 |
| 1.90 | 95 | 5 | 2.50 |
| 2.20 | 95 | 5 | 2.50 |

The stationary phase used is a Merck Chromolith™ Flash RP-18e column, 4.6 mm×25 mm (column temperature: constant at 25° C.).
Analytical HPLC-MS, Method B
Waters ZMD mass spectrometer (positive ionisation (ESI$_+$)), Alliance 2690/2695 HPLC (diode array detector, wavelength range: 210 to 500 nm), Waters 2700 Autosampler, Waters 996/2996.
A: water with 0.10% TFA
B: acetonitrile with 0.10% TFA

| time in min | % A | % B | flow rate in ml/min |
|---|---|---|---|
| 0.00 | 95 | 5 | 2.80 |
| 0.30 | 95 | 5 | 2.80 |
| 1.60 | 2 | 98 | 2.80 |
| 1.90 | 2 | 98 | 2.80 |
| 2.00 | 95 | 5 | 2.50 |

The stationary phase used is a Merck Chromolith™ Flash RP-18e column, 3 mm×100 mm (column temperature: constant at 25° C.).
Analytical HPLC-MS, Method C
Waters ZQ2000 mass spectrometer (positive ionisation (ESI$_+$)), HP1100 HPLC (DAD, wavelength range: 210 to 500 nm), and Gilson 215 Autosampler.
A: water with 0.10% TFA
B: acetonitrile with 0.10% TFA

| time in min | % A | % B | flow rate in ml/min |
|---|---|---|---|
| 0.00 | 95 | 5 | 1.50 |
| 2.00 | 0 | 100 | 1.50 |
| 2.50 | 0 | 100 | 1.50 |
| 2.60 | 95 | 5 | 1.50 |

The stationary phase used is a Sunfire C18 column, 4.6×50 mm, 3.5 μm, column temperature 40° C.
Analytical HPLC-MS, Method D
Waters ZMD mass spectrometer (positive ionisation (ESI$_+$)), Alliance 2690/2695 HPLC (diode array detector, wavelength range: 210 to 500 nm), Waters 2700 Autosampler, Waters 996/2996.
A: water with 0.10% NH$_3$
B: acetonitrile with 0.10% NH$_3$

| time in min | % A | % B | flow rate in ml/min |
|---|---|---|---|
| 0.00 | 95 | 5 | 3.00 |
| 0.20 | 95 | 5 | 3.00 |
| 1.50 | 2 | 98 | 3.00 |
| 1.90 | 2 | 98 | 3.00 |
| 2.00 | 2 | 98 | 3.00 |

The stationary phase used is Waters, X-Bridge, C18, 3.5 nm, 4.6×20 mm, ambient temperature.
Analytical HPLC-MS, Method E
Waters ZMD mass spectrometer (positive ionisation (ESI$_+$)), Alliance 2690/2695 HPLC (diode array detector, wavelength range: 210 to 500 nm), Waters 2700 Autosampler, Waters 996/2996.
A: water with 0.10% TFA
B: acetonitrile with 0.10% TFA

| time in min | %A | % B | flow rate in ml/min |
|---|---|---|---|
| 0.00 | 95 | 5 | 1.20 |
| 0.30 | 95 | 5 | 1.20 |
| 9.00 | 2 | 98 | 1.20 |
| 9.40 | 2 | 98 | 1.20 |
| 9.50 | 95 | 5 | 2.80 |
| 9.90 | 95 | 5 | 2.80 |
| 10.00 | 95 | 5 | 0.20 |

The stationary phase used is a Merck Chromolith™ Flash RP-18e column, 4.6 mm×25 mm (column temperature: constant at 25° C.).
Analytical HPLC, Method A
Agilent 1100 (diode array detection, wavelength range: 210-380 nm).
A: water with 0.10% TFA
B: acetonitrile with 0.13% TFA

| time in min | % A | % B | flow rate in ml/min |
|---|---|---|---|
| 0.00 | 95 | 5 | 1.50 |
| 0.60 | 95 | 5 | 1.50 |
| 3.40 | 2 | 98 | 1.50 |
| 3.90 | 2 | 98 | 1.50 |
| 4.20 | 95 | 5 | 1.50 |
| 4.90 | 95 | 5 | 1.50 |

The stationary phase used is a Varian Microsorb column, RP C18, 3 μm, 100 A, ambient temperature.
Preparative HPLC-MS, Method A
Waters ZQ2000 mass spectrometer (positive ionisation (ESI$_+$)), HP1100 HPLC (DAD, wavelength range: 210-500 nm), and Gilson 215 Autosampler.
A: water with 0.10% TFA
B: acetonitrile

| time in min | % A | % B | flow rate in ml/min |
|---|---|---|---|
| 0.00 | 90 | 10 | 50 |
| 1.50 | 90 | 10 | 50 |
| 8.00 | 40 | 60 | 50 |
| 10.00 | 40 | 60 | 50 |
| 11.00 | 90 | 10 | 50 |

The stationary phase used is a Sunfire C18 column, 30×100 mm, 5 μm, ambient temperature.
Preparative HPLC, method A
Gilson HPLC with Gilson UV-VIS-155 detector, 231 XL sampling injector. The wavelength given is the substance-specific UV maximum.
A: water with 0.13% TFA
B: acetonitrile with 0.1% TFA

| time in min | % A | % B | flow rate in ml/min |
|---|---|---|---|
| 0.00 | 95 | 5 | 165 |
| 1.30 | 95 | 5 | 165 |
| 8.90 | 2 | 98 | 165 |
| 10.00 | 2 | 98 | 165 |
| 10.50 | 95 | 5 | 165 |
| 11.60 | 95 | 5 | 165 |

The stationary phase used is a Microsorb RP 18 column, 8 µm, 50×65 mm, ambient temperature.

Preparative HPLC, Method B

Gilson HPLC with Gilson UV-VIS-155 detector, 231 XL sampling injector. The wavelength given is the substance-specific UV maximum.

A: water with 0.1% ammonia 35%
B: acetonitrile

| time in min | % A | % B | flow rate in ml/min |
|---|---|---|---|
| 0.00 | 95 | 5 | 180 |
| 1.40 | 95 | 5 | 180 |
| 17.00 | 2 | 98 | 180 |
| 18.50 | 2 | 98 | 180 |
| 18.70 | 95 | 5 | 180 |
| 20.50 | 95 | 5 | 180 |

The stationary phase used is a Pursuit XRS RP 18 column, 10 µm, 50×150 mm, ambient temperature.

Preparative HPLC, Method C

Gilson HPLC with Gilson UV-VIS-155 detector, 231 XL sampling injector.

The wavelength given is the substance-specific UV maximum.

A: water with 0.13% TFA
B: acetonitrile with 0.1% TFA

| time in min | % A | % B | flow rate in ml/min |
|---|---|---|---|
| 0.00 | 95 | 5 | 180 |
| 1.40 | 95 | 5 | 180 |
| 17.00 | 2 | 98 | 180 |
| 18.50 | 2 | 98 | 180 |
| 18.70 | 95 | 5 | 180 |
| 20.50 | 95 | 5 | 180 |

The stationary phase used is a Microsorb RP 18 column, 8 µm, 50×150 mm, ambient temperature.

Preparative HPLC, Method D

Gilson HPLC with Gilson UV-VIS-155 detector, 231 XL sampling injector.

The wavelength given is the substance-specific UV maximum.

A: water with 0.1% ammonia 35%
B: acetonitrile

| time in min | % A | % B | flow rate in ml/min |
|---|---|---|---|
| 0.00 | 95 | 5 | 180 |
| 1.10 | 95 | 5 | 180 |
| 9.00 | 2 | 98 | 180 |
| 10.00 | 2 | 98 | 180 |
| 10.50 | 95 | 5 | 180 |
| 12.00 | 95 | 5 | 180 |

The stationary phase used is an X-Bridge C18 column, 5 µm, 50×65 mm, ambient temperature.

INDICATIONS

As has been found, the combinations according to the invention containing a compound of formula 1 and at least one NSAID are characterised by their wide range of applications in the therapeutic field. Particular mention should be made of those applications for which the combinations according to the invention are preferably suited on account of their pharmaceutical efficacy as PDE4 inhibitors. Examples include respiratory or gastrointestinal diseases or complaints, inflammatory diseases of the joints, skin or eyes, cancers, and also diseases of the peripheral or central nervous system.

Particular mention should be made of the prevention and treatment of diseases of the airways and of the lung which are accompanied by increased mucus production, inflammations and/or obstructive diseases of the airways. Examples include acute, allergic or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, paediatric asthma, bronchiectases, pulmonary fibrosis, ARDS (acute adult respiratory distress syndrome), bronchial oedema, pulmonary oedema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis or mucoviscidosis, or alpha1-antitrypsin deficiency.

Also deserving special mention is the treatment of inflammatory diseases of the gastrointestinal tract. Examples include acute or chronic inflammatory changes in gall bladder inflammation, Crohn's disease, ulcerative colitis, inflammatory pseudopolyps, juvenile polyps, colitis cystica profunda, pneumatosis cystoides intestinales, diseases of the bile duct and gall bladder, e.g. gallstones and conglomerates, for the treatment of inflammatory diseases of the joints such as rheumatoid arthritis or inflammatory diseases of the skin and eyes.

Preferential mention should also be made of the treatment of cancers. Examples include all forms of acute and chronic leukaemias such as acute lymphatic and acute myeloid leukaemia, chronic lymphatic and chronic myeloid leukaemia, and bone tumours such as osteosarcoma and all types of glioma such as oligodendroglioma and glioblastoma.

Preferential mention should also be made of the prevention and treatment of diseases of the peripheral or central nervous system. Examples of these include depression, bipolar or manic depression, acute and chronic anxiety states, schizophrenia, Alzheimer's disease, Parkinson's disease, acute and chronic multiple sclerosis or acute and chronic pain as well as injuries to the brain caused by stroke, hypoxia or craniocerebral trauma.

Particularly preferably the present invention relates to the use of the combinations according to the invention for preparing a medicament for the treatment of inflammatory or obstructive diseases of the upper and lower respiratory tract including the lungs, such as for example allergic rhinitis, chronic rhinitis, bronchiectasis, cystic fibrosis, idiopathic pulmonary fibrosis, fibrosing alveolitis, COPD, chronic bronchitis, chronic sinusitis, asthma, Crohn's disease, ulcerative colitis, particularly COPD, chronic bronchitis and asthma.

It is most preferable to use the combinations according to the invention for the treatment of inflammatory and obstructive diseases such as COPD, chronic bronchitis, chronic sinusitis, asthma, Crohn's disease, ulcerative colitis, particularly COPD, chronic bronchitis and asthma.

It is also preferable to use the combinations according to the invention for the treatment of diseases of the peripheral or central nervous system such as depression, bipolar or manic depression, acute and chronic anxiety states, schizophrenia, Alzheimer's disease, Parkinson's disease, acute and chronic multiple sclerosis, amyotrophic lateral sclerosis (ALS) or acute and chronic pain as well as injuries to the brain caused by stroke, hypoxia or craniocerebral trauma.

An outstanding aspect of the formulations according to the invention containing a combination of a compound of formula 1 and at least one NSAID is the reduced profile of side effects compared with formulations that contain the same compound of formula 1 in the same amount in the absence of an NSAID. Side effects that frequently occur when taking a PDE4 inhibitor preferentially include, inter alia, diarrhoea, nausea and vomiting. In the rat model further side effects were observed after the administration of PDE4 inhibitor, such as for example weight loss, leukocytosis and neutrophilia, as well as diarrhoea.

By a reduced profile of side effects is meant, within the scope of the invention, in particular being able to administer a therapeutically effective dose of a PDE4 inhibitor in a pharmaceutical composition according to the invention without inducing to any appreciable extent in the patient the or at least one of the side effects commonly observed when PDE4 inhibitors are administered. It is particularly preferable to administer a therapeutically effective amount of a PDE4 inhibitor in the composition according to the invention at every stage of the course of the disease without triggering the typical PDE4 inhibitor-mediated side effects of diarrhoea, weight loss, leukocytosis or neutrophilia. In a particular aspect the present invention relates to the administration of a therapeutically effective amount of the pharmaceutical composition according to the invention at every stage of the course of the disease without triggering the typical PDE4 inhibitor-mediated side effect of diarrhoea to any appreciable degree.

Experiments on the rat model described hereinafter show that the pharmaceutical compositions according to the invention containing a PDE4 inhibitor and at least one NSAID substantially reduce or even totally prevent many of the side effects which occur when the corresponding PDE4 inhibitor is administered on its own.

EXPERIMENTAL METHOD

Experiment 1

Diclofenac Provides Protection Against Roflumilast-Mediated Effects Such as Weight Loss, Leukocytosis, and Neutrophilia Six male Wistar rats in each group were treated for four days with the following substances (all substances are given p.o.=orally):
Group 1 ("control group"): Six male Wistar rats were given a daily dose of 0.5% Natrosol (placebo) at the times 0800, 1300 and 1700 hours.
Group 2 ("roflumilast group"): Six male Wistar rats were given a daily dose of 0.5% Natrosol (placebo) at 0800 and 1700 hours and 10 mg/kg roflumilast (PDE4 inhibitor) at 1300 hours.
Group 3 ("roflumilast+diclofenac group"): Six male Wistar rats were given a daily dose of 1 mg/kg diclofenac (NSAID) at the times 0800 and 1700 hours and 10 mg/kg roflumilast (PDE4 inhibitor) at 1300 hours.
Group 4 ("diclofenac group"): Six male Wistar rats were given a daily dose of 1 mg/kg diclofenac (NSAID) at the times 0800 and 1700 hours and 0.5% Natrosol (placebo) at 1300 hours.

For pharmacokinetic analysis (determining the plasma levels of the substances) on day 4 one rat from each group was used; these rats were no longer available for other parameters under investigation. The same applied to one rat from the roflumilast group which died between day 4 and day 5 of the experiment.

FIG. 1A shows the body weights of the rats from the different groups as a percentage change from the time of the first administration (=day 1, 0800 hours (=time $t_0$)). The average±standard deviation of the body weights at time $t_0$ was 355±17 g.

At the end of the experiment (95 hours after $t_0$ (=the time of the first administration on day 1, 0800)) the proportion of white blood cells (×1000 cells/μl blood, FIG. 1B, left-hand Figure) and the proportion of neutrophils (in % of white blood cells, FIG. 1B, right-hand Figure) were determined from the blood of 4 or 5 of the rats from the individual groups.

Experiment 2

Diclofenac Provides Protection Against Roflumilast-Mediated Effects Such as Diarrhoea Six male Wistar rats in each group were treated for four days with the following substances (all substances are given p.o.=orally):
Group 1 ("control group"): Six male Wistar rats were given a daily dose of 0.5% Natrosol (placebo) at the times 0800, 1300 and 1700 hours.
Group 2 ("roflumilast group"): Six male Wistar rats were given a daily dose of 0.5% Natrosol (placebo) at 0800 and 1700 hours and 10 mg/kg roflumilast (PDE4 inhibitor) at 1300 hours.
Group 3 ("roflumilast+diclofenac group"): Six male Wistar rats were given a daily dose of 1 mg/kg diclofenac (NSAID) at the times 0800 and 1700 hours and 10 mg/kg roflumilast (PDE4 inhibitor) at 1300 hours.
Group 4 ("diclofenac group"): Six male Wistar rats were given a daily dose of 1 mg/kg diclofenac (NSAID) at the times 0800 and 1700 hours and 0.5% Natrosol (placebo) at 1300 hours.

For pharmacokinetic analysis (determining the plasma levels of the substances) on day 4 one rat from each group was used; these rats were no longer available for other parameters under investigation. The same applied to one rat from the roflumilast group which died between day 4 and day 5 of the experiment.

At the end of the experiment (95 hours after $t_0$ (=the time of the first administration on day 1, 0800 hours)) the rats from the individual groups were examined phenotypically and histopathologically for the presence of multifocal perivascular mononuclear infiltration (=inflammation parameter) in the mesentery and for the proliferation of fibroblasts in the mesentery. In addition, the occurrence of diarrhoea in the rats from the different groups was noted. The findings are summarised in Table 1 as follows:

TABLE 1

Phenotypical and histopathological findings

| Parameter | Control (group 1) | roflumilast (group 2) | roflumilast + diclofenac (group 3) | diclofenac (group 4) |
|---|---|---|---|---|
| Diarrhoea | 0/6 (=0 out of 6 animals) | 5/6 | 0/6 | 0/6 |
| Mesentery: multifocal perivascular mononuclear infiltration (=inflammation parameter) | 0/5 | 4/4 | 0/5 | 0/5 |
| Mesentery: Proliferation of fibroblasts | 0/5 | 4/4 | 0/5 | 0/5 |

To summarise, it can be stated that the PDE4 inhibitor-mediated side effects such as weight loss (FIG. 1A), leukocytosis (FIG. 1B, on the left), neutrophilia (FIG. 1B, on the right) and diarrhoea (including the presence of inflammation parameters and the proliferation of fibroblasts in the mesentery) observed in the roflumilast group can be substantially reduced or prevented (often even reduced to the level found in the control group), by co-administering an NSAID such as diclofenac (cf. roflumilast+diclofenac group) simultaneously or only a few hours apart. The parameters measured after the administration of diclofenac alone were found to be very similar to the control groups.

Experiment 3

The COX-2 Selective Inhibitor Lumiracoxib, but not the COX-1 Selective Inhibitor SC-560, Provides Protection from Roflumilast-Mediated Effects Such as Weight Loss, Leukocytosis and Neutrophilia Six male Wistar rats in each group were treated for four days with the following substances (all substances are given p.o.=orally):
Group 1 ("control group"): Six male Wistar rats were given a daily dose of 0.5% Natrosol (placebo) at the times 0800, 1300 and 1700 hours.
Group 2 ("roflumilast group"): Six male Wistar rats were given a daily dose of 0.5% Natrosol (placebo) at 0800 and 1700 hours and 10 mg/kg roflumilast (PDE4 inhibitor) at 1300 hours.
Group 3 ("roflumilast+SC-560 group"): Six male Wistar rats were given a daily dose of 2 mg/kg SC-560 (NSAID, selective for COX-1) at the times 0800 and 1700 hours and 10 mg/kg roflumilast (PDE4 inhibitor) at 1300 hours.
Group 4 ("roflumilast+lumiracoxib group"): Six male Wistar rats were given a daily dose of 2 mg/kg lumiracoxib (NSAID, selective for COX-2) at the times 0800 and 1700 hours and 10 mg/kg of reflumilast (PDE4 inhibitor) at 1300 hours.
Group 5 ("SC-560 group"): Six male Wistar rats were given a daily dose of 2 mg/kg SC-560 (NSAID, selective for COX-1) at the times 0800 and 1700 hours and 0.5% Natrosol at 1300 hours.
Group 6 ("lumiracoxib group"): Six male Wistar rats were given a daily dose of 2 mg/kg lumiracoxib (NSAID, selective for COX-2) at the times 0800 and 1700 hours and 0.5% Natrosol at 1300 hours.

For pharmacokinetic analysis (determining the plasma levels of the substances) on day 4 one rat from each group was used; these rats were no longer available for other parameters under investigation.

FIG. 2A shows the body weights of the rats from the different groups as a percentage change from the time of the first administration (=day 1, 0800 hours (=time $t_0$)). The average±standard deviation of the body weights at time $t_0$ was 306±11 g.

At the end of the experiment (95 hours after $t_0$ (=the time of the first administration on day 1, 0800 hours)) the proportion of white blood cells (×1000 cells/µl blood, FIG. 2B, left-hand Figure) and the proportion of neutrophils (in % of white blood cells, FIG. 2B, right-hand Figure) were determined from the blood of 5 of the rats from the individual groups.

Experiment 4

The COX-2 Selective Inhibitor Lumiracoxib, but not the COX-1 Selective Inhibitor SC-560, Provides Protection from Roflumilast-Mediated Effects Such as Diarrhoea Six male Wistar rats in each group were treated for four days with the following substances (all substances are given p.o.=orally):
Group 1 ("control group"): Six male Wistar rats were given a daily dose of 0.5% Natrosol (placebo) at the times 0800, 1300 and 1700 hours.
Group 2 ("roflumilast group"): Six male Wistar rats were given a daily dose of 0.5% Natrosol (placebo) at 0800 and 1700 hours and 10 mg/kg roflumilast (PDE4 inhibitor) at 1300 hours.
Group 3 ("roflumilast+SC-560 group"): Six male Wistar rats were given a daily dose of 2 mg/kg SC-560 (NSAID, selective for COX-1) at the times 0800 and 1700 hours and 10 mg/kg roflumilast (PDE4 inhibitor) at 1300 hours.
Group 4 ("roflumilast+lumiracoxib group"): Six male Wistar rats were given a daily dose of 2 mg/kg lumiracoxib (NSAID, selective for COX-2) at the times 0800 and 1700 hours and 10 mg/kg of roflumilast (PDE4 inhibitor) at 1300 hours.
Group 5 ("SC-560 group"): Six male Wistar rats were given a daily dose of 2 mg/kg SC-560 (NSAID, selective for COX-1) at the times 0800 and 1700 hours and 0.5% Natrosol at 1300 hours.
Group 6 ("lumiracoxib group"): Six male Wistar rats were given a daily dose of 2 mg/kg lumiracoxib (NSAID, selective for COX-2) at the times 0800 and 1700 hours and 0.5% Natrosol at 1300 hours.

For pharmacokinetic analysis (determining the plasma levels of the substances) on day 4 one rat from each group was used; these rats were no longer available for other parameters under investigation.

At the end of the experiment (95 hours after $t_0$ (=the time of the first administration on day 1, 0800 hours)) the rats from the individual groups were examined phenotypically and histopathologically for the presence of multifocal perivascular mononuclear infiltration (=inflammation parameter) in the mesentery and for the proliferation of fibroblasts in the mesentery. In addition, the occurrence of diarrhoea in the rats from the different groups was noted. The findings are summarised in Table 2 as follows:

TABLE 2

Phenotypical and histopathological findings

| Parameter | control (group 1) | roflumilast (group 2) | roflumilast + SC-560 (group 3) | roflumilast + lumiracoxib (group 4) | SC-560 (group 5) | lumiracoxib (group 6) |
|---|---|---|---|---|---|---|
| Diarrhoea | 0/6 (=0 von 6 Tieren) | 2/6 | 0/6 | 0/6 | 0/6 | 0/6 |
| Mesentery: multifocal perivascular mononuclear infiltration (= inflammation parameter) | 0/5 | 5/5 | 4/5 | 0/5 | 0/5 | 0/5 |
| Mesentery: Proliferation of fibroblasts | 0/5 | 5/5 | 4/5 | 0/5 | 0/5 | 0/5 |

To summarise, it can be stated that the PDE4 inhibitor-mediated side effects such as weight loss (FIG. 2A), leukocytosis (FIG. 2B, on the left), neutrophilia (FIG. 2B, on the right) and diarrhoea (including the presence of inflammation parameters and the proliferation of fibroblasts in the mesentery) observed in the roflumilast group can be substantially reduced or prevented (often even reduced to the level found in the control group), by co-administering a COX-2 selective NSAID such as lumiracoxib (cf. roflumilast+lumiracoxib) simultaneously or only a few hours apart. The COX-1 selective NSAID SC-560 has absolutely no protective effect on weight loss, leukocytosis and neutrophilia and only a very slight protective effect on the histopathological findings (multifocal perivascular mononuclear infiltration or proliferation of fibroblasts in the mesentery). It is difficult to make any pronouncements as to the effect of SC-560 on diarrhoea because in this experiment, in the roflumilast group, diarrhoea was only found per se in two animals. The parameters measured after the administration of SC-560 or lumiracoxib alone were found to be very similar to the control groups.

To sum up, it can be concluded that the protective effect of an NSAID on the PDE4 inhibitor-mediated side effects are based on the inhibition of COX-2.

Formulations

The active substance combinations of 1 and 2 are preferably administered orally. For this purpose the ingredients (1) and (2) have to be presented in suitable oral preparations.

Suitable oral forms for administration are for example tablets, capsules, solutions, syrups or emulsions. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension.

It is particularly preferable if the preparations are administered once or twice a day. Suitable tablets may be obtained, for example, by mixing the active substance(s) with known excipients, for example inert diluents such as calcium carbonate, calcium phosphate, microcrystalline cellulose, sorbitol, mannitol, isomaltose or lactose, disintegrants such as corn starch, crosslinked polyvinyl pyrrolidone, crosslinked sodium carboxymethylcellulose, sodium starch glycolate or alginic acid, binders such as starch, hydroxypropylmethylcellulose, polyvinylpyrrolidone or gelatine, lubricants, such as magnesium stearate or talc, and/or agents for delaying release, such as hydroxypropylcellulose, hydroxypropylmethylcellulose, ethylcellulose, aminomethacrylate, polyvinylpyrrolidone-polyvinylacetate copolymer, carboxymethylcellulose or polyvinylacetate. The tablets may also comprise several layers.

Coated tablets or film-coated tablets may be prepared accordingly by coating cores produced analogously to the tablets with substances normally used for tablet or film coatings, for example collidone or shellac, gum arabic, talc, titanium dioxide, sugar, hydroxypropylmethyl cellulose, ethycellulose, cellulose acetate phthalate, polymethacrylate, polyethyleneglycol, polyvinyl alcohol, polyvinyl alcohol-polyethyleneglycol copolymers or polyvinylacetate. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

Examples of Formulations:

The following formulation examples for combined formulations are intended to serve to illustrate the invention without restricting it thereto. In particular, the active substances 1 and 2 may also be present in separate formulations and administered separately within a time window of not more than 6 hours.

| | | |
|---|---|---|
| 1) | 0.05 mg | active substance 1 |
| | 500 mg | acetylsalicylic acid (active substance 2) |
| | 100 mg | lactose |
| | 329.95 mg | microcrystalline cellulose |
| | 30 mg | polyvinylpyrrolidone |
| | 30 mg | crosslinked polyvinylpyrrolidone |
| | 10 mg | magnesium stearate |
| | 1000 mg | |
| 2) | 0.1 mg | active substance 1 |
| | 500 mg | acetylsalicylic acid (active substance 2) |
| | 100 mg | lactose |
| | 329.9 mg | microcrystalline cellulose |
| | 30 mg | crosslinked polyvinylpyrrolidone |
| | 30 mg | polyvinylpyrrolidone |
| | 10 mg | magnesium stearate |
| | 1000 mg | |
| 3) | 0.5 mg | active substance 1 |
| | 500 mg | acetylsalicylic acid (active substance 2) |
| | 100 mg | lactose |
| | 329.5 mg | microcrystalline cellulose |
| | 30 mg | crosslinked polyvinylpyrrolidone |
| | 30 mg | polyvinylpyrrolidone |
| | 10 mg | magnesium stearate |
| | 1000 mg | |
| 4) | 5 mg | active substance 1 |
| | 500 mg | acetylsalicylic acid (active substance 2) |
| | 100 mg | lactose |
| | 325 mg | microcrystalline cellulose |
| | 30 mg | crosslinked polyvinylpyrrolidone |
| | 30 mg | polyvinylpyrrolidone |
| | 10 mg | magnesium stearate |
| | 1000 mg | |
| 5) | 20 mg | active substance 1 |
| | 500 mg | acetylsalicylic acid (active substance 2) |
| | 100 mg | lactose |
| | 310 mg | microcrystalline cellulose |
| | 30 mg | crosslinked polyvinylpyrrolidone |
| | 30 mg | polyvinylpyrrolidone |
| | 10 mg | magnesium stearate |
| | 1000 mg | |
| 6) | 0.05 mg | active substance 1 |
| | 25 mg | diclofenac (active substance 2) |
| | 170 mg | lactose |
| | 269.95 mg | microcrystalline cellulose |
| | 15 mg | crosslinked polyvinylpyrrolidone |
| | 15 mg | polyvinylpyrrolidone |
| | 5 mg | magnesium stearate |
| | 500 mg | |
| 7) | 0.1 mg | active substance 1 |
| | 25 mg | diclofenac (active substance 2) |
| | 170 mg | lactose |
| | 269.9 mg | microcrystalline cellulose |
| | 15 mg | crosslinked polyvinylpyrrolidone |
| | 15 mg | polyvinylpyrrolidone |
| | 5 mg | magnesium stearate |
| | 500 mg | |
| 8) | 0.5 mg | active substance 1 |
| | 25 mg | diclofenac (active substance 2) |
| | 170 mg | lactose |
| | 269.5 mg | microcrystalline cellulose |
| | 15 mg | crosslinked polyvinylpyrrolidone |
| | 15 mg | polyvinylpyrrolidone |
| | 5 mg | magnesium stearate |
| | 500 mg | |
| 9) | 5 mg | active substance 1 |
| | 25 mg | diclofenac (active substance 2) |
| | 170 mg | lactose |
| | 265 mg | microcrystalline cellulose |
| | 15 mg | crosslinked polyvinylpyrrolidone |
| | 15 mg | polyvinylpyrrolidone |
| | 5 mg | magnesium stearate |
| | 500 mg | |
| 10) | 20 mg | active substance 1 |
| | 25 mg | diclofenac (active substance 2) |
| | 170 mg | lactose |
| | 240 mg | microcrystalline cellulose |
| | 15 mg | crosslinked polyvinylpyrrolidone |
| | 15 mg | polyvinylpyrrolidone |
| | 5 mg | magnesium stearate |
| | 500 mg | |
| 11) | 0.05 mg | active substance 1 |
| | 15 mg | meloxicam (active substance 2) |
| | 170 mg | lactose |
| | 279.95 mg | microcrystalline cellulose |
| | 15 mg | crosslinked polyvinylpyrrolidone |
| | 15 mg | polyvinylpyrrolidone |
| | 5 mg | magnesium stearate |
| | 500 mg | |
| 12) | 0.1 mg | active substance 1 |
| | 15 mg | meloxicam (active substance 2) |
| | 170 mg | lactose |
| | 279.9 mg | microcrystalline cellulose |
| | 15 mg | crosslinked polyvinylpyrrolidone |
| | 15 mg | polyvinylpyrrolidone |
| | 5 mg | magnesium stearate |
| | 500 mg | |
| 13) | 0.5 mg | active substance 1 |
| | 15 mg | meloxicam (active substance 2) |
| | 170 mg | lactose |
| | 279.5 mg | microcrystalline cellulose |
| | 15 mg | crosslinked polyvinylpyrrolidone |
| | 15 mg | polyvinylpyrrolidone |
| | 5 mg | magnesium stearate |
| | 500 mg | |
| 14) | 5 mg | active substance 1 |
| | 15 mg | meloxicam (active substance 2) |
| | 170 mg | lactose |
| | 275 mg | microcrystalline cellulose |
| | 15 mg | crosslinked polyvinylpyrrolidone |
| | 15 mg | polyvinylpyrrolidone |
| | 5 mg | magnesium stearate |
| | 500 mg | |
| 15) | 20 mg | active substance 1 |
| | 15 mg | meloxicam (active substance 2) |
| | 170 mg | lactose |
| | 260 mg | microcrystalline cellulose |
| | 15 mg | crosslinked polyvinylpyrrolidone |
| | 15 mg | polyvinylpyrrolidone |
| | 5 mg | magnesium stearate |
| | 500 mg | |
| 16) | 0.05 mg | active substance 1 |
| | 500 mg | naproxen (active substance 2) |

|  |  |  |
|---|---|---|
|  | 100 mg | lactose |
|  | 329.95 mg | microcrystalline cellulose |
|  | 30 mg | crosslinked polyvinylpyrrolidone |
|  | 30 mg | polyvinylpyrrolidone |
|  | 10 mg | magnesium stearate |
|  | 1000 mg | |
| 17) | 0.1 mg | active substance 1 |
|  | 500 mg | naproxen (active substance 2) |
|  | 100 mg | lactose |
|  | 329.9 mg | microcrystalline cellulose |
|  | 30 mg | crosslinked polyvinylpyrrolidone |
|  | 30 mg | polyvinylpyrrolidone |
|  | 10 mg | magnesium stearate |
|  | 1000 mg | |
| 18) | 0.5 mg | active substance 1 |
|  | 500 mg | naproxen (active substance 2) |
|  | 100 mg | lactose |
|  | 329.5 mg | microcrystalline cellulose |
|  | 30 mg | crosslinked polyvinylpyrrolidone |
|  | 30 mg | polyvinylpyrrolidone |
|  | 10 mg | magnesium stearate |
|  | 1000 mg | |
| 19) | 5 mg | active substance 1 |
|  | 500 mg | naproxen (active substance 2) |
|  | 100 mg | lactose |
|  | 325 mg | microcrystalline cellulose |
|  | 30 mg | crosslinked polyvinylpyrrolidone |
|  | 30 mg | polyvinylpyrrolidone |
|  | 10 mg | magnesium stearate |
|  | 1000 mg | |
| 20) | 20 mg | active substance 1 |
|  | 500 mg | naproxen (active substance 2) |
|  | 100 mg | lactose |
|  | 310 mg | microcrystalline cellulose |
|  | 30 mg | crosslinked polyvinylpyrrolidone |
|  | 30 mg | polyvinylpyrrolidone |
|  | 10 mg | magnesium stearate |
|  | 1000 mg | |
| 21) | 0.05 mg | active substance 1 |
|  | 200 mg | ibuprofen (active substance 2) |
|  | 100 mg | lactose |
|  | 258.95 mg | microcrystalline cellulose |
|  | 18 mg | crosslinked polyvinylpyrrolidone |
|  | 18 mg | polyvinylpyrrolidone |
|  | 5 mg | magnesium stearate |
|  | 600 mg | |
| 22) | 0.1 mg | active substance 1 |
|  | 200 mg | ibuprofen (active substance 2) |
|  | 100 mg | lactose |
|  | 258.9 mg | microcrystalline cellulose |
|  | 18 mg | crosslinked polyvinylpyrrolidone |
|  | 18 mg | polyvinylpyrrolidone |
|  | 5 mg | magnesium stearate |
|  | 600 mg | |
| 23) | 0.5 mg | active substance 1 |
|  | 200 mg | ibuprofen (active substance 2) |
|  | 100 mg | lactose |
|  | 258.5 mg | microcrystalline cellulose |
|  | 18 mg | crosslinked polyvinylpyrrolidone |
|  | 18 mg | polyvinylpyrrolidone |
|  | 5 mg | magnesium stearate |
|  | 600 mg | |
| 24) | 5 mg | active substance 1 |
|  | 200 mg | ibuprofen (active substance 2) |
|  | 100 mg | lactose |
|  | 254 mg | microcrystalline cellulose |
|  | 18 mg | crosslinked polyvinylpyrrolidone |
|  | 18 mg | polyvinylpyrrolidone |
|  | 5 mg | magnesium stearate |
|  | 600 mg | |
| 25) | 20 mg | active substance 1 |
|  | 200 mg | ibuprofen (active substance 2) |
|  | 100 mg | lactose |
|  | 239 mg | microcrystalline cellulose |
|  | 18 mg | crosslinked polyvinylpyrrolidone |
|  | 18 mg | polyvinylpyrrolidone |
|  | 5 mg | magnesium stearate |
|  | 600 mg | |

The finely ground active substance, lactose and some of the microcrystalline cellulose are mixed together. The mixture is screened, then moistened with a solution of polyvinylpyrrolidone in water, kneaded, wet-granulated and dried. The granules, the rest of the microcrystalline cellulose and the crosslinked polyvinylpyrrolidone are screened and mixed together. Then the magnesium stearate is screened in and briefly mixed in. The mixture is compressed to form tablets of suitable shape and size.

The invention claimed is:
1. A drug combination comprising:
(a) a compound of formula 1

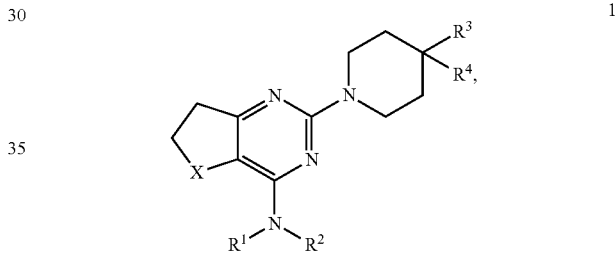

wherein:
X is SO or $SO_2$;
$R^1$ is H or $C_{1-6}$-alkyl;
$R^2$ is H or a group selected from $C_{1-10}$-alkyl and $C_{2-6}$-alkenyl which are optionally substituted by one or more groups selected from halogen and $C_{1-3}$-fluoroalkyl or which are optionally substituted by one or more groups selected from $OR^{2.1}$, $COOR^{2.1}$, $CONR^{2.2}R^{2.3}$, $SR^{2.1}$, $SO_2$—$R^{2.1}$, $SO_2$—$R^{2.1}$, $C_{6-10}$-aryl, -het, hetaryl, a mono- or bicyclic-$C_{3-10}$-cycloalkyl, $CH_2$—$NR^{2.2}R^{2.3}$, and $NR^{2.2}R^{2.3}$, each of which in turn is optionally substituted by one or more groups selected from OH, halogen, $OR^{2.1}$, oxo, $CF_3$, $CHF_2$, $CH_2F$, $C_{1-6}$-alkyl, $C_{1-6}$-alkanol, $C_{6-10}$-aryl, $COOR^{2.1}$, $CH_2$—$NR^{2.2}R^{2.3}$, and $NR^{2.2}R^{2.3}$,
$R^2$ is a mono- or polycyclic $C_{3-10}$ cycloalkyl, optionally singly or multiply bridged by $C_{1-3}$-alkyl groups and optionally substituted by a group selected from branched or unbranched $C_{1-6}$-alkanol, $C_{1-3}$-fluoroalkyl, $C_{1-3}$-alkylene-$OR^{2.1}$, $OR^{2.1}$, $COOR^{2.1}$, —$SO_2$—$NR^{2.2}R^{2.3}$, het, —NH—CO—O—($C_{1-6}$-alkyl), —NH—CO—($C_{1-6}$-alkyl), —NH—CO—O—($C_{6-10}$-aryl), —NH—CO—($C_{6-10}$-aryl), —NH—CO—O-hetaryl, —NH—CO-hetaryl, —NH—CO—O—($C_{1-3}$-alkylene)-($C_{6-10}$-aryl), —NH—CO—($C_{1-3}$-alkylene)-($C_{6-10}$-aryl), —N($C_{1-3}$-alkyl)-CO—($C_{1-6}$-alkyl), —N($C_{1-3}$-alkyl)-CO—O—($C_{6-10}$-aryl), —N($C_{1-3}$- alkyl)-CO—($C_{6-10}$-aryl), —N($C_{1-3}$-alkyl)-CO—O-hetaryl, —N($C_{1-3}$-alkyl)-CO-hetaryl, —N($C_{1-3}$-alkyl)-CO—O—($C_{1-3}$-alkylene)-($C_{6-10}$-aryl), —N($C_{1-3}$-alkyl)-CO—($C_{1-3}$-alkylene)-($C_{6-10}$-aryl), $C_{6-10}$-aryl, $C_{1-6}$-alkyl, $C_{6-10}$-aryl-$C_{1-6}$-alkylene, hetaryl-$C_{1-6}$-alkylene, mono- or bicyclic $C_{3-10}$ cycloalkyl, and $NR^{2.2}R^{2.3}$, each optionally substituted by one or more groups selected from OH, $OR^{2.1}$, oxo, halogen, $CF_3$, $CHF_2$, $CH_2F$, $C_{1-6}$-alkyl, $C_{6-10}$-aryl, and $NR^{2.2}R^{2.3}$, $R^2$ is a mono- or polycyclic $C_{6-10}$-aryl, optionally substituted by OH, SH, or halogen or by one or more groups selected from $OR^{2.1}$, $COOR^{2.1}$, $NR^{2.2}R^{2.3}$, $CH_2$—$NR^{2.2}R^{2.3}$, $C_{3-10}$-cycloalkyl, het, $C_{1-6}$-alkyl, $C_{1-3}$-fluoroalkyl, $CF_3$, $CHF_2$, $CH_2F$, $C_{6-10}$-aryl-$C_{1-6}$-alkylene, het-$C_{1-6}$-alkylene, hetaryl-$C_{1-6}$-alkylene, $C_{6-10}$-aryl, $SO_2$—$CH_3$, $SO_2$—$CH_2CH_3$, and $SO_2$—$NR^{2.2}R^{2.3}$, each of which in turn is optionally substituted by one or more groups selected from OH, $OR^{2.1}$, $CF_3$, $CHF_2$, $CH_2F$, oxo, halogen, $CF_3$, $CHF_2$, $CH_2F$, $C_{1-6}$-alkyl, $C_{6-10}$-aryl, and $NR^{2.2}R^{2.3}$, $R^2$ is a group selected from het and hetaryl, each optionally substituted by one or more groups selected from halogen, OH, oxo, $CF_3$, $CHF_2$ and $CH_2F$ or by one or more groups selected from $OR^{2.1}$, $C_{1-3}$-alkylene-$OR^{2.1}$, $SR^{2.1}$, $SO_2$—$R^{2.1}$, $SO_2$—$R^{2.1}$, $COOR^{2.1}$, $COR^{2.1}$, $C_{1-6}$-alkanol, mono- or bicyclic $C_{3-10}$-cycloalkyl, $C_{6-10}$-aryl, $C_{1-6}$-alkyl, $C_{6-10}$-aryl-$C_{1-6}$-alkylene, hetaryl-$C_{1-6}$-alkylene, het, hetaryl, $C_{1-3}$-alkylene-$OR^{2.1}$, and $NR^{2.2}R^{2.3}$, each of which in turn is optionally substituted by one or more groups selected from OH, $OR^{2.1}$, oxo, halogen, $CF_3$, $CHF_2$, $CH_2F$, $C_{1-6}$-alkyl, $C_{6-10}$-aryl, and $NR^{22}R^{23}$, or $NR^1R^2$ together are a heterocyclic $C_{4-7}$ ring optionally bridged, which contains 1, 2, or 3 heteroatoms selected from N, O, and S and which is optionally substituted by one or more groups selected from OH, $OR^{2.1}$, $C_{1-3}$-alkylene-$O^{R.1}$, oxo, halogen, $C_{1-6}$-alkyl, $C_{6-10}$-aryl, $COOR^{2.1}$, $CH_2$—$NR^{2.2}$—COO—$R^{2.1}$, $CH_2$—$NR^{2.2}$—CO—$R^{2.1}$, $CH_2$—$NR^{2.2}$—CO—$CH_2$—$NR^{2.2}R^{2.3}$, $CH_2$—$NR^{2.2}$—$SO_2$—$C_{1-3}$-alkyl, $CH_2$—$NR^{2.2}$—$SO_2$—$NR^{2.2}R^{2.3}$, $CH_2$—$NR^{2.2}$—CO—$NR^{2.2}R^{2.3}$, CO—$NR^{2.2}R^{2.3}$, $CH_2$—$NR^{2.2}R^{2.3}$, and $NR^{2.2}R^{2.3}$;

$R^3$ is a $C_{6-10}$-aryl optionally substituted in the ortho, para, or meta position by one, two, or three groups independently selected from fluorine, chlorine, bromine, hydroxy, CN, $C_{1-6}$-alkyl, $C_{1-3}$-fluoroalkyl, —$C_{1-3}$-alkylene-$OR^{2.1}$, —$C_{1-3}$-alkylene-$NR^{2.2}R^{2.3}$, —$NR^{2.2}R^{2.3}$, O—$R^{2.1}$, SO—$R^{2.1}$, $SO_2$—$R^{2.1}$, $COOR^{2.1}$, —CO—NH—($C_{1-6}$-alkylene)-hetaryl, hetaryl, —CO—N($CH_3$)-het, —CO—N($CH_3$)—($C_{1-3}$-alkylene)-het, —CO—N($CH_3$)—($C_{1-3}$-alkylene)-hetaryl, —CO—N($C_{3-7}$-cycloalkyl)-het, —CO—$NR^{2.2}R^{2.3}$, ⁻CO—NH—($C_{1-6}$-alkylene)-het, $NR^{2.2}$—CO—$R^{2.1}$, $C_{6-10}$-aryl, $C_{6-10}$-aryl-$C_{1-2}$-alkylene, het-$C_{1-2}$-alkylene, -het, —CO-het, CO—N($CH_3$)—$C_{3-7}$-cycloalkyl, $C_{3-7}$-cycloalkyl, $C_{3-7}$-cycloalkyl-$C_{1-2}$-alkylene, hetaryl-$C_{1-2}$-alkylene, and hetaryl, wherein this group is optionally substituted by one or more groups selected from OH, halogen, —$C_{1-3}$-fluoroalkyl, oxo, methyl, and phenyl, $R^3$ is het or hetaryl, each optionally substituted by one or more groups selected from halogen, $C_{1-3}$-fluoroalkyl, CN, OH, oxo, —$C_{1-6}$-alkyl, —$C_{1-3}$-alkylene-$NR^{23}$, —$NR^{2.2}R^{2.3}$, SO—$R^{2.1}$, $SO_2$—$R^{2.1}$, ⁻O—$R^{2.1}$, —$COOR^{2.1}$, $SO_2$—($CH_3$), $SO_2$—($CH_2$—$CH_3$), $C_{6-10}$-aryl, het, $C_{3-7}$-cycloalkyl, and hetaryl, each of which in turn is optionally substituted by one or more groups selected from OH, halogen, —$C_{1-3}$-fluoroalkyl, $C_{1-6}$-alkyl, $C_{6-10}$-aryl, —COO($C_{1-3}$-alkyl), and O—($C_{1-3}$-alkyl), $R^3$ is —O—$R^{3.1}$, wherein $R^{3.1}$ is a group selected from $C_{1-6}$-alkyl, —$C_{6-10}$-aryl, —$C_{1-3}$-alkylene-$C_{6-10}$-aryl, hetaryl, and het, each of which is optionally substituted in the ortho, para, or meta position by one, two or three groups independently selected from fluorine, chlorine, bromine, hydroxy, CN, $C_{1-6}$-alkyl, $C_{1-3}$-fluoroalkyl, CO—($C_{1-5}$-alkyl), —CO—($C_{1-3}$-fluoroalkyl), —CO—NH—($C_{1-6}$-alkylene)-hetaryl, —CO—N($C_{1-3}$-alkyl)-($C_{1-6}$-alkylene)-hetaryl, —CO—N($C_{1-3}$-alkyl)-het, —CO—N($C_{3-7}$-cycloalkyl)-het, —$C_{1-3}$-alkylene-$OR^{2.1}$, —$C_{1-3}$-alkylene-$NR^{2.2}R^{2.3}$, —$NR^{2.2}R^{2.3}$, O—$R^{2.1}$; $SO_2$—$R^{2.1}$, COOH COO—($C_{1-4}$-alkyl), —O—$C_{1-3}$-alkylene-N($C_{1-3}$-alkyl)$_2$, CO—$NR^{2.2}R^{2.3}$, $NR^{2.2}$—CO—$R^{2.1}$, $C_{6-10}$-aryl, $C_{6-10}$-aryl-$C_{1-2}$-alkylene, het-$C_{1-2}$-alkylene, —CO-het, het, —CO—$C_{3-7}$-cycloalkyl, —CO—N($C_{1-3}$-alkyl)-$C_{3-7}$-cycloalkyl, $C_{3-7}$-cycloalkyl-$C_{1-2}$-alkylene, hetaryl-$C_{1-2}$-alkylene, and hetaryl, each of which in turn is optionally substituted by 1, 2, 3, or 4 groups independently selected from F, Cl, Br, methyl, O-methyl, ethyl, O-ethyl, OH, oxo, and $CF_3$; and $R^4$ is H, CN, OH, $CF_3$, $CHF_2$, $CH_2F$, F, methyl, ethyl, —O—($C_{1-3}$-alkyl), —$C_{1-3}$-alkylene-OH, —COO($C_{1-3}$-alkyl), —CO-het, -($C_{1-2}$-alkylene)-NH—$SO_2$—($C_{1-2}$-alkyl), -($C_{1-2}$-alkylene)-N($C_{1-3}$-alkyl)-$SO_2$—($C_{1-2}$-alkyl), -($C_{1-2}$-alkylene)-O-($C_{1-2}$-alkylene)-$C_{6-10}$-aryl, —$C_{1-3}$-alkylene-O—$C_{1-3}$-alkyl, -($C_{1-2}$-alkylene)-N($C_{1-3}$-alkyl)-CO—($C_{1-2}$-alkyl), CO—($C_{1-3}$-alkylene)-O-($C_{1-3}$-alkyl), —$C_{1-3}$-alkylene-NH—CO—($C_{1-3}$-alkyl), —$C_{1-3}$-alkylene-NH—CO—($C_{1-3}$-alkylene)-N($C_{1-3}$-alkyl)$_2$, —O—($C_{1-2}$-alkylene)-($C_{6-10}$-aryl), —$C_{1-3}$-alkylene-NH—CO—($C_{1-3}$-alkylene)-O-($C_{1-3}$-alkyl), —CO—($C_{6-10}$-aryl), -($C_{1-2}$-alkylene)-N($C_{1-3}$-alkyl)-CO—($C_{1-2}$-alkylene)-O-($C_{1-3}$-alkyl), wherein the aryl in the above groups is in turn optionally substituted by one or more additional groups selected from F, Cl, Br, methyl, ethyl, propyl, isopropyl, cyclopropyl, —O-methyl, —O-ethyl, —O-propyl, —O—isopropyl, —O-cyclopropyl, —OH, and $CF_3$, or $R^3$ and $R^4$ together form a mono- or bicyclic, unsaturated, saturated, or partly saturated heterocyclic group which contains 1, 2, or 3 heteroatoms selected from N, O, and S and which is optionally substituted by one or more groups selected from halogen, OH, oxo, $C_{1-3}$-fluoroalkyl, CN, $C_{1-6}$-alkyl, —O—$R^{2.1}$, —$COOR^{2.1}$, SO—$R^{2.1}$, $SO_2$—$R^{2.1}$, ⁻$C_{1-3}$-alkylene-$NR^{2.2}R^{2.3}$, —$NR^{2.2}R^{2.3}$, $C_{6-10}$-aryl, $C_{3-7}$-cycloalkyl, het, and hetaryl, and wherein:

het is a three- to eleven-membered, mono- or bicyclic, saturated or partly saturated, optionally anellated or optionally bridged heterocyclic group which contains 1, 2, 3, or 4 heteroatoms independently selected from N, S, or O, hetaryl is a five- to ten-membered, mono- or bicyclic, optionally annelated heteroaryl, which contains 1, 2, 3, or 4 heteroatoms independently selected from N, S, or O, cycloalkyl is saturated or partly saturated, $R^{2.1}$ is H or a group selected from $C_{1-6}$-alkyl, $C_{1-6}$-alkanol, $C_{1-3}$-haloalkyl, mono- or bicyclic, —$C_{3-10}$-cycloalkyl, $C_{6-10}$-aryl-$C_{1-6}$-alkylene, hetaryl-$C_{1-6}$-alkylene, het-$C_{1-6}$-alkylene, $C_{3-10}$-cycloalkyl-$C_{1-6}$-alkylene, a mono- or bicyclic $C_{6-10}$-aryl, heteroaryl, and -het, each optionally substituted by one or more groups selected from OH, O—($C_{1-3}$-alkyl), halogen, $C_{1-6}$-alkyl, and $C_{6-10}$-aryl, and $R^{2.2}$ and $R^{2.3}$ are each independently H or a group selected from $C_{1-6}$-alkyl, mono- or bicyclic $C_{3-10}$ cycloalkyl, $C_{6-10}$-aryl-$C_{1-6}$-alkylene, hetaryl-$C_{1-6}$-alkylene, mono- or bicyclic $C_{6-10}$-aryl, het, hetaryl, CO—$NH_2$, CO—$NHCH_3$, —CO—$N(CH_3)_2$, $SO_2$—($C_1$-$C_2$-alkyl), CO—$R^{2.1}$, and $COOR^{2.1}$, each optionally substituted by one or more groups selected from OH, halogen, $C_{1-6}$-alkyl, $C_{6-10}$-aryl, and $COOR^{2.1}$; and (b) an NSAID selected from the group consisting of aceclofenac (2.1), acemetacin (2.2), acetylsalicylic acid (2.3), alclofenac (2.4), alminoprofen (2.5), amfenac (2.6), ampiroxicam (2.7), antolmetinguacil (2.8), anirolac (2.9), antrafenine (2.10), azapropazone (2.11), benorilate (2.12), bermoprofen (2.13), bindarit (2.14), bromfenac (2.15), bucloxinic acid (2.16), bucolom (2.17), bufexamac (2.18), bumadizone (2.19), butibufen (2.20), butixirate (2.21), carbasalate calcium (2.22), carprofen (2.23), choline magnesium trisalicylate (2.24), celecoxib (2.25), cinmetacin (2.26), cinnoxicam (2.27), clidanac (2.28), clobuzarit (2.29), deboxamet (2.30), dexibuprofen (2.31), dexketoprofen (2.32), diflunisal (2.34), droxicam (2.35), eltenac (2.36), enfenamic acid (2.37), etersalate (2.38), etodolac (2.39), etofenamat (2.40), etoricoxib (2.41), feclobuzon (2.42), felbinac (2.43), fenbufen (2.44), fenclofenac (2.45), fenoprofen (2.46), fentiazac (2.47), fepradinol (2.48), feprazone (2.49), flobufen (2.50), floctafenin (2.51), flufenamic acid (2.52), flufenisal (2.53), flunoxaprofen (2.54), flurbiprofenaxetil (2.56), furofenac (2.57), furprofen (2.58), glucametacin (2.59), ibufenac (2.60), indometacinfarnesil (2.64), indoprofen (2.65), isoxepac (2.66), isoxicam (2.67), ketorolac (2.69), lobenzarit (2.70), lonazolac (2.71), lomoxicam (2.72), loxoprofen (2.73), lumiracoxib (2.74), meclofenamic acid (2.75), meclofen, mefenamic acid (2.76), meloxicam (2.77), mesalazin (2.78), miroprofen (2.79), mofezolac (2.80), nabumetone (2.81), naproxen (2.82), nifluminic acid (2.83), olsalazine (2.84), oxaprozin (2.85), oxipinac (2.86), oxyphenbutazone (2.87), parecoxib (2.88), phenylbutazone (2.89), pelubiprofen (2.90), pimeprofen (2.91), pirazolac (2.92), piroxicam (2.93), pirprofen (2.94), pranoprofen (2.95), prifelon (2.96), prinomod (2.97), proglumetacin (2.98), proquazone (2.99), protizinic acid (2.100), rofecoxib (2.101), romazarit (2.102), salicylamide (2.103), salicylic acid (2.104), salmistein (2.105), salnacedin (2.106), salsalate (2.107), sulindac (2.108), sudoxicam (2.109), suprofen (2.110), talniflumat (2.111), tenidap (2.112), tenosal (2.113), tenoxicam (2.114), tepoxalin (2.115), tiaprofenic acid (2.116), taramide (2.117), tilnoprofenarbamel (2.118), timegadine (2.119), tinoridine (2.120), tiopinac (2.121), tolfenamic acid (2.122), tolmetin (2.123), ufenamate (2.124), valdecoxib (2.125), ximoprofen (2.126), zaltoprofen (2.127), and zoliprofen (2.128).

2. The drug combination according to claim 1, wherein:
X is SO;
$R^1$ is H;
$R^2$ is H or $C_{1-6}$-alkyl optionally substituted by one or more groups selected from F, Cl, $CF_3$, $CHF_2$, or $CH_2F$, or optionally substituted by one or more groups selected from $OR^{2.1}$, $COOR^{2.1}$, $CONR^{2.2}R^{2.3}$, $SR^{2.1}$, SO—$R^{2.1}$, $SO_2$—$R^{2.1}$, phenyl, het, hetaryl, a monocyclic $C_{3-7}$-cycloalkyl, $CH_2$—$NR^{2.2}R^{2.3}$, and $NR^{2.2}R^{2.3}$, each of which in turn is optionally substituted by one or more groups selected from OH, F, Cl, Br, $CF_3$, $CHF_2$, $CH_2F$, $OR^{2.1}$, oxo, methyl, ethyl, propyl, isopropyl, methanol, ethanol, phenyl, $COOR^{2.1}$, $CH_2$—$NR^{2.2}R^{2.3}$, and $NR^{2.2}R^{2.3}$, $R^2$ is a monocyclic $C_{3-7}$ cycloalkyl optionally substituted by a group selected from $C_{1-2}$-alkanol, $C_{1-3}$-fluoroalkyl, $C_{1-3}$-alkylene-$OR^{2.1}$, $OR^{2.1}$, $COOR^{2.1}$, $SO_2$—$NR^{2.2}R^{2.3}$, -het, —NH—CO—O-(phenyl), methyl, ethyl, propyl, isopropyl, phenyl, phenyl-$C_{1-2}$-alkylene, -hetaryl-$C_{1-2}$-alkylene, monocyclic $C_{3-7}$ cycloalkyl, and $NR^{2.2}R^{2.3}$, each of which is optionally substituted by one or more groups selected from OH, $OR^{2.1}$, oxo, F, Cl, $CF_3$, $CHF_2$, $CH_2F$, methyl, ethyl, propyl, isopropyl, phenyl, and $NR^{2.2}R^{2.3}$, $R^2$ is a phenyl optionally substituted by OH, SH, F, Cl, or Br or by one or more groups selected from $OR^{2.1}$, $COOR^{2.1}$, $NR^{2.2}R^{2.3}$, $CH_2$—$NR^{2.2}R^{2.3}$, monocyclic $C_{3-7}$-cycloalkyl, -het, methyl, ethyl, propyl, isopropyl, $CF_3$, $CHF_2$, $CH_2F$, phenyl-$C_{1-2}$-alkylene, het-$C_{1-2}$-alkylene, hetaryl-$C_{1-2}$-alkylene, phenyl, $SO_2$—$CH_3$, $SO_2$—$CH_2CH_3$, and $SO_2$—$NR^{2.2}R^{2.3}$, each of which in turn is optionally substituted by one or more groups selected from OH, $OR^{2.1}$, oxo, F, Cl, $CF_3$, $CHF_2$, $CH_2F$, methyl, ethyl, propyl, isopropyl, phenyl, and $NR^{2.2}R^{2.3}$, or $R^2$ is het or hetaryl, each optionally substituted by one or more groups selected from F, Cl, OH, oxo, $CF_3$, $CHF_2$, and $CH_2F$ or by one or more groups selected from $OR^{2.1}$, $C_{1-3}$-alkylene-$OR^{2.1}$, $SR^{2.1}$, SO—$R^{2.1}$, $SO_2$—$R^{2.1}$, $COOR^{2.1}$, $COR^{2.1}$, methanol, ethanol, monocyclic $C_{3-7}$-cycloalkyl, phenyl, methyl, ethyl, propyl, isopropyl, phenyl-$C_{1-2}$-alkylene, hetaryl-$C_{1-2}$-alkylene, -het, -hetaryl, and $NR^{2.2}R^{2.3}$, each of which in turn is optionally substituted by one or more groups selected from OH, $OR^{2.1}$, oxo, F, Cl, $CF_3$, $CHF_2$, $CH_2F$, methyl, ethyl, propyl, isopropyl, butyl, isobutyl, phenyl, and $NR^{2.2}R^{2.3}$;

$R^3$ is a naphthalene or phenyl, each optionally substituted in the ortho, para, or meta position by one or two groups independently selected from fluorine, chlorine, bromine, hydroxy, CN, methyl, ethyl, propyl, isopropyl, cyclopropyl, $CF_3$, $CHF_2$, $CH_2F$, —$OCH_3$, $OCH_2CH_3$, $SO_2$—$CH_3$, SO—$CH_3$, $COOCH_3$, $COOCH_2CH_3$, —CO—NH-(methylene)-hetaryl, —CO—NH-(ethylene)-hetaryl, —CO—NH-hetaryl, —CO—$N(CH_3)$-het, —CO—$N(CH_3)$-(methylene)-het, —CO—$N(CH_3)$-(ethylene)-het, —CO—$N(CH_3)$-(methylene)-hetaryl, —CO—$N(CH_3)$-(ethylene)-hetaryl, —CO—N(cyclopropyl)-het, CO—$NH_2$, $CONH(CH_3)$, $CON(CH_3)_2$, —CO—NH-(methylene)-het, —CO—NH-(ethylene)-het, —NH—CO-methyl, $NCH_3$—CO-methyl, NH—CO-ethyl, $NCH_3$—CO-ethyl, —NH—CO-propyl, $NCH_3$—CO— propyl, —NH—CO-isopropyl, $NCH_3$—CO-isopropyl, phenyl, phenyl-methylene, phenyl-ethylene, het-methylene, het-ethylene, -het, —CO-het, —CO—$N(CH_3)$-het, CO—$N(CH_3)$-cyclopropyl, $C_{3-7}$-cycloalkyl, $C_{3-7}$-cycloalkyl-methylene, $C_{3-7}$-cycloalkyl-ethylene, hetaryl-methylene, hetaryl-ethylene, -hetaryl, $CH_2$—$NH_2$, $CH_2$—$NH(CH_3)$, $CH_2$—$N(CH_3)_2$, —$NH_2$, —$NH(CH_3)$, and —$N(CH_3)_2$, each group optionally substituted by one or more groups selected from OH, F, Cl, —$CF_3$, $CHF_2$, $CH_2F$, oxo, methyl, and phenyl, $R^3$ is a group selected from het and hetaryl, each optionally substituted by one or more groups selected from F, Cl, Br, $CF_3$, $CHF_2$, $CH_2F$, CN, OH, oxo, methyl, ethyl, propyl, isopropyl, butyl, isobutyl, cyclopropyl, —O-methyl, —O-ethyl, —O-propyl, —O— isopropyl, —COO-methyl, —COO-ethyl, —COO-propyl, —COO-isopropyl, SO—(CH₃), SO—(CH₂—CH₃), SO₂—(CH₃), SO₂—(CH₂—CH₃), phenyl, CH₂—NH₂, CH₂—NH (CH₃), CH₂—N(CH₃)₂, —NH₂, —NH(CH₃), —N(CH₃)₂, het, and hetaryl, each of which in turn is optionally substituted by one or more groups selected from OH, F, Cl, CF₃, CHF₂, CH₂F, methyl, ethyl, propyl, isopropyl, phenyl, —COO-methyl, —COO-ethyl, O-methyl, and O-ethyl, or R³ is —O—R³·¹, wherein R³·¹ is a group selected from —C₁₋₃-alkyl, -phenyl, —C₁₋₃-alkylene-phenyl, hetaryl and het, which is optionally substituted in the ortho, para, or meta position by one, two or three groups independently selected from fluorine, chlorine, bromine, hydroxy, CN, methyl, ethyl, propyl, isopropyl, butyl, isobutyl, CF₃, CHF₂, CH₂F, CO-(methyl), CO-(ethyl), CO-(propyl), CO-(isopropyl), —CO—(CF₃), —CO—NH-(methylene)-hetaryl, —CO—NH-(ethylene)-hetaryl, —CO—N(CH₃)-(methylene)-hetaryl, —CO—N(CH₃)-(ethylene)-hetaryl, —CO—N(CH₃)-(propylene)-hetaryl, —CO—N(CH₃)-(isopropylene)-hetaryl, —CO—N(CH₃)-het, —CO—N(cyclopropyl)-het, N(C₅₋₇-cycloalkyl)-het, -methylene-O-methyl, -ethylene-O-methyl, -propylene-O-methyl, -methylene-O-ethyl, -ethylene-O-ethyl, -propylene-O-ethyl, -methylene-NH₂, -methylene-NHCH₃, -methylene-N(CH₃)₂, -ethylene-NH₂, -ethylene-NHCH₃, -ethylene-N(CH₃)₂, NH₂, N(CH₃)₂, NHCH₃, —O-methyl, O-ethyl, O-propyl, 0-isopropyl, O-butyl, 0-isobutyl, —SO—CH₃, SO-ethyl, —SO-propyl, —SO-isopropyl, SO₂-methyl, —SO₂-ethyl, SO₂-propyl, SO₂-isopropyl, COOH, COO-(methyl), COO-(ethyl), COO-(propyl), COO-(isopropyl), —O-methylene-N(methyl)₂, —O-ethylene-N(methyl)₂, —O-methylene-N(ethyl)₂, —O-ethylene-N(ethyl)₂, CO—NH₂, CO—NH(CH₃), CO—N(CH₃)₂, —NH—CO-methyl, —NCH₃—CO-methyl, —NH—CO-ethyl, NCH₃—CO-ethyl, phenyl, phenyl-methylene, phenyl-ethylene, het-methylene, het-ethylene, —CO-het, het, —CO—O₅₋₇-cycloalkyl, —CO-cyclopropyl, —CO—N(CH₃)—O₅₋₇-cycloalkyl, —CO—N(CH₃)-cyclopropyl, C₅₋₇-cycloalkyl, cyclopropyl, C₅₋₇-cycloalkyl-methylene, C₅₋₇-cycloalkyl-ethylene, cyclopropyl-methylene, cyclopropyl-ethylene, hetaryl-methylene, hetaryl-ethylene, and hetaryl, each of which in turn is optionally substituted by 1, 2, 3, or 4 groups independently selected from F, Cl, Br, methyl, O-methyl, ethyl, O-ethyl, OH, oxo, and CF₃, and R⁴ is H, CN, OH, CF₃, CHF₂, CH₂F, F, methyl, ethyl, O-methyl, O-ethyl, -methylene-OH, -ethylene-OH, -propylene-OH, -isopropylene-OH, —COO(methyl), —COO(ethyl), —COO(propyl), —COO(isopropyl), —CO-het, -(methylene)-NH—SO₂-(methyl), -(methylene)-NH—SO₂-(ethyl), -(ethylene)-NH—SO₂-(methyl), -(ethylene)-NH—SO₂-(ethyl), -(methylene)-N(CH₃)-SO₂-(methyl), -(methylene)-N(CH₃)—SO₂-(ethyl), -(ethylene)-N(CH₃)-SO₂-(methyl), -(ethylene)-N(CH₃)-SO₂-(ethyl), -(methylene)-O-(methylene)-phenyl, -(methylene)-O-(ethylene)-phenyl, -(ethylene)-O-(methylene)-phenyl, -(ethylene)-O-(ethylene)-phenyl, -methylene-O-methyl, -methylene-O-ethyl, -ethylene-O-methyl, -ethylene-O-ethyl, -(methylene)-N(CH₃)—CO-(methyl), -(methylene)-N(CH₃)-CO-(ethyl), -(ethylene)-N(CH₃)—CO-(methyl), -(ethylene)-N(CH₃)—CO-(ethyl), —NH—CO-(methylene)-O-(methyl), —NH—CO-(methylene)-O-(ethyl), —NH—CO-(ethylene)-O-(methyl), —NH—CO-(ethylene)-O-(ethyl), -methylene-NH—CO-(methyl), -methylene-NH—CO-(ethyl), -ethylene-NH—CO-(methyl), -ethylene-NH—CO-(ethyl), -methylene-NH—CO-(methylene)-N(methyl)₂, -methylene-NH—CO-(ethylene)-N(methyl)₂, -ethylene-NH—CO-(methylene)-N(methyl)₂, -ethylene-NH—CO-(ethylene)-N(methyl)₂, -methylene-NH—CO-(methylene)-O-(methyl), -methylene-NH—CO-(ethylene)-O-(methyl), -ethylene-NH—CO-(methylene)-O-(methyl), -ethylene-NH—CO-(ethylene)-O-(methyl), -methylene-NH—CO-(methylene)-O-(ethyl), -methylene-NH—CO-(ethylene)-O-(ethyl), -ethylene-NH—CO-(methylene)-O-(ethyl), -ethylene-NH—CO-(ethylene)-O-(ethyl), -(methylene)-N(CH₃)—CO-(methylene)-O-(methyl), -(methylene)-N(CH₃)—CO-(ethylene)-O-(methyl), -(ethylene)-N(CH₃)-CO-(methylene)-O-(methyl), -(methylene)-N(CH₃)-CO-(methylene)-O-(ethyl), -(methylene)-N(CH₃)—CO-(ethylene)-O-(ethyl), -(ethylene)-N(CH₃)-CO-(methylene)-O-(ethyl), —O-(methylene)-phenyl, —O-(ethylene)-phenyl, or —CO-phenyl, wherein the phenyl in the above groups are optionally substituted by one or more other groups selected from F, Cl, Br, methyl, ethyl, propyl, —O-methyl, —O-ethyl, —O— propyl, —OH, and CF₃, or R³ and R⁴ together form a mono- or bicyclic, unsaturated, saturated, or partly saturated heterocyclic group which contains 1, 2, or 3 heteroatoms selected from N, O, and S and which is optionally substituted by one or more groups selected from F, Cl, Br, OH, oxo, CF₃, CHF₂, CH₂F, CN, methyl, ethyl, propyl, isopropyl, cyclopropyl, COO-methyl, —COO-ethyl, O-methyl, O-ethyl, SO₂—(CH₃), SO₂—(CH₂CH₃), SO—(CH₃), SO—(CH₂CH₃), CH₂—NH₂, CH₂—NH(CH₃), CH₂—N(CH₃)₂, —NH₂, —NH(CH₃), —N(CH₃)₂, phenyl, C₅₋₇-cycloalkyl, het, and hetaryl, and wherein:

het is a three- to seven-membered, monocyclic, saturated or partly saturated heterocyclic group which contains 1, 2 or 3 heteroatoms independently selected from N, S, or O, hetaryl is a five- to six-membered, monocyclic, aromatic heteroaryl which contains 1, 2, or 3 heteroatoms independently selected from N, S, or O, cycloalkyl is saturated or partly saturated, R²¹ is H or a group selected from methyl, ethyl, propyl, isopropyl, methanol, ethanol, monocyclic C₃₋₇ cycloalkyl, phenyl-C₁₋₂-alkylene, -hetaryl-C₁₋₂-alkylene, -het-C₁₋₂-alkylene, C₃₋₇-cycloalkyl-C₁₋₂-alkylene, phenyl, hetaryl and het, which is optionally substituted by one or more groups selected from OH, F, Cl, methyl, ethyl, propyl, isopropyl, O-methyl, O-ethyl, O-propyl, O-isopropyl, and phenyl, R²·² and R²·³ are each independently H or a group selected from methyl, ethyl, propyl, isopropyl, monocyclic C₃₋₇-cycloalkyl, phenyl-C₁₋₃-alkylene, hetaryl-C₁₋₃-alkylene, phenyl, -het, -hetaryl, CO—NH₂, CO—NHCH₃, CON(CH₃)₂, SO₂—(C₁₋₂-alkyl), CO—R²·¹, and COOR²·¹, each optionally substituted by one or more groups selected from OH, F, Cl, methyl, ethyl, propyl, isopropyl, phenyl, and COOR²·¹.

3. The drug combination according to claim 1, wherein:
R² is a group according to formula 3

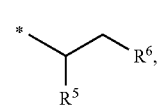

wherein:
R⁶ is OH or NH₂, and R⁵ is a group selected from C₁₋₄-alkyl, a five- to six-membered heteroaryl with 1, 2 or 3 heteroatoms selected from among S, O, and N, and phenyl, which is optionally substituted by one or more groups selected from OH, F, Br, $OR^{2.1}$, oxo, methyl, ethyl, methanol, ethanol, phenyl, $COOR^{2.1}$, $CH_2$—$NR^{2.2}R^{2.3}$, and $NR^{2.2}R^{2.3}$.

4. The drug combination according to claim 3, wherein:
$R^5$ is methyl, ethyl, propyl, or isopropyl.

5. The drug combination according to claim 1, wherein:
$R^2$ is a monocyclic three-, four-, five-, six-, or seven-membered cycloalkyl ring optionally substituted in the spiro position by a group selected from —$CH_2$—$OR^{2.1}$, branched or unbranched $C_{2-6}$-alkylene-$OR^{2.1}$, methyl, ethyl, propyl, isopropyl, butyl, isobutyl, cyclopropyl, —$CF_3$, $CHF_2$, $CH_2F$, and $C_{2-4}$-fluoroalkyl, wherein $R^{2.1}$ is methyl, ethyl, propyl, isopropyl, butyl, or isobutyl.

6. The drug combination according to claim 1, wherein:
$R^2$ is a cyclopropyl optionally substituted by another group selected from —$NH_2$, $CH_2$—$NH_2$, —$NH(CH_3)$, —$N(CH_3)_2$, methyl, ethyl, propyl, isopropyl, —NH—CO-(tert-butyl), —NH—CO—O-(tert-butyl), —$N(CH_3)$—CO-(tert-butyl), —$N(CH_3)$—CO—O-(tert-butyl), —$CF_3$, —$CHF_2$, $CH_2F$, F, Cl, and Br.

7. The drug combination according to claim 1, wherein:
$R^2$ is a cyclopropyl, or
$R^2$ is a phenyl optionally substituted in one or both meta positions by one or more groups selected from methyl, ethyl, propyl, isopropyl, cyclopropyl, F, Cl, Br, OH, $OR^{2.1}$, $COOR^{2.1}$, $CF_3$, $CHF_2$, $CH_2F$, $NH_2$, $NH(CH_3)$, and $N(CH_3)_2$, wherein $R^{2.1}$ is H, methyl, or ethyl.

8. The drug combination according to claim 1, wherein:
$R^2$ is a group selected from monocyclic, saturated three-, four-, five-, six-, or seven-membered heterocyclic groups with 1, 2, or 3 heteroatoms selected in each case from N, O, and S, optionally substituted by one or more groups selected from fluorine, chlorine, bromine, $CF_3$, $CHF_2$, $CH_2F$, OH, and oxo, or by one or more groups selected from $OR^{2.1}$, $C_{1-3}$-alkylene-$OR^{2.1}$, $sR^{2.1}$, SO—$R^{2.1}$, $SO_2$—$R^{2.1}$, $COOR^{2.1}$, $COR^{2.1}$, $C_{1-6}$-alkanol, $C_{3-10}$-cycloalkyl, phenyl, $C_{1-6}$-alkyl, phenyl-$C_{1-6}$-alkylene, hetaryl-$C_{1-6}$-alkylene, het, hetaryl, and $NR^{2.2}R^{2.3}$, each of which in turn is optionally substituted by one or more groups selected from OH, $OR^{2.1}$, oxo, F, Cl, $CF_3$, $CHF_2$, $CH_2F$, $C_{1-6}$-alkyl, phenyl, and $NR^{2.2}R^{2.3}$.

9. The drug combination according to claim 8, wherein:
$R^2$ is a group selected from a monocyclic, saturated six-membered heterocyclic group with a heteroatom selected from N, O, and S, optionally substituted by one or more groups selected from F, Cl, Br, $CF_3$, $CHF_2$, $CH_2F$, OH, oxo, $NH_2$, $NHCH_3$, $N(CH_3)_2$, methyl, ethyl, propyl, isopropyl, cyclopropyl, methoxy, and ethoxy.

10. The drug combination according to claim 9, wherein:
$R^2$ is piperidine or tetrahydropyran, each optionally substituted by one or more groups selected from F, Cl, Br, OH, $CF_3$, $CHF_2$, $CH_2F$, $NH_2$, $NHCH_3$, $N(CH_3)_2$, oxo, methyl, and methoxy.

11. The drug combination according to claim 1, wherein:
$R^3$ is a naphthalene or phenyl, each optionally substituted by one, two, or three groups independently selected from fluorine, chlorine, bromine, hydroxy, CN, methyl, ethyl, propyl, isopropyl, cyclopropyl, $CF_3$, $CHF_2$, $CH_2F$, —$OCH_3$, $OCH_2CH_3$; $SO_2$—$CH_3$, $SO_2$—$CH_2CH_3$, $COOCH_3$, and CO—O—$CH_2CH_3$.

12. The drug combination according to claim 1, wherein:
$R^3$ is het or hetaryl, each optionally substituted by one or more groups selected from F, Cl, Br, $CF_3$, $CHF_2$, $CH_2F$, CN, OH, oxo, methyl, ethyl, propyl, isopropyl, butyl, isobutyl, cyclopropyl, $C_{5-7}$-cycloalkyl, —O-methyl, —O-ethyl, —O-propyl, —O-isopropyl, —COO-methyl, —COO-ethyl, —COO-propyl, —COO-isopropyl, $SO_2$—$(CH_3)$, $SO_2$—$(CH_2$—$CH_3)$, SO—$(CH_3)$, SO—$(CH_2$—$CH_3)$, phenyl, —$CH_2$—$NH_2$, —$CH_2$—$NHCH_3$, —$CH_2$—$N(CH_3)_2$, $NH_2$, $NHCH_3$, $N(CH_3)_2$, het, and hetaryl, each of which in turn is optionally substituted with one or more groups selected from OH, F, Cl, Br, $CF_3$, $CHF_2$, $CH_2F$, methyl, ethyl, propyl, isopropyl, phenyl, —COO-methyl, —COO-ethyl, —COO-propyl, —COO-isopropyl, O-methyl, O-ethyl, O-propyl, and O-isopropyl; and
$R^4$ is H, CN, OH, $CF_3$, $CHF_2$, $CH_2F$, F, methyl, ethyl, O-methyl, or O-ethyl,
and wherein:
het is a three- to seven-membered, monocyclic, saturated or partly saturated heterocyclic group or a seven- to eleven-membered, bicyclic, anellated, saturated or partly saturated heterocyclic group which contains 1, 2, or 3 heteroatoms independently selected from N, S, or O, and
hetaryl is a five- to six-membered, monocyclic, aromatic heteroaryl or a seven- to eleven-membered, bicyclic, annelated, aromatic heteroaryl which contains in each case 1, 2, or 3 heteroatoms independently selected from N, S, or O.

13. The drug combination according to claim 12, wherein:
$R^3$ is indole, dihydroindole, quinazoline, dihydroquinazoline, tetrahydroquinazoline, benzoisoxazole, dihydrobenzoisoxazole, benzoxazine, dihydrobenzoxazine, benzothiazole, dihydrobenzothiazole, triazolopyridine, dihydrotriazolopyridine, benzofuran, dihydrobenzofuran, isobenzofuran, or dihydroisobenzofuran, each of which is optionally substituted by one or more groups selected from F, Cl, Br, $CF_3$, $CHF_2$, $CH_2F$, CN, OH, oxo, methyl, ethyl, propyl, isopropyl, butyl, isobutyl, cyclopropyl, —O— methyl, —O-ethyl, —O-propyl, —O-isopropyl, —COO-methyl, —COO-ethyl, —COO-propyl, —COO-isopropyl, $SO_2$—$(CH_3)$, $SO_2$—$(CH_2$—$CH_3)$, SO—$(CH_3)$, SO—$(CH_2$—$CH_3)$, phenyl, —$CH_2$—$NH_2$, —$CH_2$—$NHCH_3$, —$CH_2$—$N(CH_3)_2$, $NH_2$, $NHCH_3$, $N(CH_3)_2$, furanyl, and pyridinyl, each of which in turn is optionally substituted by one or more groups selected from OH, F, Cl, Br, $CF_3$, $CHF_2$, $CH_2F$, methyl, ethyl, propyl, isopropyl, phenyl, —COO-methyl, —COO-ethyl, O-methyl, and O-ethyl.

14. The drug combination according to claim 11, wherein:
$R^3$ is imidazole, dihydroimidazole, oxadiazole, oxadiazolidine, pyrazole, pyridine, or dihydropyrazole, each of which is optionally substituted by one or more groups selected from F, Cl, Br, $CF_3$, $CHF_2$, $CH_2F$, CN, OH, oxo, methyl, ethyl, propyl, isopropyl, butyl, isobutyl, cyclopropyl, —O-methyl, —O-ethyl, —O-propyl, —O-isopropyl, —COO-methyl, —COO-ethyl, —COO-propyl, —COO-isopropyl, $SO_2$—$(CH_3)$, $SO_2$—$(CH_2$—$CH_3)$, SO—$(CH_3)$, SO—$(CH_2$—$CH_3)$, phenyl, —$CH_2$—$NH_2$, —$CH_2$—$NHCH_3$, —$CH_2$—$N(CH_3)_2$, $NH_2$, $NHCH_3$, $N(CH_3)_2$, furanyl, and pyridinyl, each of which in turn is optionally substituted by one or more groups selected from OH, F, Cl, Br, $CF_3$, $CHF_2$, $CH_2F$, methyl, ethyl, propyl, isopropyl, phenyl, —COO-methyl, —COO-ethyl, O-methyl, and O-ethyl.

15. The drug combination according to claim 1, wherein:
$R^3$ and $R^4$ together form a mono- or bicyclic, unsaturated or partly saturated, three- to eleven-membered heterocyclic group which contains 1, 2 or 3 heteroatoms selected from N, O, and S, and which is optionally substituted by one or more groups selected from F, Cl, Br, OH, oxo, $CF_3$, $CHF_2$, $CH_2F$, CN, methyl, ethyl, propyl, isopropyl, cyclopropyl, COO-methyl, —COO-ethyl, O-methyl, O-ethyl, SO₂—(CH₃), SO₂—(CH₂—CH₃), SO—(CH₃), SO—(CH₂—CH₃), phenyl, —CH₂—NH₂, —CH₂NHCH₃, —CH₂—N(CH₃)₂, NH₂, NHCH₃, N(CH₃)₂, a saturated or partly saturated, five- to six-membered heterocyclic group, and a five- to six-membered heteroaryl.

16. The drug combination according to claim 15, wherein: $R^3$ and $R^4$ together form tetrahydroquinazoline, tetrahydrobenzoxazine, dihydroindole, or dihydroisobenzofuran, each of which is optionally substituted by one or more groups selected from F, Cl, Br, OH, oxo, CF₃, CHF₂, CH₂F, CN, methyl, ethyl, propyl, isopropyl, cyclopropyl, COO-methyl, —COO-ethyl, O-methyl, O-ethyl, SO₂—(CH₃), SO₂—(CH₂—CH₃), phenyl, —CH₂—NH₂, —CH₂NHCH₃, —CH₂—N(CH₃)₂, NH₂, NHCH₃, N(CH₃)₂, a saturated or partly saturated, five or six-membered heterocyclic group, and a five or six-membered heteroaryl.

17. The drug combination according to claim 1, wherein: $R^3$ is —O—$R^{3.1}$, wherein $R^{3.1}$ is a group selected from methyl, ethyl, propyl, isopropyl, butyl, isobutyl, pentyl, isopentyl, -phenyl, -methylene-phenyl, -ethylene-phenyl, -propylene-phenyl, -isopropylene-phenyl, hetaryl, and het, each optionally substituted in the ortho, para, or meta position by one, two or three groups independently selected from fluorine, chlorine, bromine, hydroxy, CN, methyl, ethyl, propyl, isopropyl, butyl, isobutyl, —CF₃, CHF₂, CH₂F, CO-(methyl), CO-(ethyl), CO-(propyl), CO-(isopropyl), CO-(butyl), CO-(isobutyl), —CO—(CF₃), —CO—(CH₂F), —CO—(CHF₂), —CO—NH-(methylene)-hetaryl, —CO—NH-(ethylene)-hetaryl, —CO—NH-(propylene)-hetaryl, —CO—NH-(isopropylene)-hetaryl, —CO—N(CH₃)-(methylene)-hetaryl, —CO—N(CH₃)-(ethylene)-hetaryl, —CO—N(CH₃)-(propylene)-hetaryl, —CO—N(CH₃)-(isopropylene)-hetaryl, —CO—N(CH₃)-het, —CO—N(C₃₋₇-cycloalkyl)-het, -methylene-O-methyl, -ethylene-O-methyl, -methylene-O-ethyl, -ethylene-O-ethyl, -methylene-NH₂, -ethylene-NH₂, -methylene-NHCH₃, -ethylene-NHCH₃, -methylene-N(CH₃)₂, -ethylene-N(CH₃)₂, —NH₂, —NHCH₃, —N(CH₃)₂, —O-methyl, —O-ethyl, —O-propyl, —O—isopropyl, —SO—CH₃, —SO—(CH₂CH₃), SO₂—CH₃, —SO₂—(CH₂CH₃) COOH, COO-(methyl), COO-(ethyl), COO-(propyl), COO-(isopropyl), —O-methylene-N(methyl)₂, —O-ethylene-N(methyl)₂, —O-methylene-N(ethyl)₂, —O-ethylene-N(ethyl)₂, CO—NH₂, CO—NHCH₃, CO—N(CH₃)₂, NH—CO-methyl, NCH₃—CO-methyl, NH—CO-ethyl, N(CH₃)—CO-ethyl, phenyl, phenyl-methylene, phenyl-ethylene, het-methylene, het-ethylene, —CO-het, het, —CO—C₄₋₇-cycloalkyl, —CO-cyclopropyl, —CO—N(CH₃)-cyclopropyl, —CO—N(CH₃)—C₄₋₇-cycloalkyl, C₄₋₇-cycloalkyl, cyclopropyl, C₄₋₇-cycloalkyl-methylene, cyclopropyl-methylene, C₄₋₇-cycloalkyl-ethylene, cyclopropyl-ethylene, hetaryl-methylene, hetaryl-ethylene, and hetaryl, each of which in turn is optionally substituted by 1, 2, 3, or 4 groups independently selected from F, Cl, Br, methyl, O-methyl, ethyl, O-ethyl, OH, oxo, and CF₃.

18. The drug combination according to claim 1, wherein: $R^4$ is H, CN, OH, CF₃, CHF₂, CH₂F, F, methyl, ethyl, O-methyl, O-ethyl, -methylene-OH, -ethylene-OH, -propylene-OH, -isopropylene-OH, —COO(methyl), —COO(ethyl), —COO-(isopropyl), —CO-het, -(methylene)-NH—SO₂-(methyl), -(methylene)-NH—SO₂-(ethyl), -(ethylene)-NH—SO₂-(methyl), -(ethylene)-NH—SO₂-(ethyl), -(methylene)-N(CH₃)—SO₂-(methyl), -(methylene)-N(CH₃)—SO₂-(ethyl), -(ethylene)-N(CH₃)-SO₂-(methyl), -(ethylene)-N(CH₃)—SO₂-(ethyl), -(methylene)-O-(methylene)-phenyl, -(methylene)-O-(ethylene)-phenyl, -(ethylene)-O-(methylene)-phenyl, -(ethylene)-O-(ethylene)-phenyl, -methylene-O-methyl, -methylene-O-ethyl, -ethylene-O-methyl, -ethylene-O-ethyl, -(methylene)-N(CH₃)-CO-(methyl), -(methylene)-N(CH₃)—CO-(ethyl), -(ethylene)-N(CH₃)-CO-(methyl), -(ethylene)-N(CH₃)—CO-(ethyl), —NH—CO-(methylene)-O-(methyl), —NH—CO-(methylene)-O-(ethyl), —NH—CO-(ethylene)-O-(methyl), —NH—CO-(ethylene)-O-(ethyl), -methylene-NH—CO-(methyl), -methylene-NH—CO-(ethyl), -ethylene-NH—CO-(methyl), -ethylene-NH—CO-(ethyl), -methylene-NH—CO-(methylene)-N(methyl)₂, -methylene-NH—CO-(ethylene)-N(methyl)₂, -ethylene-NH—CO-(methylene)-N(methyl)₂, -ethylene-NH—CO-(ethylene)-N(methyl)₂, -methylene-NH—CO-(methylene)-O-(methyl), -methylene-NH—CO-(ethylene)-O-(methyl), -ethylene-NH—CO -(methylene)-O-(methyl), -methylene-NH—CO-(methylene)-O-(ethyl), -methylene-NH—CO-(ethylene)-O-(ethyl), -ethylene-NH—CO-(methylene)-O-(ethyl), -(methylene)-N(CH₃)—CO-(methylene)-O-(methyl), -(methylene)-N(CH₃)-CO-(ethylene)-O-(methyl), -(ethylene)-N(CH₃)—CO-(methylene)-O-(methyl), -(methylene)-N(CH₃)—CO-(methylene)-O-(ethyl), -(methylene)-N(CH₃)-CO-(ethylene)-O-(ethyl), -(ethylene)-N(CH₃)—CO-(methylene)-O-(ethyl), —O-(methylene)-phenyl, —O-(ethylene)-phenyl, —CO-phenyl, wherein the phenyl in the above groups are optionally substituted by one or more other groups selected from F, Cl, Br, methyl, ethyl, propyl, —O-methyl, —O-ethyl, —O-propyl, —OH, and CF₃.

19. The drug combination according to claim 1, wherein: $R^3$ is oxazole, imidazole, or thiazole, each optionally substituted by one, two, or three further groups independently selected from methyl, ethyl, propyl, isopropyl, O-methyl, O-ethyl, O-propyl, O-isopropyl, OH, F, Cl, Br, CF₃, phenyl, hetaryl, and $C_{3-6}$-cycloalkyl.

20. The drug combination according to claim 1, wherein X is SO₂.

21. The drug combination according to claim 1, wherein the compound of formula 1 is selected from:

1.1 (R)-2-{2-[4-(4-chlorophenyl)-piperidin-1-yl]-5-oxo-6,7-dihydro-5H-5λ⁴-thieno[3,2-d]pyrimidin-4-ylamino}-3-methylbutan-1-ol 1.2 (1-{2-[4-(4-chlorophenyl)-piperidin-1-yl]-5-oxo-6,7-dihydro-5H-5λ⁴-thieno[3,2-d]pyrimidin-4-ylamino}-cyclopropyl)-methanol 1.3 (R)-2-{2-[4-(4-chlorophenyl)-piperidin-1-yl]-5-oxo-6,7-dihydro-5H-5λ⁴-thieno[3,2-d]pyrimidin-4-ylamino}-pentan-1-ol 1.4 (R)-1-{2-[4-(4-chlorophenyl)-piperidin-1-yl]-5-oxo-6,7-dihydro-5H-5λ⁴-thieno[3,2-d]pyrimidin-4-ylamino}-1-(4-fluorophenyl)-2-methylpropan-2-ol 1.5 (S)-5-{2-[4-(4-chlorophenyl)-piperidin-1-yl]-5-oxo-6,7-dihydro-5H-5λ⁴-thieno[3,2-d]pyrimidin-4-ylamino}-1-methylpiperidin-2-one 1.6 {2-[4-(4-chlorophenyl)-piperidin-1-yl]-5-oxo-6,7-dihydro-5H-5λ⁴-thieno[3,2-d]pyrimidin-4-yl}-(tetrahydropyran-4-yl)-amine 1.7 1-(4-(1-hydroxymethylcyclopropylamino)-5-oxo-6,7-dihydro-5H-5λ⁴-thieno[3,2-d]pyrimidin-2-yl)-3'-methyl-1'H-spiro[piperidin-4,4'-quinazolin]-2'(3'H)-one 1.8 {1-[2-(4-benzo[d]isoxazol-3-yl-piperidin-1-yl)-5-oxo-6,7-dihydro-5H-5λ⁴-thieno[3,2-d]pyrimidin-4-ylamino]-cyclopropyl}-methanol 1.9 (1-{2-[4-(2-ethyl-5-fluoro-1H-indol-3-yl)-piperidin-1-yl]-5-oxo-6,7-dihydro-5H-5λ⁴-thieno[3,2-d]pyrimidin-4-ylamino}-cyclopropyl)-methanol 1.10 1-[4-((S)-1-methyl-6-oxopiperidin-3-ylamino)-5-oxo-6,7-dihydro-5H-5λ⁴-thieno[3,2-d]pyrimidin-2-yl]-4-phenylpiperidin-4-carbonitrile 1.11 3'-methyl-1-(4-(tetrahydro-2H-pyran-4-ylamino)-5-oxo-6,7-dihydro-5H-5λ⁴-thieno[3,2-d]pyrimidin-2-yl)-1'H-spiro[piperidin-4,4'-quinazolin]-2'(3'H)-one 1.12 (3-fluorophenyl)-[5-oxo-2-(3,4,5,6-tetrahydro-2H-[4,4]bipyridinyl-1-yl)-6,7-dihydro-5H-5λ⁴-thieno[3,2-d]pyrimidin-4-yl]-amine 1.13 {2-[4-(2-ethyl-5-fluoro-1H-indol-3-yl)-piperidin-1-yl]-5-oxo-6,7-dihydro-5H-5λ⁴-thieno[3,2-d]pyrimidin-4-yl}-(3-fluorophenyl)-amine 1.14 (1-{2-[4-(2,4-difluorophenyl)-piperidin-1-yl]-5-oxo-6,7-dihydro-5H-5λ⁴-thieno[3,2-d]pyrimidin-4-ylamino}-cyclopropyl)-methanol 1.15 {2-[4-(2,4-difluorophenyl)-piperidin-1-yl]-5-oxo-6,7-dihydro-5H-5λ⁴-thieno[3,2-d]pyrimidin-4-yl}-(tetrahydropyran-4-yl)-amine 1.16 (S)-5-[2-(4-benzoxazol-2-yl-piperidin-1-yl)-5-oxo-6,7-dihydro-5H-5λ⁴-thieno[3,2-d]pyrimidin-4-ylamino]-1-methylpiperidin-2-one 1.17 (1-{2-[4-(6-fluorobenzo[d]isoxazol-3-yl)-piperidin-1-yl]-5-oxo-6,7-dihydro-5H-5λ⁴-thieno[3,2-d]pyrimidin-4-ylamino}-cyclopropyl)-methanol 1.18 (1-{2-[4-(5-fluorobenzo[d]isoxazol-3-yl)-piperidin-1-yl]-5-oxo-6,7-dihydro-5H-5λ⁴-thieno[3,2-d]pyrimidin-4-ylamino}-cyclopropyl)-methanol 1.19 {2-[4-(5-furan-2-yl-2H-pyrazol-3-yl)-piperidin-1-yl]-5-oxo-6,7-dihydro-5H-5λ⁴-thieno[3,2-d]pyrimidin-4-yl}-(tetrahydropyran-4-yl)-amine 1.20 (3-fluorophenyl)-{5-oxo-2-[4-(3-pyridin-4-yl-[1,2,4]oxadiazol-5-yl)-piperidin-1-yl]-6,7-dihydro-5H-5λ⁴-thieno[3,2-d]pyrimidin-4-yl}-amine 1.21 (R)-3-methyl-2-{5-oxo-2-[4-(3-pyridin-4-yl-[1,2,4]oxadiazol-5-yl)-piperidin-1-yl]-6,7-dihydro-5H-5λ⁴-thieno[3,2-d]pyrimidin-4-ylamino}-butan-1-ol 1.22 (S)-5-{2-[4-(4-fluorophenoxy)-piperidin-1-yl]-5-oxo-6,7-dihydro-5H-5λ⁴-thieno[3,2-d]pyrimidin-4-ylamino}-1-methylpiperidin-2-one 1.23 (2-{4-[4-(4,5-dihydrooxazol-2-yl)-phenoxy]-piperidin-1-yl}-5-oxo-6,7-dihydro-5H-5λ⁴-thieno[3,2-d]pyrimidin-4-yl)-(tetrahydropyran-4-yl)-amine 1.24 4-{1-[5-oxo-4-(tetrahydropyran-4-ylamino)-6,7-dihydro-5H-5λ⁴-thieno[3,2-d]pyrimidin-2-yl]-piperidin-4-yloxy}-benzoic acid 1.25 2-(1-{2-[4-(4-chlorophenyl)-piperidin-1-yl]-5-oxo-6,7-dihydro-5H-5λ⁴-thieno[3,2-d]pyrimidin-4-ylamino}-cyclopropyl)-propan-2-ol 1.26 {2-[4-(5-tert-butyl-1-methyl-1H-indol-3-yl)-piperidin-1-yl]-5-oxo-6,7-dihydro-5H-5λ⁴-thieno[3,2-d]pyrimidin-4-yl}-(tetrahydropyran-4-yl)-amine 1.27 2-[4-(5-furan-2-yl-1-methyl-1H-pyrazol-3-yl)-piperidin-1-yl]-5-oxo-6,7-dihydro-5H-5λ⁴-thieno[3,2-d]pyrimidin-4-yl}-(tetrahydropyran-4-yl)-amine 1.28 (S)-5-(2-{4-[4-(4,5-dihydrooxazol-2-yl)-phenoxy]-piperidin-1-yl}-5-oxo-6,7-dihydro-5H-5λ⁴-thieno[3,2-d]pyrimidin-4-ylamino)-1-methylpiperidin-2-one 1.29 {2-[4-(5-furan-2-yl-2-methyl-2H-pyrazol-3-yl)-piperidin-1-yl]-5-oxo-6,7-dihydro-5H-5λ⁴-thieno[3,2-d]pyrimidin-4-yl}-(tetrahydropyran-4-yl)-amine 1.30 {2-[4-(1-methyl-1H-imidazo[4,5-c]pyridin-2-yl)-piperidin-1-yl]-5-oxo-6,7-dihydro-5H-5λ⁴-thieno[3,2-d]pyrimidin-4-yl}-(tetrahydropyran-4-yl)-amine 1.31 2-methoxy-N-{1-[5-oxo-4-(tetrahydropyran-4-ylamino)-6,7-dihydro-5H-5λ⁴-thieno[3,2-d]pyrimidin-2-yl]-4-phenylpiperidin-4-ylmethyl}-acetamide 1.32 N-cyclopropyl-N-methyl-4-{1-[5-oxo-4-(tetrahydropyran-4-ylamino)-6,7-dihydro-5H-5λ⁴-thieno[3,2-d]pyrimidin-2-yl]-piperidin-4-yl}-benzamide 1.33 N-cyclopropyl-N-methyl-4-{1-[5-oxo-4-(tetrahydropyran-4-ylamino)-6,7-dihydro-5H-5λ⁴-thieno[3,2-d]pyrimidin-2-yl]-piperidin-4-yloxy}-benzamide 1.34 {5-oxo-2-[4-(pyridin-4-yloxy)-piperidin-1-yl]-6,7-dihydro-5H-5λ⁴-thieno[3,2-d]pyrimidin-4-yl}-(tetrahydropyran-4-yl)-amine 1.35 {2-[4-(4-chlorophenoxy)-piperidin-1-yl]-5-oxo-6,7-dihydro-5H-5λ⁴-thieno[3,2-d]pyrimidin-4-yl}-(tetrahydropyran-4-yl)-amine 1.36 (S)-1-methyl-5-{2-[4-(5-methyl-4-phenyloxazol-2-yl)-piperidin-1-yl]-5-oxo-6,7-dihydro-5H-5λ⁴-thieno[3,2-d]pyrimidin-4-ylamino}-piperidin-2-one 1.37 (1-{2-[4-(5-methyl-4-phenyloxazol-2-yl)-piperidin-1-yl]-5-oxo-6,7-dihydro-5H-5λ⁴-thieno[3,2-d]pyrimidin-4-ylamino}-cyclopropyl)-methanol 1.38 (S)-5-{2-[4-(4,5-diphenyloxazol-2-yl)-piperidin-1-yl]-5-oxo-6,7-dihydro-5H-5λ⁴-thieno[3,2-d]pyrimidin-4-ylamino}-1-methylpiperidin-2-one 1.39 {4-(4-chlorophenyl)-1-[5-oxo-4-(tetrahydropyran-4-ylamino)-6,7-dihydro-5H-5λ⁴-thieno[3,2-d]pyrimidin-2-yl]-piperidin-4-yl}-methanol 1.40 [1-(2-{4-[5-(4-chlorophenyl)-4-methyloxazol-2-yl]-piperidin-1-yl}-5-oxo-6,7-dihydro-5H-5λ⁴-thieno[3,2-d]pyrimidin-4-ylamino)-cyclopropyl]-methanol 1.41 4-(4-chlorophenyl)-1-[5-oxo-4-(tetrahydropyran-4-ylamino)-6,7-dihydro-5H-5λ⁴-thieno[3,2-d]pyrimidin-2-yl]-piperidin-4-ol 1.42 {2-[4-(4-chlorophenyl)-4-methoxypiperidin-1-yl]-5-oxo-6,7-dihydro-5H-5λ⁴-thieno[3,2-d]pyrimidin-4-yl}-(tetrahydropyran-4-yl)-amine 1.43 4-{1-[4-(1-hydroxymethylcyclopropylamino)-5-oxo-6,7-dihydro-5H-5λ⁴-thieno[3,2-d]pyrimidin-2-yl]-piperidin-4-yloxy}-benzonitrile 1.44 5-oxo-2-[4-(4,5,6,7-tetrahydrobenzoxazol-2-yl)-piperidin-1-yl]-6,7-dihydro-5H-5λ⁴-thieno[3,2-d]pyrimidin-4-yl}-(tetrahydropyran-4-yl)-amine 1.45 (S)-5-{2-[4-(4-chlorophenyl)-piperidin-1-yl]-5,5-dioxo-6,7-dihydro-5H-5λ⁶-thieno[3,2-d]pyrimidin-4-ylamino}-1-methylpiperidin-2-one.

22. The drug combination according to claim 1, wherein the NSAID selected from those listed in claim 2, provided that it is is a COX 1-inhibitor or COX 2-inhibitor.

23. The drug combination according to claim 22, wherein the NSAID is selected from ampiroxicam (2.7), cinnoxicam (2.27), droxicam (2.35), isoxicam (2.67), lornoxicam (2.72), meloxicam (2.77), mesalazin (2.78), miroprofen (2.79), mofezolac (2.80), nabumetone (2.81), naproxen (2.82), nifluminic acid (2.83), olsalazine (2.84), oxaprozin (2.85), oxipinac (2.86), oxyphenbutazone (2.87), parecoxib (2.88), phenylbutazone (2.89), pelubiprofen (2.90), pimeprofen (2.91), pirazolac (2.92), piroxicam (2.93), sudoxicam (2.109), and tenoxicam (2.114).

24. The drug combination according to claim 23, wherein the NSAID is celecoxib (2.25), etoricoxib (2.41), lumiracoxib (2.74), parecoxib (2.88), rofecoxib (2.101), or valdecoxib (2.125).

25. The drug combination according to claim 23, wherein the NSAID is meloxicam (2.77) or piroxicam (2.93).

26. The drug combination according to claim 25, wherein the NSAID is meloxicam (2.77).

27. The drug combination according to claim 26, comprising the compound of formula 1 in a single dose of 0.01 mg to 50 mg.

28. The drug combination according to claim 27, wherein the NSAID comprises meloxicam (2.77) in a single dose of 7.5 mg to 30 mg.

* * * * *